US010301324B2

(12) United States Patent
Breslin et al.

(10) Patent No.: US 10,301,324 B2
(45) Date of Patent: May 28, 2019

(54) ATAXIA TELENGIECTASIA AND RAD3-RELATED (ATR) INHIBITORS AND METHODS OF THEIR USE

(71) Applicant: Atrin Pharmaceuticals LLC, Lansdale, PA (US)

(72) Inventors: Henry Joseph Breslin, Lansdale, PA (US); Oren Gilad, Ambler, PA (US); Gerhard Sperl, Salem, NH (US); Eric J. Brown, Wynnewood, PA (US); Laura Butler, Blue Bell, PA (US)

(73) Assignee: Atrin Pharmaceuticals LLC, Ambler, PA (US)

( * ) Notice: Subject to any disclaimer, the term of this patent is extended or adjusted under 35 U.S.C. 154(b) by 0 days.

(21) Appl. No.: 15/486,017

(22) Filed: Apr. 12, 2017

(65) Prior Publication Data

US 2017/0291911 A1 Oct. 12, 2017

Related U.S. Application Data

(60) Provisional application No. 62/321,472, filed on Apr. 12, 2016.

(51) Int. Cl.
*C07D 515/04* (2006.01)
*A61K 31/4985* (2006.01)
*A61K 45/06* (2006.01)

(52) U.S. Cl.
CPC ........ *C07D 515/04* (2013.01); *A61K 31/4985* (2013.01); *A61K 45/06* (2013.01)

(58) Field of Classification Search
CPC .................................................. C07D 515/04
See application file for complete search history.

(56) References Cited

U.S. PATENT DOCUMENTS

| 5,073,641 | A | 12/1991 | Bundgaard et al. |
| 9,133,215 | B2 | 9/2015 | Bailey et al. |
| 2005/0009840 | A1 | 1/2005 | Cui et al. |
| 2005/0143422 | A1 | 6/2005 | Levin et al. |
| 2013/0252961 | A1 | 9/2013 | Bailey et al. |
| 2014/0031351 | A1 | 1/2014 | Breslin et al. |
| 2015/0274710 | A1 | 10/2015 | Charrier et al. |
| 2016/0102104 | A1 | 4/2016 | Breslin et al. |

FOREIGN PATENT DOCUMENTS

| WO | WO2013132376 A1 | 9/2013 |
| WO | WO2015050989 A2 | 4/2015 |
| WO | WO2016061097 A1 | 4/2016 |
| WO | WO2017180723 A1 | 10/2017 |

OTHER PUBLICATIONS

Weber Pharmacology & Therapeutics, 2015, 149, 124-38 (Year: 2015).*
"Prevention—Prostate Cancer Foundation", http://www.pcf.org/site/c.leJRIROrEpH/b.5802029/k.31EA/Prevention.htm, accessed Apr. 18, 2016 (Year: 2016).*
Jones, Organic Reactions, 1997, 49, chapter 1, pp. 1-330 (Year: 1997).*
Brown et al., "ATR Disruption Leads to Chromosomal Fragmentation and Early Embryonic Lethality", Genes & Development, 2000, 14, pp. 397-402.
Bryant et al., "Specific Killing of BRCA2-Deficient Tumours with Inhibitors of Poly(ADP-Ribose) Polymerase", Nature, Apr. 14, 2005, 434, pp. 913-917.
Choi et al., "Protease-Activated Drug Development", Theranostics, 2012, 2(2), pp. 156-178.
Cimprich et al., "ART: An Essential Regulator of Genome Integrity", Nature Reviews Molecular Cell Biology, Aug. 2008, 9, pp. 616-627.
Di Micco et al., "Oncogene-Induced Senescence is a DNA Damage Response Triggered by DNA Hyper-Replication", Nature, Nov. 30, 2006, 444, pp. 638-642.
Fong et al., "Inhibition of Poly(ADP-Ribose) Polymerase in Tumors from BRCA Mutation Carriers", New England Journal of Medicine, 2009, 361, pp. 123-134.
Gilad et al., "Combining ATR Suppression with Oncogenic Ras Synergistically Increases Genomic Instability, Causing Synthetic Lethality or Tumorigenesis in a Dosage-Dependent Manner", Cancer Res., Nov. 2010, 70, pp. 9693-9702.
Charrier et al., "Discovery of Potent and Selective Inhibitors of Ataxia Telengiectasia Mutated and Rad3 Related (ATR) Protein Kinase as Potential Anticancer Agents", J. Med. Chem., Mar. 17, 2011, 54, pp. 2320-2330.
Jacques et al., "Enantiomers, Racemates and Resolutions", Wiley Interscience, New York, Copyright 1981, 37 pages.
Menezes et al., "A Synthetic Lethal Screen Reveals Enhanced Sensitivity to ATR Inhibitor Treatment in Mantle Cell Lymphoma with ATM Loss-of-Function", Mol. Cancer Res., Sep. 17, 2014, pp. 120-129.
Negrini et al., "Genomic Instability—An Evolving Hallmark of Cancer", Nat. Rev. Mol. Cell Biol., Mar. 2010, 11, pp. 220-228.
Reaper et al., "Selective Killing of ATM—or p53-Deficient Cancer Cells Through Inhibition of ATR", Nat. Chem. Biol., Jul. 2011, 7, pp. 428-430.
Schoppy et al., "Oncogenic Stress Sensitizes Murine Cancers to Hypomorphic Suppression of ATR", The Journal of Clinical Investigation, Jan. 2012, 122(1), pp. 241-252.
Wadouachi et al., "Synthesis of Glycosides of Glycuronic, Galacturonic and Mannuronic Acids: An Overview", Molecules, 2011, 16, pp. 3933-3968.
Zawilska et al., "Prodrugs: A Challenge for the Drug Development", Pharmacological Reports, 2013, 65, pp. 1-14.
Zhong et al., "Cathepsin B-Cleavable Doxorubicin Prodrugs for Targeted Cancer Therapy (Review)", International Journal of Oncology, 2013, 42, pp. 373-383.
Gygi et al., "Similarity and Categorization of Environmental Sounds", Perception & Psychophysics, Aug. 2007, 69 (6), pp. 839-855.
International Patent Application No. PCT/US17/27172: International Search Report and Written Opinion dated Jul. 13, 2017, 8 pages.

(Continued)

*Primary Examiner* — Noble E Jarrell
(74) *Attorney, Agent, or Firm* — BakerHostetler

(57) ABSTRACT

The disclosure is directed to compounds and compositions that inhibit Ataxia Telengiectasia And Rad3-Related (ATR) Protein Kinase and methods of their use.

45 Claims, 11 Drawing Sheets

(56) References Cited

OTHER PUBLICATIONS

Kim, et al., "Targeting the ATR/CHK1 Axis with PARP Inhibition Results in Tumor Regression in BRCA-Mutant Ovarian Cancer Models," Clin. Cancer Res. 23(12):3097-3108, Jun. 15, 2017.

Min et al., "Therapeutics AZD6738, A Novel Oral Inhibitor of ATR, Induces Synthetic Lethality with ATM Deficiency in Gastric Cancer Cells," Mol. Cancer Ther., 16(4):566-577, Apr. 2017.

Klattenhoff, "Loss of NEIL3 DNA glycosylase markedly increases replication associated double strand breaks and enhances sensitivity to ATR inhibitor in glioblastoma cells," Oncotarget, 2017, vol. 8, (No. 68), pp. 112942-112958.

Wengner et al., "Synergistic activity of the ATR inhibitor BAY 1895344 in combination with DNA damage-inducing and DNA repair-compromising therapies in preclinical tumor models," Poster presented at the AACR Annual Meeting, Apr. 14-18, 2018, Chicago, IL, USA.

Schoppy et al., "Oncogenic stress sensitizes murine cancers to hypomorphic suppression of ATR," J. Clin. Invest., 2012, 122(1):241-252.

\* cited by examiner

Strong inhibition of purified ATR observed with acids

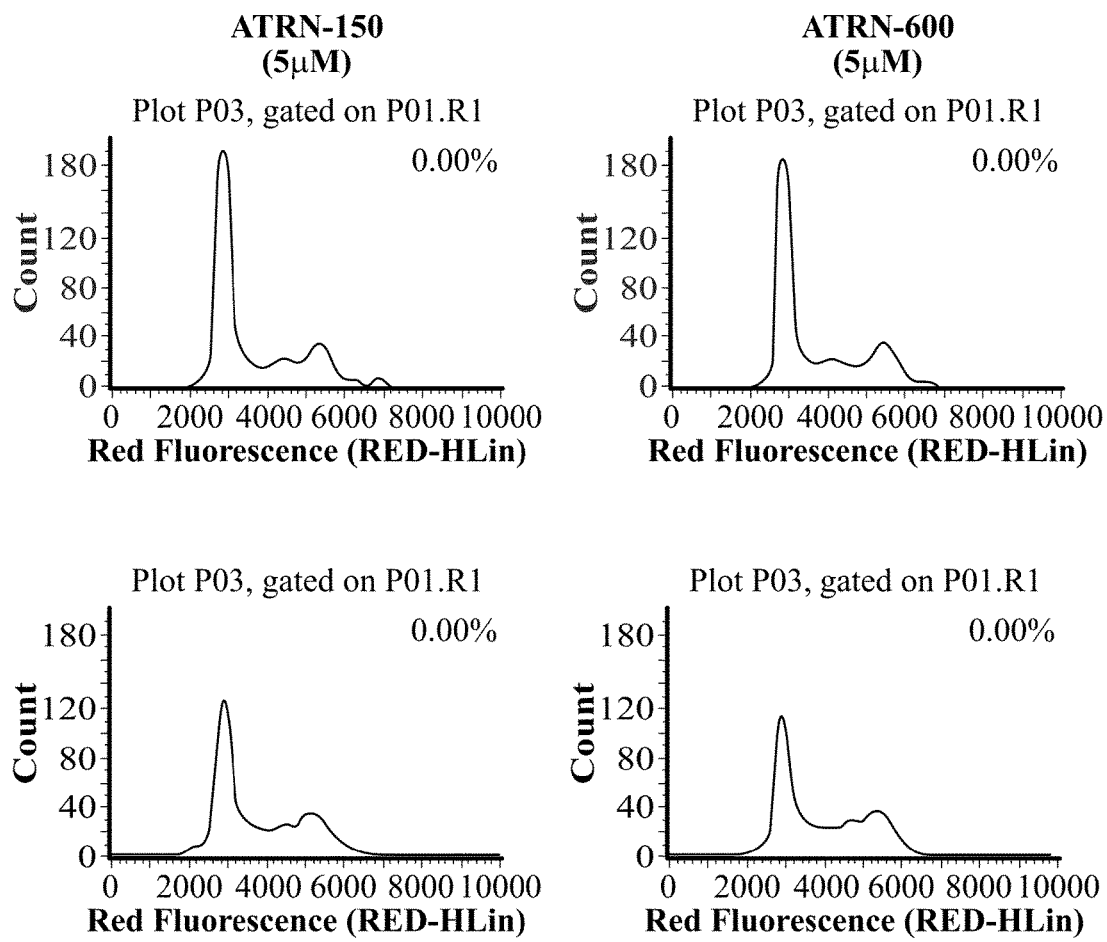
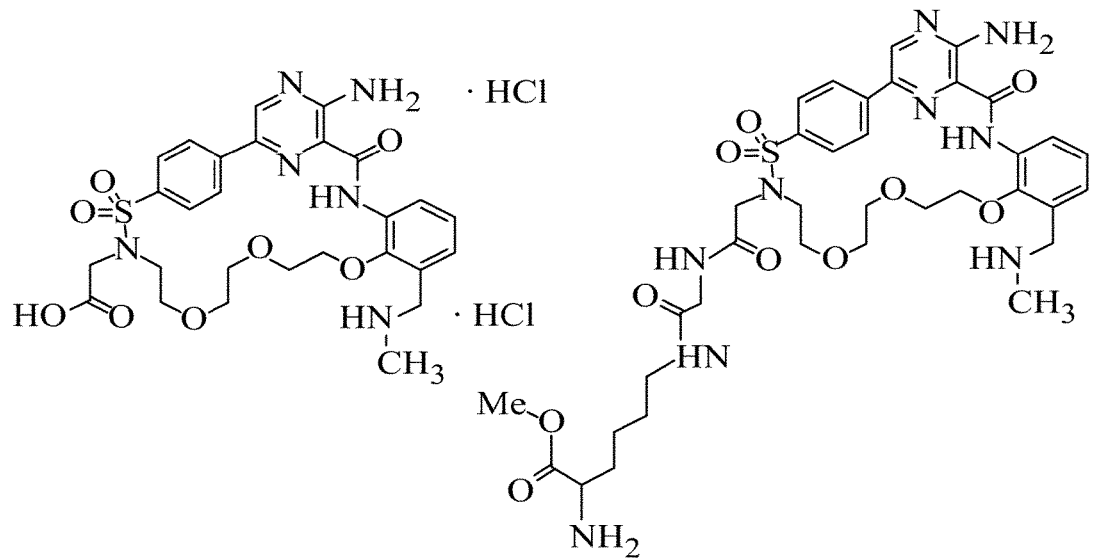
*FIG. 7 (Cont...)*

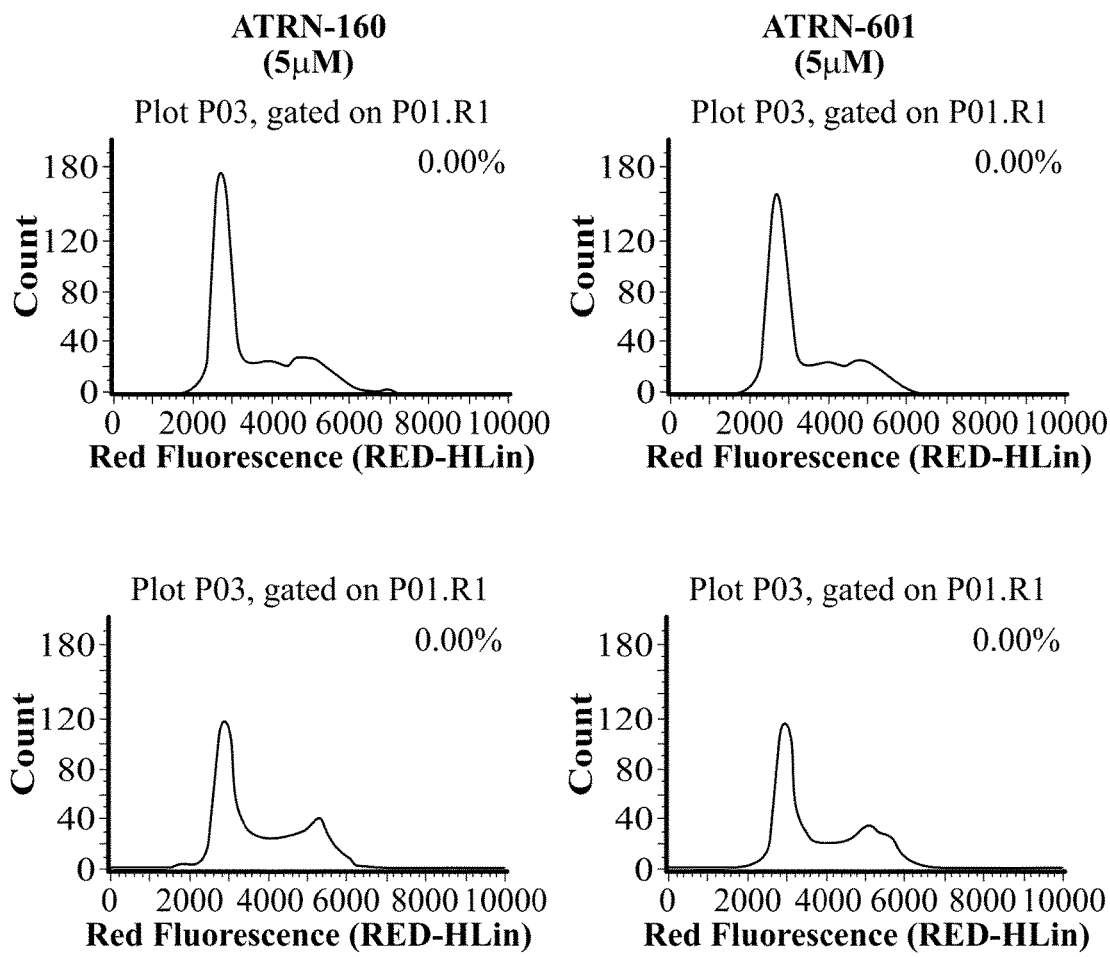
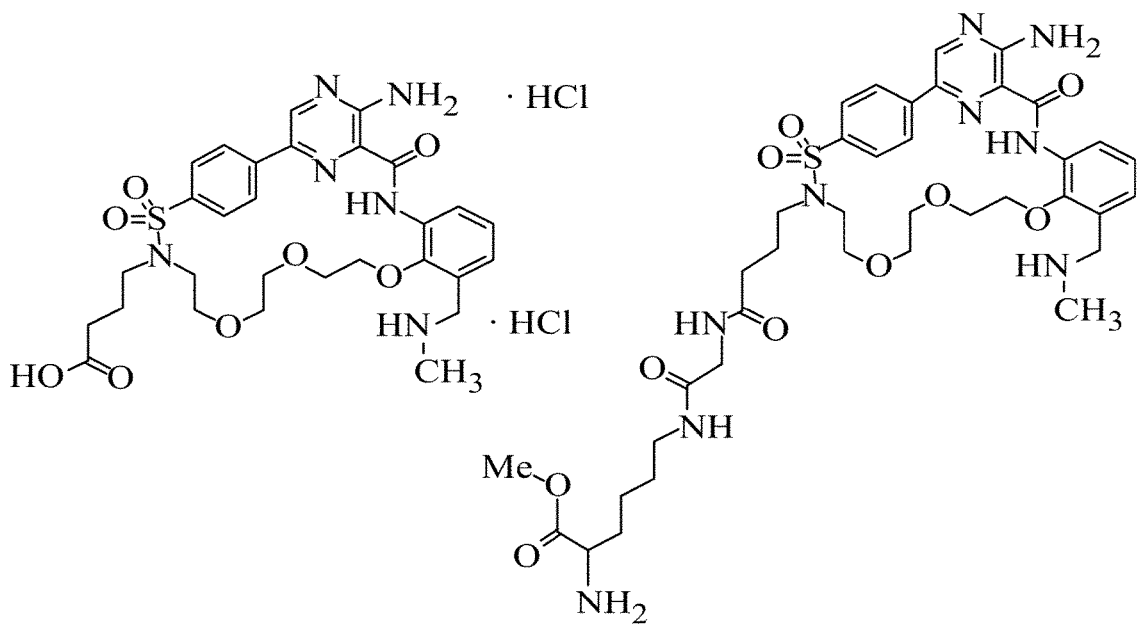
FIG. 7 (Cont...)

ATAXIA TELENGIECTASIA AND RAD3-RELATED (ATR) INHIBITORS AND METHODS OF THEIR USE

CROSS-REFERENCE TO RELATED APPLICATIONS

This application claims priority of U.S. Provisional Patent Application No. 62/321,472, filed Apr. 12, 2016, which is herein incorporated by reference.

TECHNICAL FIELD

The disclosure is directed to compounds and compositions that inhibit ataxia telengiectasia and rad3-related (ATR) protein kinase and methods of their use.

BACKGROUND

That ATR suppression to clinically relevant levels has the potential to be effective in a wide spectrum of cancers is supported by several lines of evidence. Ataxia telengiectasia and rad3-related (ATR) protein kinase is integral to the replication stress response. ATR belongs to a family of kinases, i.e., phosphatidyl inositol 3' kinase-related kinases (PIKKs), that are involved in the signaling and repair of DNA damage. While other members of this family (ataxia-telangiectasia mutated (ATM) and DNA-dependent protein kinase catalytic subunit (DNA-PKcs)) are required for the repair of double strand breaks (DSBs), ATR is recruited to, and activated by, single strand DNA (ssDNA) generated at stalled replication forks or as an intermediate in the repair of DSBs. Upon replication fork stalling activated ATR phosphorylates the downstream kinase Chk1 resulting in stabilization of the replication fork and inhibition of cell-cycle progression, thus allowing time for resolution of the stress and continued replication. When the ATR-Chk1 pathway is disrupted stalled replication forks collapse into DSBs, thus if unresolved, replication stress can cause genomic instability and negatively impact cell survival (Karlene A. Cimprich & David Cortez, ATR: an essential regulator of genome integrity, Nature Reviews Molecular Cell Biology, August 2008, 9, 616-627). Due to its vital role in replication, loss of ATR is early-embryonic lethal in mice (Eric J. Brown and David Baltimore, ATR disruption leads to chromosomal fragmentation and early embryonic lethality, Genes & Development, 2000, 14, 397-402). However, it is important to note that significant suppression of ATR activity (by more than 90%) by mutations in ATR (as would be replicated by treatment with the inhibitors discussed and disclosed herein) is well tolerated by bone marrow and intestinal epithelium, the tissues that are most sensitive to traditional chemotherapeutics (David W. Schoppy et al., Oncogenic stress sensitizes murine cancers to hypomorphic suppression of ATR, The Journal of Clinical Investigation, 2012, 122(1), 241-252).

ATR inhibition is synthetically lethal in cancers with mutations that cause oncogenic stress or disruption of the DNA damage response (DDR). Genetic changes associated with cancer promote the activation of the replicative stress response and other DNA damage response (DDR) pathways (Di Micco R. et al., Oncogene-induced senescence is a DNA damage response triggered by DNA hyper-replication, Nature 2006 Nov. 30, 444(7119):638-42; Negrini S. et al., Genomic instability—an evolving hallmark of cancer, Nat. Rev. Mol. Cell Biol. 2010 March, 11(3):220-22). Such oncogenic stress inducing alterations include K-Ras$^{G12D}$ and H-Ras$^{G12V}$ mutations, and c-Myc amplification. Activation of the DDR by oncogenic stress has been proposed to contribute to selection for mutation, and loss of, p53 and ATM (Negrini S. et al., Genomic instability—an evolving hallmark of cancer, Nat. Rev. Mol. Cell Biol. 2010 March, 11(3):220-228). Mutations in the tumor suppressor p53 are found in ~50% of all human cancers. Similar mutation frequencies are observed in the oncogene Myc, while significant numbers of cancers also harbor mutations in the Ras family of genes (~16%) and to a lesser degree the DDR protein ATM. Alterations in these genes cause an increased reliance on the ATR-Chk1 pathway for genome maintenance. Studies have found that ATR inhibition elicits synthetic lethality under each of these cancer associated conditions (Gilad O. et al., Combining ATR suppression with oncogenic Ras synergistically increases genomic instability, Cancer Res. 2010, 70(23), 9693-702; Schoppy et. al., J. Clin. Invest, 2012; Reaper P. M. et al., Selective killing of ATM- or p53-deficient cancer cells through inhibition of ATR, Nat. Chem. Biol., 2011, 7(7), 428-30; Menezes D. L. et al., A Synthetic Lethal Screen Reveals Enhanced Sensitivity to ATR Inhibitor Treatment in Mantle Cell Lymphoma with ATM Loss-of-function, Mol. Cancer Res., 2014, Epub ahead of print).

Cancers deficient in components of the homologous recombination pathway, such as those harboring mutations in BRCA1 and BRCA2, are highly sensitive to PARP inhibition (Fong, Inhibition of Poly(ADP-Ribose) Polymerase in Tumors from BRCA Mutation Carriers, New England Journal of Medicine. 2009, 361:123-134). While PARP is required for the repair of single strand breaks (SSBs), preventing their collapse into DSBs, ATR stabilizes replication forks, similarly preventing collapse and formation of DSBs. Loss of PARP and ATR activities therefore both force cells to rely on the DSB repair pathway. It is the inability of BRCA mutant cells to repair DSBs that renders them sensitive to PARP inhibition (Bryant H. E. et al. Specific killing of BRCA2-deficient tumours with inhibitors of poly(ADP-ribose) polymerase, Nature 2005 Apr. 14, 434(7035), 913-7), it is therefore reasonable to suppose that cells deficient in the DDR, such as those harboring BRCA mutations, would also be sensitive to ATR inhibition.

Compounds that inhibit ATR are needed.

SUMMARY

The disclosure is directed to compounds of Formula (I) or Formula (II):

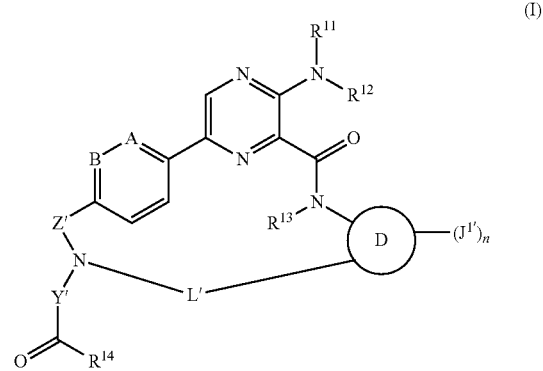

3
-continued

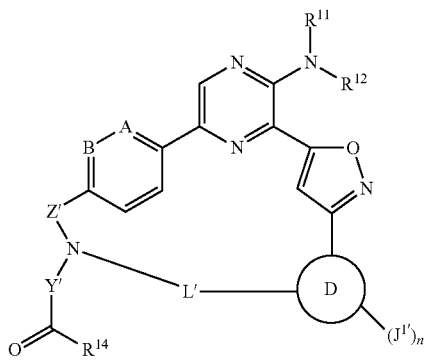
(II)

wherein A is CH, C—C$_{1-6}$alkyl, C—C$_{1-6}$haloalkyl, or N; B is CH, C—C$_{1-6}$alkyl, C—C$_{1-6}$haloalkyl, or N; ring D is phenylene or pyridylene; R$^{11}$ is H or C$_{1-6}$alkyl; R$^{12}$ is H or C$_{1-6}$alkyl; R$^{13}$ is H or C$_{1-6}$alkyl; R$^{14}$ is OH, —OC$_{1-30}$alkyl, —O-aryl, —O—C$_{1-30}$alk-C(O)C$_{1-30}$alkyl, —O—C$_{1-30}$alk-C(O)N(R$^{15}$)(R$^{16}$), —O-monosaccharide, —S—C$_{1-30}$alkyl, a peptidyl moiety, an isopeptide moiety, or a peptidyl-isopeptide moiety; R$^{15}$ and R$^{16}$ are, independently, optionally substituted C$_{1-30}$alkyl, C$_{2-20}$alkenyl, aryl, arylalkyl, or C$_{3-10}$cycloalkyl; Z' is —SO$_2$— or —C(O)—; Y' is an alkylene; n is 1 or 2; each J$^{1'}$ is, independently, H, halogen, optionally substituted —C$_{1-6}$alkyl, optionally substituted C$_{1-6}$haloalkyl, optionally substituted —C$_{1-6}$alkoxy, NH$_2$, NH-(optionally substituted C$_{1-6}$alkyl), N-(optionally substituted C$_{1-6}$alkyl)(optionally substituted C$_{1-6}$alkyl), —C$_{1-6}$alk-NH-(optionally substituted C$_{1-6}$alkyl), or —C$_{1-6}$alk-NH—C$_{0-6}$alk-(optionally substituted C$_{3-6}$heterocycloalkyl); and L' is a 7 to 17-membered linking group comprising an alkylene interrupted by 1, 2, 3, 4 or 5 heteroatom moieties selected from —O—, —NH—, —N(C$_{1-6}$alkyl), —N(optionally substituted C$_{1-6}$alkyl), and —N(C$_{1-6}$alkyl)-O(optionally substituted C$_{1-6}$alkyl); or a pharmaceutically acceptable salt thereof.

The disclosure also is directed to compounds of Formula (III) and (IV):

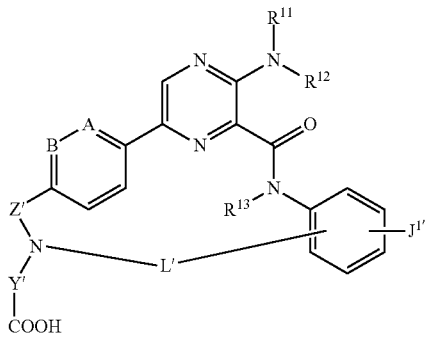
(III)

4
-continued

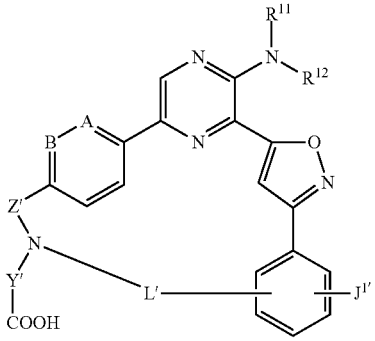
(IV)

wherein A is CH or N; B is CH or N; R$^{11}$ is H or C$_{1-6}$alkyl; R$^{12}$ is H or C$_{1-6}$alkyl; R$^{13}$ is H or C$_{1-6}$alkyl; Z' is —SO$_2$— or —C(O)—; Y' is an alkylene; J$^{1'}$ is H, optionally substituted —C$_{1-6}$alkyl, —C$_{1-6}$alk-NH-(optionally substituted C$_{1-6}$alkyl), or —C$_{1-6}$alk-NH—C$_{0-6}$alk-(optionally substituted C$_{3-6}$heterocycloalkyl); and L' is a 7 to 17-membered linking group comprising an alkylene optionally interrupted by 1, 2, 3, 4 or 5 heteroatom moieties selected from —O—, —NH—, —N(C$_{1-6}$alkyl), —N(optionally substituted C$_{1-6}$alkyl), and —N(C$_{1-6}$alkyl)-O(optionally substituted C$_{1-6}$alkyl), as well as pharmaceutically acceptable salts thereof. Compositions comprising any of the compounds described herein, including compounds of Formula (I), Formula (II), Formula (III), and Formula (IV), as well as methods of using the compounds to treat diseases or disorders are also described.

DETAILED DESCRIPTION OF ILLUSTRATIVE EMBODIMENTS

Figure 1:
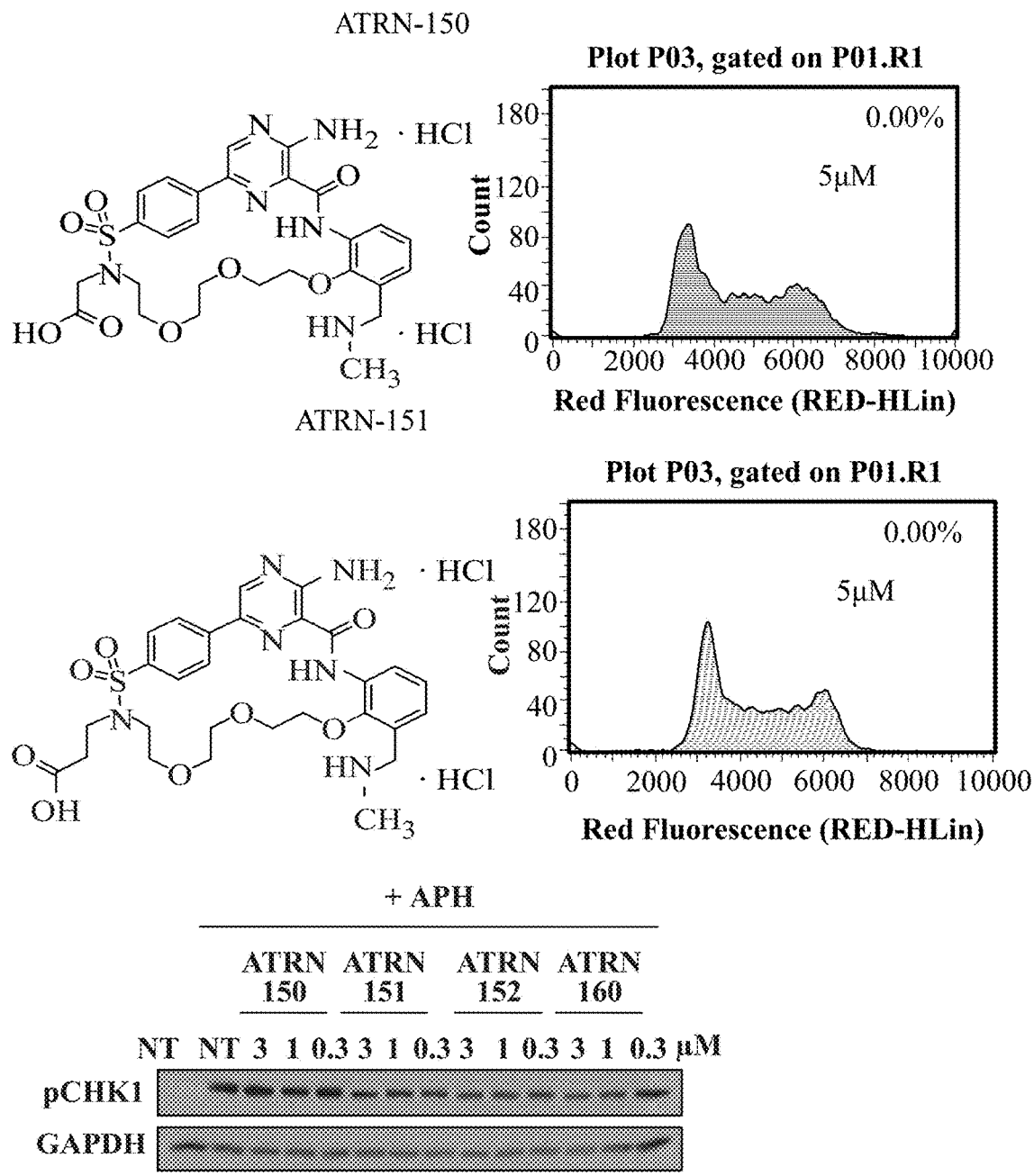
FIG. 1 shows inhibition of cellular ATR using acids ATRN-150 and ATRN-151.
Figure 2:
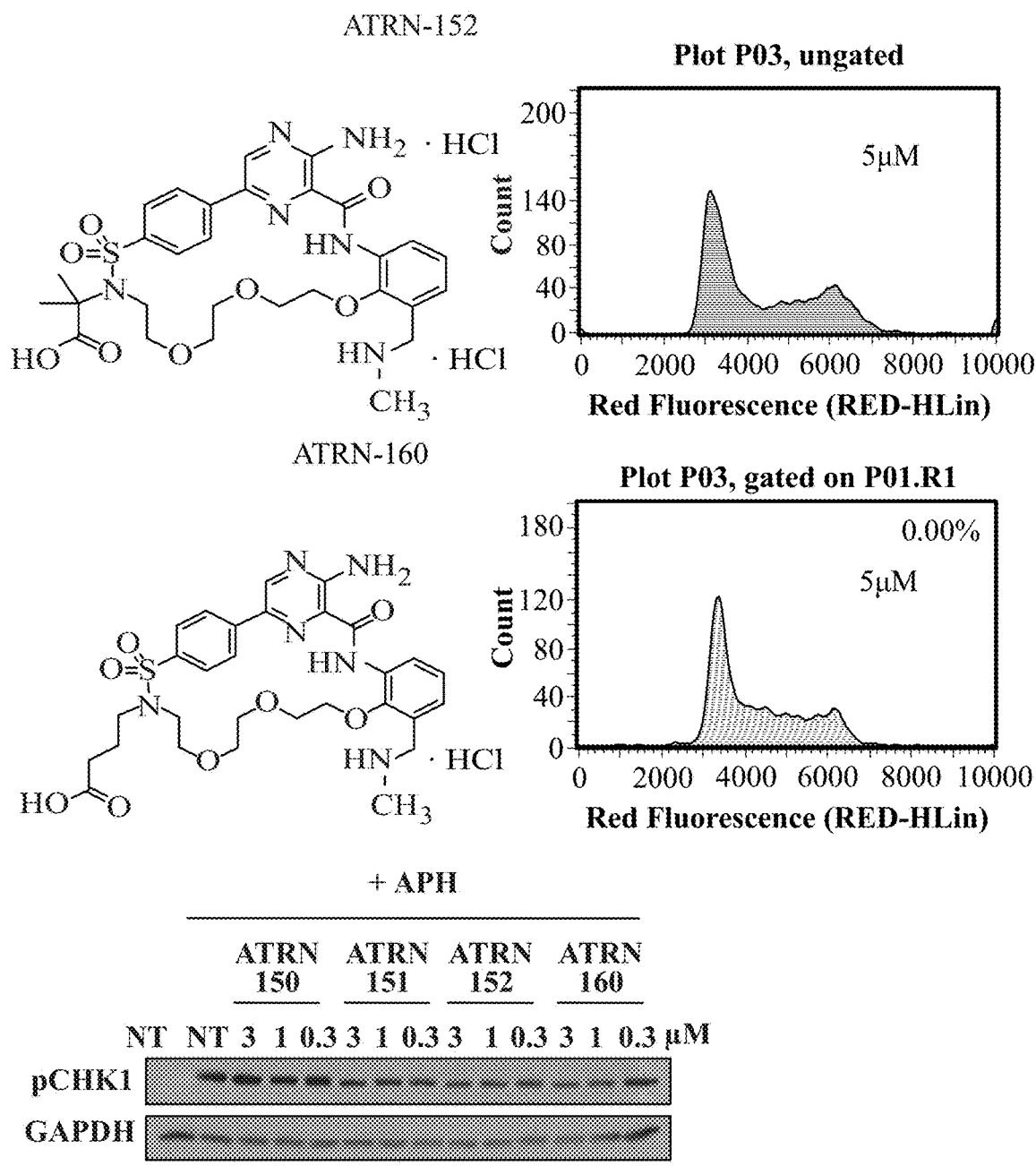
FIG. 2 shows inhibition of cellular ATR using acids ATRN-152 and ATRN-160.
Figure 3:
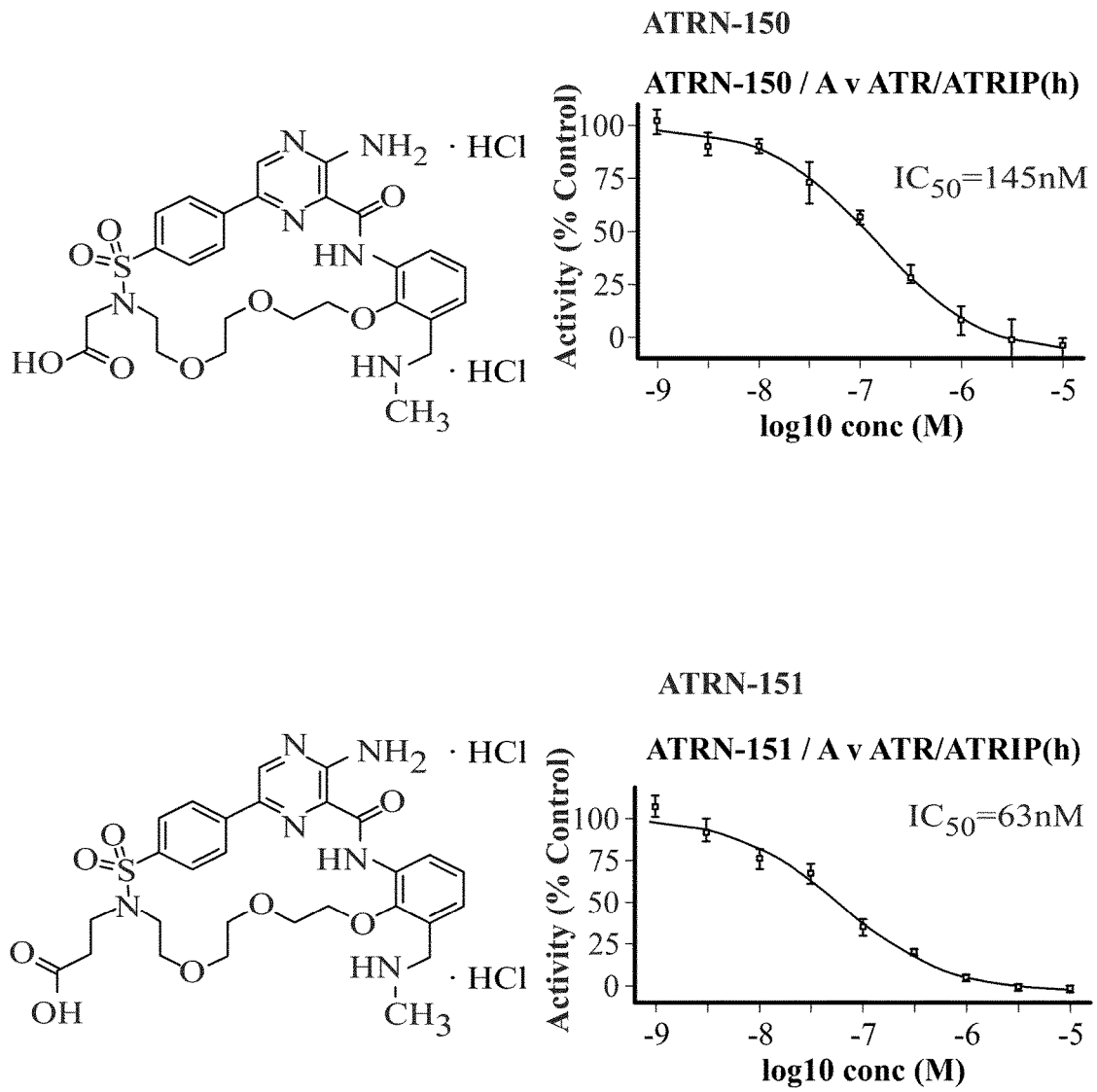
FIG. 3 shows the inhibition of purified ATR using ATRN-150 and ATRN-151.
Figure 4:
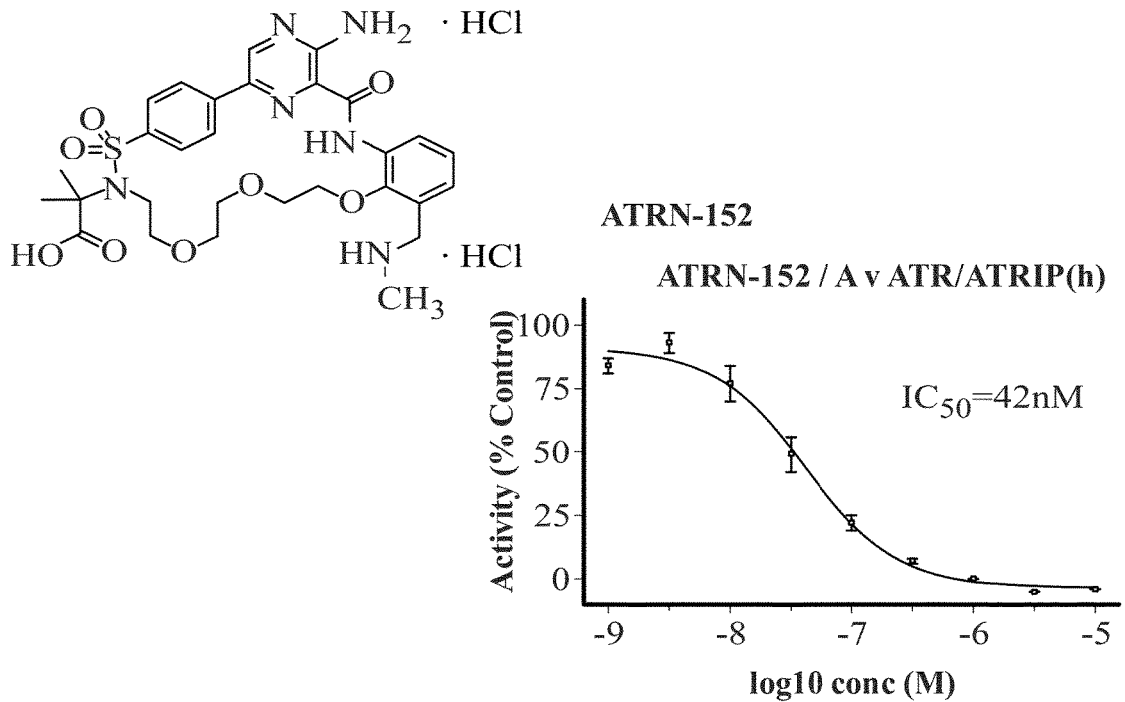
FIG. 4 shows the of inhibition of purified ATR using acids ATRN-152 and ATRN-160.
Figure 4:
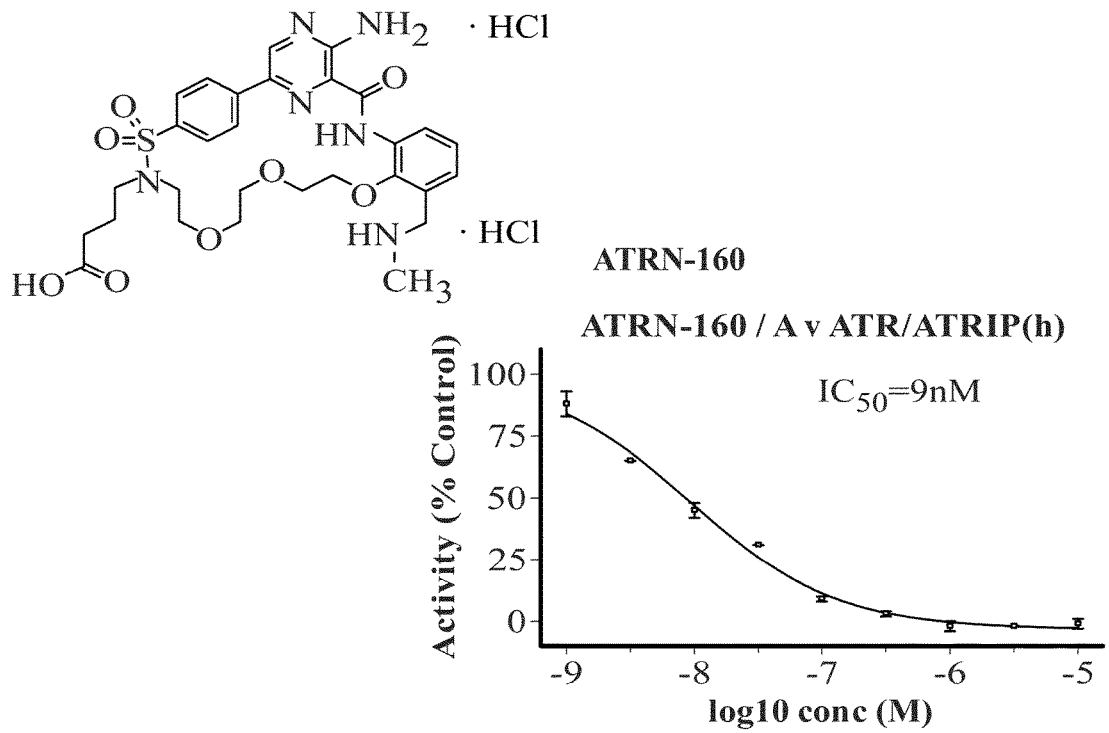
Figure 5:
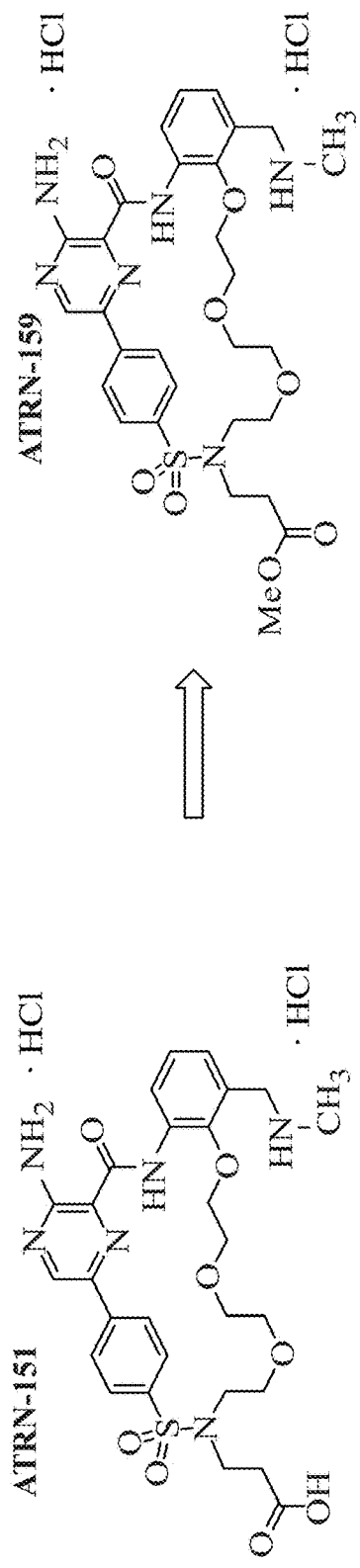
FIG. 5 shows the comparison of inhibition of cellular and purified ATR using acid ATRN-151 and ester counterpart ATRN-159.
Figure 5:
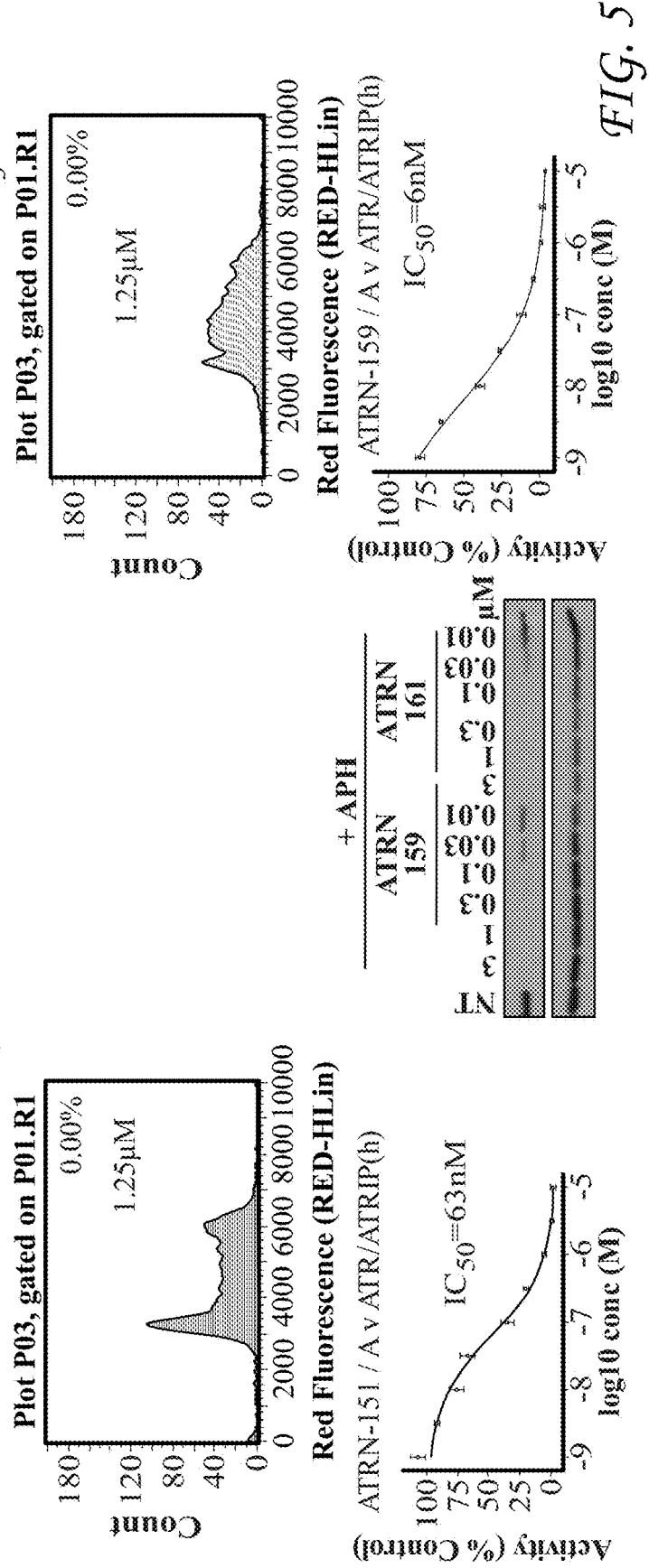
Figure 6:
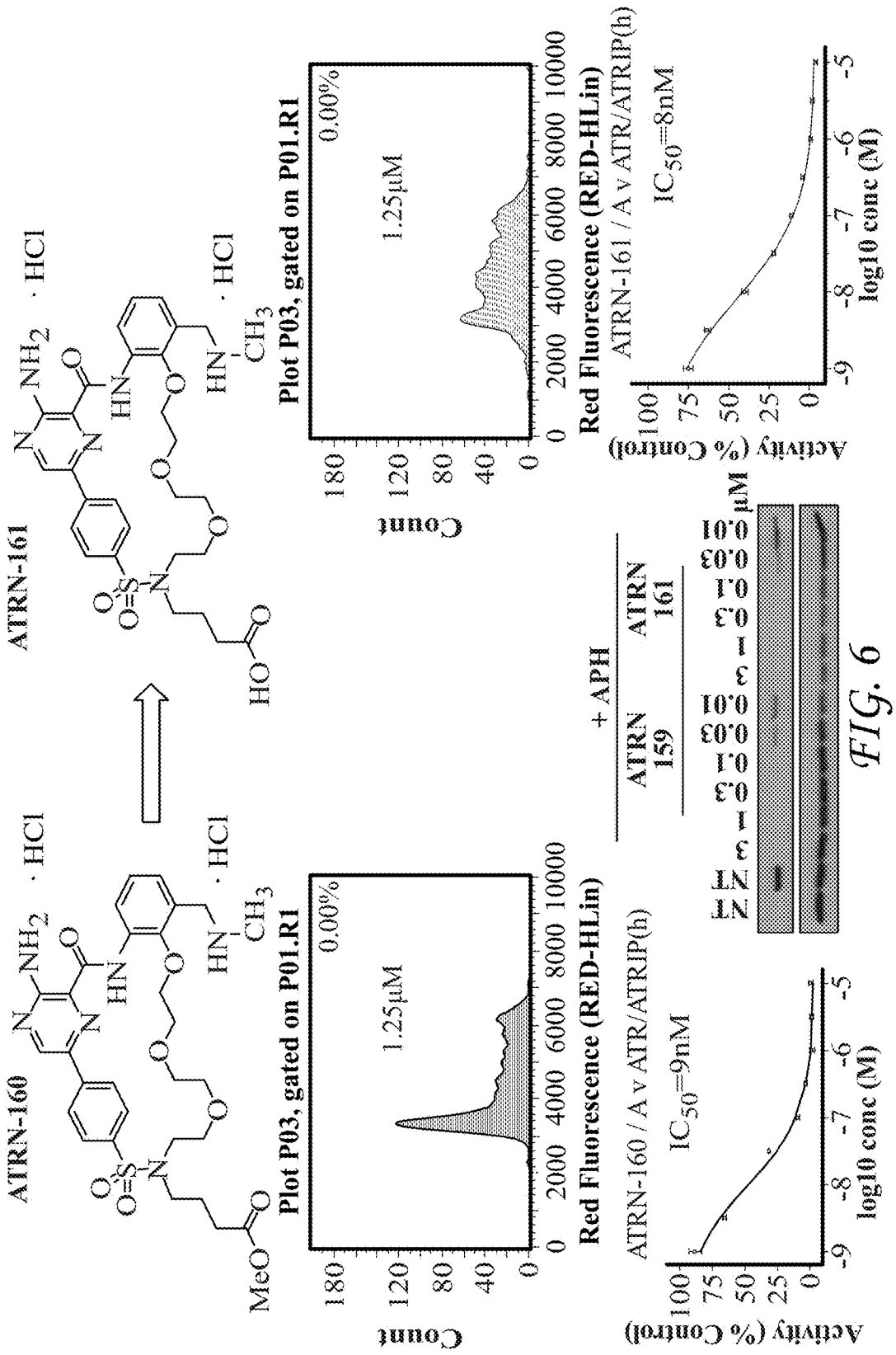
FIG. 6 shows the comparison of inhibition of cellular and purified ATR using acid ATRN-160 and ester counterpart ATRN-161.
Figure 7:
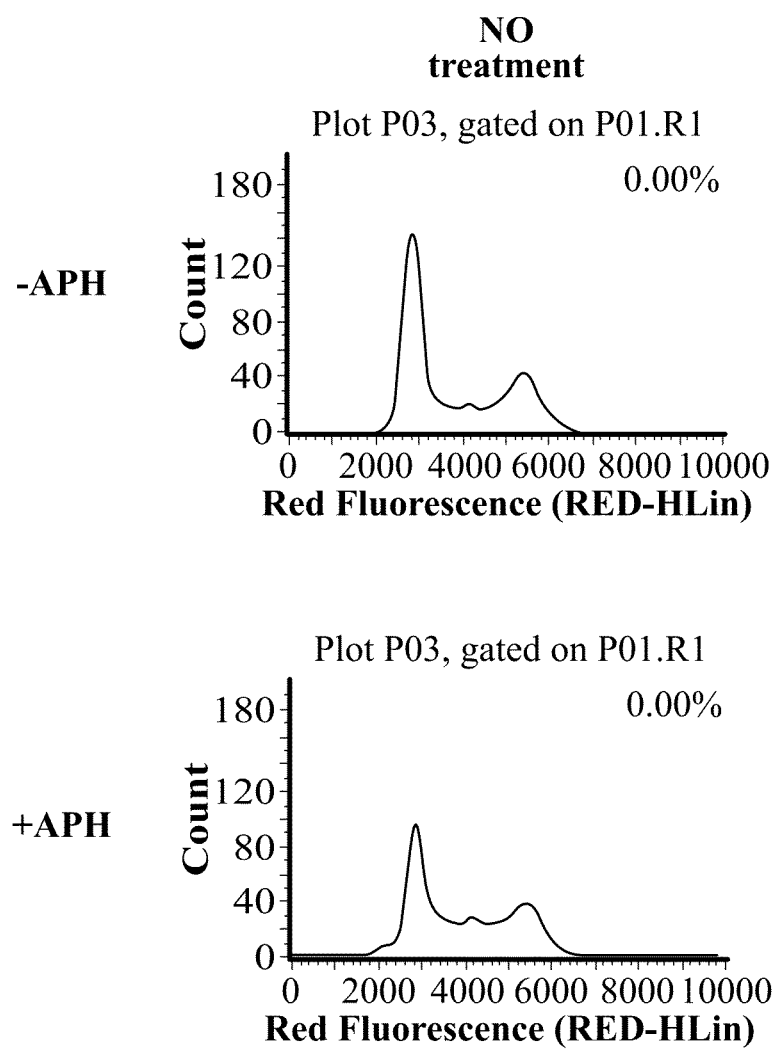
FIGS. 7-9 compares the inhibition of isopeptide pro-drugs described herein with their corresponding acids.
Figure 8:
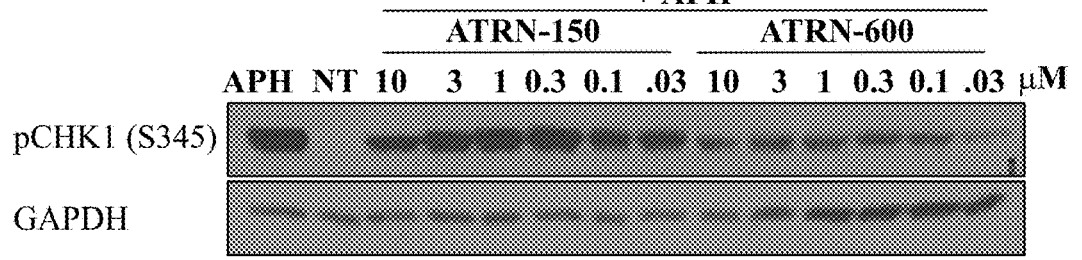
Figure 8:
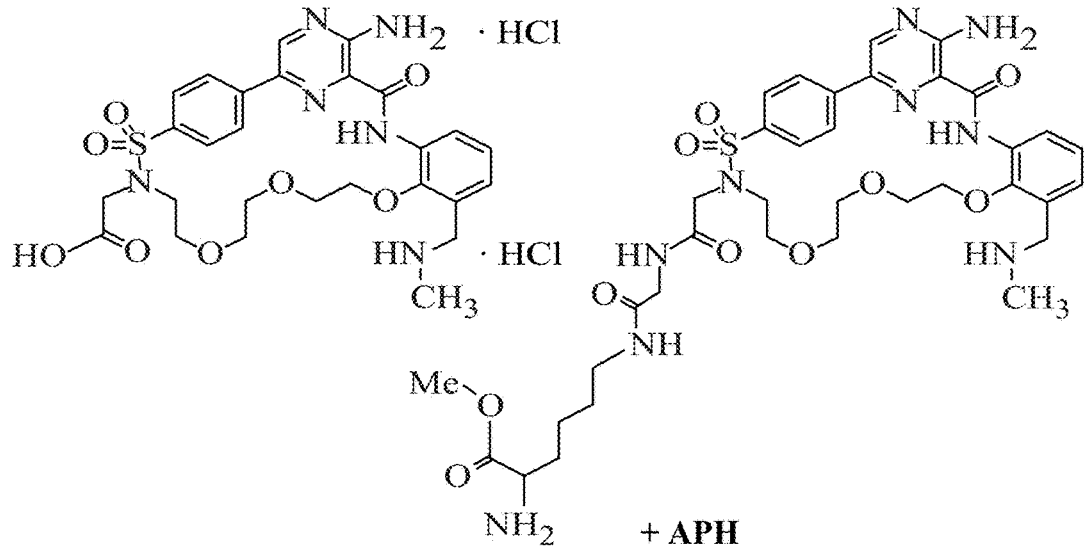
Figure 8:
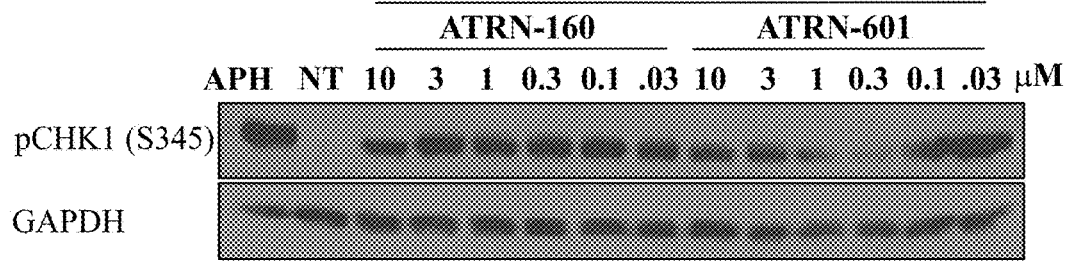
Figure 8:
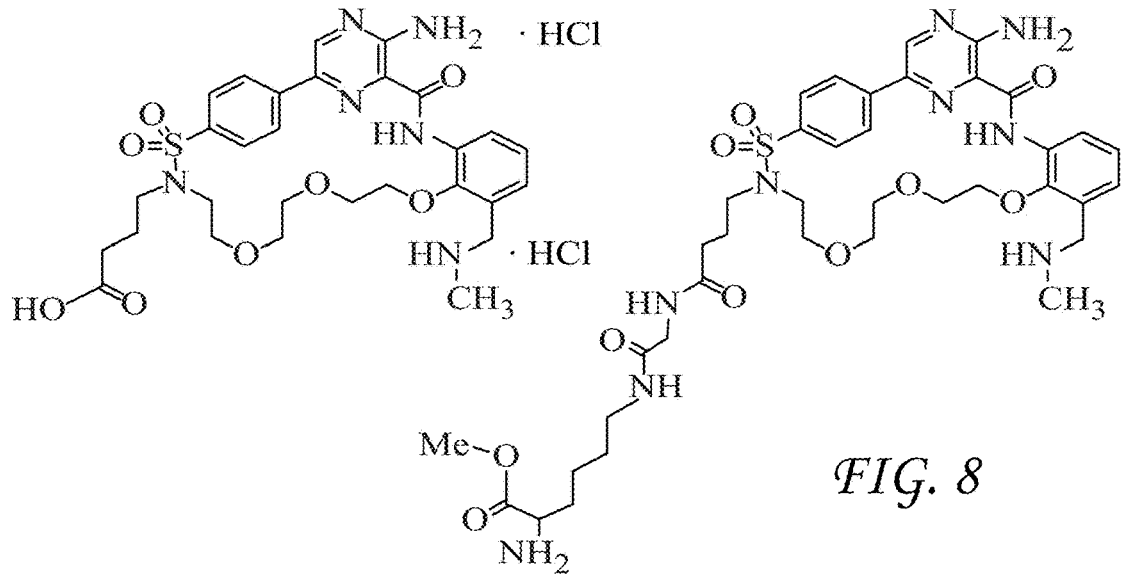
Figure 9:
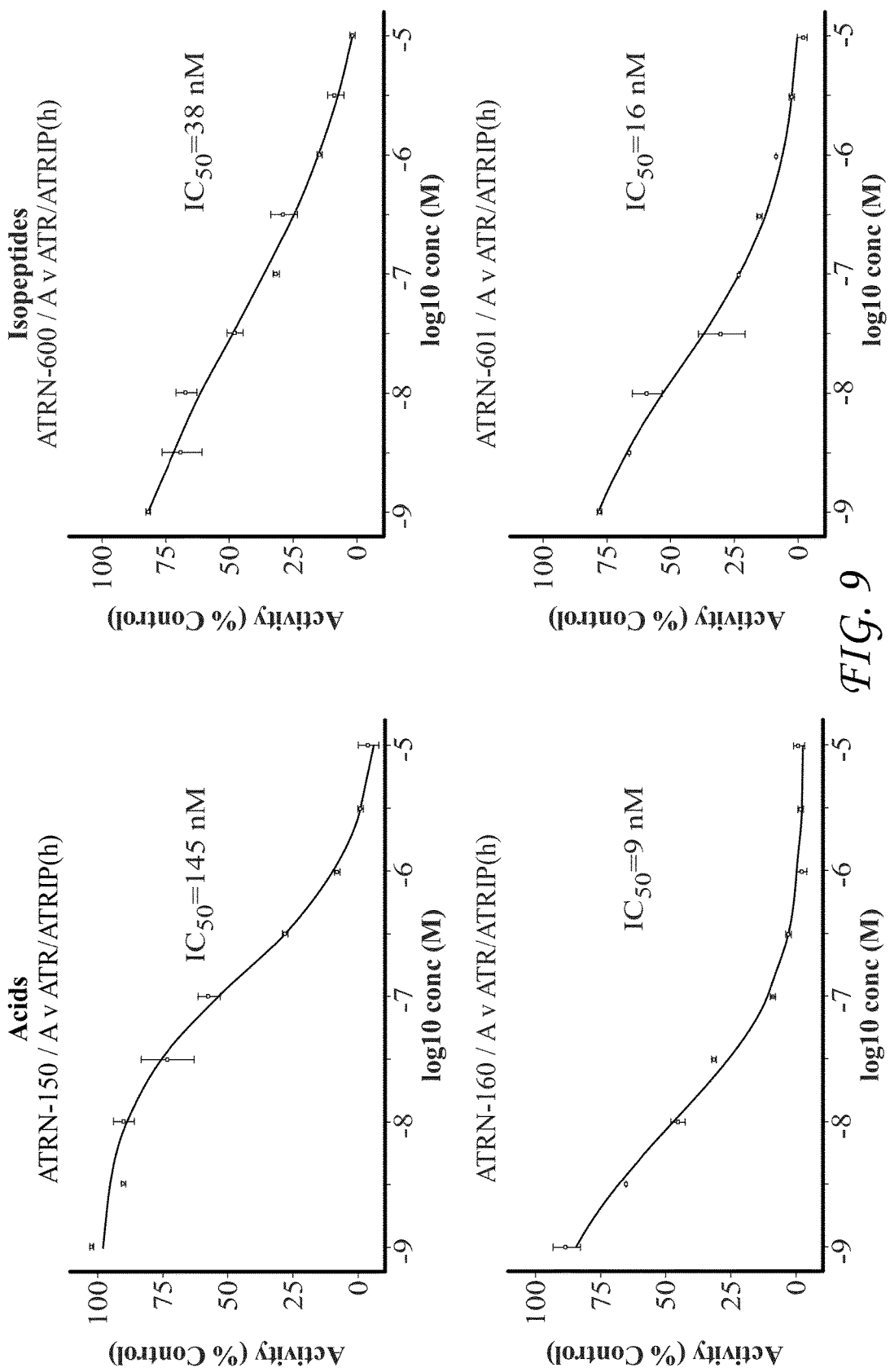

The disclosure may be more fully appreciated by reference to the following description, including the following glossary of terms and the concluding examples. It is to be appreciated that certain features of the disclosed compositions and methods which are, for clarity, described herein in the context of separate aspects, may also be provided in combination in a single aspect.

In the following descriptions of exemplary embodiments of the present invention, all references, including publications, patent applications, and patents, cited herein are incorporated by reference into this application to the same extent as if each reference were individually and specifically indicated to be incorporated by reference and were set forth in its entirety herein.

Conversely, various features of the disclosed compositions and methods that are, for brevity, described in the context of a single aspect, may also be provided separately or in any subcombination.

It will be appreciated by those skilled in the art that changes could be made to the exemplary embodiments shown and described above without departing from the broad inventive concept thereof. It is understood, therefore, that this invention is not limited to the exemplary embodiments shown and described, but it is intended to cover modifications within the spirit and scope of the present invention as defined by the claims. For example, specific features of the exemplary embodiments may or may not be part of the claimed invention and features of the disclosed embodiments may be combined. Unless specifically set forth herein, the terms "a", "an" and "the" are not limited to one element but instead should be read as meaning "at least one".

When a range of carbon atoms is used herein, for example, $C_{1-6}$, all ranges, as well as individual numbers of carbon atoms are encompassed. For example, "$C_{1-3}$" includes $C_{1-3}$, $C_{1-2}$, $C_{2-3}$, $C_1$, $C_2$, and $C_3$.

The term "alkyl" refers to a straight- or branched-chain alkyl group having from 1 to 12 carbon atoms ("$C_{1-12}$"), preferably 1 to 6 carbons atoms ("$C_{1-6}$"), in the chain. Examples of alkyl groups include methyl (Me, $C_1$alkyl) ethyl (Et, $C_2$alkyl), n-propyl ($C_3$alkyl), isopropyl ($C_3$alkyl), butyl ($C_4$alkyl), isobutyl ($C_4$alkyl), sec-butyl ($C_4$alkyl), tert-butyl ($C_4$alkyl), pentyl ($C_5$alkyl), isopentyl ($C_5$alkyl), tert-pentyl ($C_5$alkyl), hexyl ($C_6$alkyl), isohexyl ($C_6$alkyl), and groups that in light of the ordinary skill in the art and the teachings provided herein would be considered equivalent to any one of the foregoing example.

"Cycloalkyl" or "carbocyclyl" refers to a monocyclic or polycyclic radical that contains carbon and hydrogen, and may be saturated, or partially unsaturated. In some preferred embodiments, cycloalkyl groups include groups having from 3 to 12 ring atoms (i.e. ($C_{3-12}$)cycloalkyl or ($C_{3-12}$) cycloalkyl). Whenever it appears herein, a numerical range such as "3 to 12" in ($C_{3-12}$)cycloalkyl or ($C_{3-12}$)cycloalkyl refers to each integer in the given range e.g., "3 to 12 carbon atoms" means that the cycloalkyl group may consist of 3 carbon atoms, 4 carbon atoms, 5 carbon atoms, etc., up to and including 12 carbon atoms. Illustrative examples of cycloalkyl groups include, but are not limited to cyclopropyl, cyclobutyl, cyclopentyl, cyclopentenyl, cyclohexyl, cyclohexenyl, cycloseptyl, cyclooctyl, cyclononyl, cyclodecyl, norbornyl, and the like. Unless stated otherwise specifically in the specification, a cycloalkyl group is optionally substituted by one or more substituents is optionally substituted by one or more substituents described as suitable substituents for alkyl and cycloalkyl respectively.

"Carbocyclylalkyl" as used herein refers to carbocyclyl-alkyl, wherein carbocyclyl and alkyl are defined herein.

An "alkene" or "alkenyl" moiety refers to a group consisting of at least two carbon atoms and at least one carbon-carbon double bond. In some embodiments, alkenyl includes $C_{2-12}$alkenyl, $C_{2-10}$, $C_{2-8}$alkenyl, $C_{2-6}$alkenyl, or $C_{2-5}$alkenyl. In some aspects, the alkenyl is $C_2$alkenyl, $C_3$alkenyl, $C_4$alkenyl, $C_5$alkenyl, $C_6$alkenyl, $C_7$alkenyl, $C_8$alkenyl, $C_9$alkenyl, $C_{10}$alkenyl, $C_{11}$alkenyl, or $C_{10}$alkenyl.

An "alkyne" or "alkynyl" moiety refers to a group consisting of at least two carbon atoms and at least one carbon-carbon triple bond. The alkynyl moiety, may be branched, straight chain, or cyclic. In some embodiments, alkynyl includes $C_{2-12}$alkynyl, $C_{2-10}$alkynyl, $C_{2-8}$alkynyl, $C_{2-6}$alkynyl, or $C_{2-5}$alkynyl. In some aspects, the alkynyl is $C_2$alkynyl, $C_3$alkynyl, $C_4$alkynyl, $C_5$alkynyl, $C_6$alkynyl, $C_7$alkynyl, $C_8$alkynyl, $C_9$alkynyl, $C_{10}$alkynyl, $C_{11}$alkynyl, or $C_{12}$alkynyl.

"Haloalkyl" refers to an alkyl radical, as defined above, that is substituted by one or more halogen atoms. Examples of haloalkyl include, but are not limited to, fluoroalkyl such as trifluoromethyl, difluoromethyl, 2,2,2-trifluoroethyl, 1-fluoromethyl-2-fluoroethyl, and the like. The alkyl part of the haloalkyl radical may be optionally substituted as defined above for an alkyl group.

"Halo", "halide", or, alternatively, "halogen" is intended to mean fluoro, chloro, bromo or iodo. The terms "haloalkyl" and "haloalkoxy" include alkyl, alkenyl, alkynyl and alkoxy structures that are substituted with one or more halo groups or with combinations thereof. For example, the term "fluoroalkyl" includes a haloalkyl group in which the halo is fluorine.

"Aryl" refers to an aromatic radical with six to ten ring atoms which has at least one ring having a conjugated pi electron system which is carbocyclic (e.g., phenyl, fluorenyl, and naphthyl). The term includes monocyclic or fused-ring polycyclic (i.e., rings which share adjacent pairs of ring atoms) groups.

"Arylalkyl" or "aralkyl" as used herein refers to aryl-alkyl, wherein aryl and alkyl are defined herein. The "arylalkyl" moiety may be bound through the aryl or alkyl group.

"Heteroaryl" refers to a 5- to 18-membered aromatic radical (e.g., ($C_{5-13}$)heteroaryl) that includes one or more ring heteroatoms selected from nitrogen, oxygen and sulfur, and which may be a monocyclic, bicyclic, tricyclic or tetracyclic ring system. Whenever it appears herein, a numerical range such as "5 to 18" refers to each integer in the given range—e.g., "5 to 18 ring atoms" means that the heteroaryl group may contain 5 ring atoms, 6 ring atoms, etc., up to and including 18 ring atoms. Bivalent radicals derived from univalent heteroaryl radicals whose names end in "-yl" by removal of one hydrogen atom from the atom with the free valence are named by adding "-idene" to the name of the corresponding univalent radical—e.g., a pyridyl group with two points of attachment is a pyridylidene. An N-containing "heteroaryl" moiety refers to an aromatic group in which at least one of the skeletal atoms of the ring is a nitrogen atom. The polycyclic heteroaryl group may be fused or non-fused. The heteroatom(s) in the heteroaryl radical are optionally oxidized. One or more nitrogen atoms, if present, are optionally quaternized. The heteroaryl may be attached to the rest of the molecule through any atom of the ring(s). Examples of heteroaryls include, but are not limited to, azepinyl, acridinyl, benzimidazolyl, benzindolyl, 1,3-benzodioxolyl, benzofuranyl, benzooxazolyl, benzo[d]thiazolyl, benzothiadiazolyl, benzo[b][1,4]dioxepinyl, benzo [b][1,4]oxazinyl, 1,4-benzodioxanyl, benzonaphthofuranyl, benzoxazolyl, benzodioxolyl, benzodioxinyl, benzoxazolyl, benzopyranyl, benzopyranonyl, benzofuranyl, benzofuranonyl, benzofurazanyl, benzothiazolyl, benzothienyl(benzothiophenyl), benzothieno[3,2-d]pyrimidinyl, benzotriazolyl, benzo[4,6]imidazo[1,2-a]pyridinyl, carbazolyl, cinnolinyl, cyclopenta[d]pyrimidinyl, 6,7-dihydro-5H-cyclopenta[4,5] thieno[2,3-d]pyrimidinyl, 5,6-dihydrobenzo[h]quinazolinyl, 5,6-dihydrobenzo[h]cinnolinyl, 6,7-dihydro-5H-benzo[6,7] cyclohepta[1,2-c]pyridazinyl, dibenzofuranyl, dibenzothiophenyl, furanyl, furazanyl, furanonyl, furo[3,2-c]pyridinyl, 5,6,7,8,9,10-hexahydrocycloocta[d]pyrimidinyl, 5,6,7,8,9, 10-hexahydrocycloocta[d]pyridazinyl, 5,6,7,8,9,10-hexahydrocycloocta[d]pyridinyl, isothiazolyl, imidazolyl, indazolyl, indolyl, indazolyl, isoindolyl, indolinyl, isoindolinyl, isoquinolyl, indolizinyl, isoxazolyl, 5,8-methano-5,6,7,8-tetrahydroquinazolinyl, naphthyridinyl, 1,6-naphthyridinonyl, oxadiazolyl, 2-oxoazepinyl, oxazolyl, oxiranyl, 5,6,6a,7,8,9,10,10a-octahydrobenzo[h]quinazolinyl, 1-phenyl-1H-pyrrolyl, phenazinyl, phenothiazinyl, phenoxazinyl, phthalazinyl, pteridinyl, purinyl, pyranyl, pyrrolyl, pyrazolyl, pyrazolo[3,4-d]pyrimidinyl, pyridinyl, pyrido[3,2-d]pyrimidinyl, pyrido[3,4-d]pyrimidinyl, pyrazinyl, pyrimidinyl, pyridazinyl, pyrrolyl, quinazolinyl, quinoxalinyl, quinolinyl, isoquinolinyl, tetrahydroquinolinyl, 5,6,7,8-tetrahydroquinazolinyl, 5,6,7,8-tetrahydrobenzo[4,5]thieno[2,3-d]pyrimidinyl, 6,7,8,9-tetrahydro-5H-cyclohepta[4,5]thieno[2,3-d]pyrimidinyl, 5,6,7,8-tetrahydropyrido[4,5-c]pyridazinyl, thiazolyl, thiadiazolyl, thiapyranyl, triazolyl, tetrazolyl, triazinyl, thieno[2,3-d]pyrimidinyl, thieno[3,2-d]pyrimidinyl, thieno[2,3-c]pyridinyl, and thiophenyl (i.e. thienyl). Unless stated otherwise specifically in the specification, a heteroaryl moiety is optionally substituted by one or more substituents which are independently: alkyl, heteroalkyl, alkenyl, alkynyl, cycloalkyl, heterocycloalkyl, aryl, arylalkyl, heteroaryl, heteroarylalkyl, hydroxy, halo, cyano, nitro, oxo, thioxo, trimethylsilanyl, —OR$^a$, —SR$^a$, —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, N(R$^a$)C(NR$^a$)N(R$^a$)$_2$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, arylalkyl, heterocycloalkyl, heterocycloalkylalkyl, heteroaryl or heteroarylalkyl.

"Heteroarylalkyl" as used herein refers to heteroarylalkyl, wherein heteroaryl and alkyl are defined herein. The "heteroarylalkyl" moiety may be bound through the heteroaryl or alkyl group.

"Ester" refers to a chemical radical of formula —COOR$^e$, where R$^e$ includes, but is not limited to, alkyl, alkenyl, alkynyl, alkyl, alkenyl, alkynyl, cycloalkyl, cycloalkenyl, heterocyclyl, aryl, heteroaryl, arylalkyl, and heteroaylralkyl. The procedures and specific groups to make esters are known to those of skill in the art and can readily be found in seminal sources such as Greene and Wuts, Protective Groups in Organic Synthesis, 3$^{rd}$ Ed., John Wiley & Sons, New York, N.Y., 1999, which is incorporated herein by reference in its entirety. Unless stated otherwise specifically in the specification, an ester group is optionally substituted by one or more substituents which are described herein as suitable substitution groups.

The term "heteroalkyl" refers to an alkyl comprising at least one heteroatom in the backbone of the alkyl group as defined herein. In some embodiments, the heteroalkyl contains at least one oxygen, sulfur, or nitrogen heteroatom. In some preferred embodiments, the heteroalkyl contains at least one oxygen atom, for example one, two, three, four, or five oxygen atoms. An alkoxy group is one example of a heteroalkyl group containing one oxygen atom. In other preferred embodiments, the heteroalkyl contains at least one sulfur atom, for example one, two, three, four, or five sulfur atoms. In other preferred embodiments, the heteroalkyl contains at least one nitrogen atom, for example one, two, three, four, or five nitrogen atoms.

The term "alkoxy" refers to the group —O-alkyl. In some preferred embodiments, the alkoxy group contains from 1 to 12 carbon atoms of a straight, branched, cyclic configuration and combinations thereof attached to the parent structure through an oxygen. Whenever it appears herein, a numerical range such as "1 to 12" refers to each integer in the given range—e.g., "1 to 12 carbon atoms" means that group may consist of 3 carbon atoms, 4 carbon atoms, 5 carbon atoms, etc., up to and including 12 carbon atoms. Examples of alkoxy include, but are not limited to, methoxy, ethoxy, propoxy, isopropoxy, cyclopropyloxy and cyclohexyloxy.

The term "alkylene" or "alk" refers to an aliphatic linker having from, e.g., 1 to 20 carbon atoms, for example, the term "C$_{1-6}$alk" refers to an aliphatic linker having 1, 2, 3, 4, 5, or 6 carbon atoms and includes, for example, —CH$_2$—, —CH(CH$_3$)—, —CH(CH$_3$)—CH$_2$—, and —C(CH$_3$)$_2$—. The term "—C$_0$alk-" refers to a bond. An alkylene moiety can be optionally substituted with one, two, or three substituents selected from halo (F, Cl, Br, or I, preferably F), —OH, —OC$_{1-6}$alkyl, —CN, —NH$_2$, —NH(C$_{1-6}$alkyl), —NH(C$_{1-6}$alkyl)$_2$, or heterocycloalkyl such as pyrrolidinyl, piperidinyl, morpholinyl, thiomorpholinyl, piperazinyl, azepanyl, aziridinyl, azetidinyl, imidazolidinyl, pyrazolidinyl, oxazepanyl, or quinuclidinyl.

The term "heterocycloalkyl" refers to any three to ten membered or four to ten membered monocyclic or bicyclic, saturated ring structure containing at least one heteroatom selected from the group consisting of O, N and S. The heterocycloalkyl group may be attached at any heteroatom or carbon atom of the ring such that the result is a stable structure. Examples of suitable heterocycloalkyl groups include, but are not limited to, azepanyl, aziridinyl, azetidinyl, pyrrolidinyl, dioxolanyl, imidazolidinyl, pyrazolidinyl, piperazinyl, piperidinyl, dioxanyl, morpholinyl, dithianyl, thiomorpholinyl, oxazepanyl, oxiranyl, oxetanyl, quinuclidinyl, tetrahydrofuranyl, tetrahydropyranyl, piperazinyl, and the like.

"Heterocycloalkylalkyl" as used herein refers to heterocycloalkyl-alkyl, wherein heterocycloalkyl and alkyl are defined herein. The "heterocycloalkylalkyl" moiety may be bound through the heterocycloalkyl or alkyl group.

"Isomers" are different compounds that have the same molecular formula. "Stereoisomers" are isomers that differ only in the way the atoms are arranged in space—i.e., having a different stereochemical configuration. "Enantiomers" are a pair of stereoisomers that are non-superimposable mirror images of each other. A 1:1 mixture of a pair of enantiomers is a "racemic" mixture. The term "(±)" is used to designate a racemic mixture where appropriate. "Diastereoisomers" are stereoisomers that have at least two asymmetric atoms, but which are not mirror-images of each other. The absolute stereochemistry is specified according to the Cahn-Ingold-Prelog R—S system. When a compound is a pure enantiomer the stereochemistry at each chiral carbon can be specified by either (R) or (S). Resolved compounds whose absolute configuration is unknown can be designated (+) or (−) depending on the direction (dextro- or levorotatory) which they rotate plane polarized light at the wavelength of the sodium D line. Certain of the compounds described herein contain one or more asymmetric centers and can thus give rise to enantiomers, diastereomers, and other stereoisomeric forms that can be defined, in terms of absolute stereochemistry, as (R) or (S). The present chemical entities, pharmaceutical compositions and methods are meant to include all such possible isomers, including racemic mixtures, optically pure forms and intermediate mixtures. Optically active (R)- and (S)-isomers can be prepared using chiral synthons or chiral reagents, or resolved using conventional techniques. When the compounds described herein contain olefinic double bonds or other centers of geometric asymmetry, and unless specified otherwise, it is intended that the compounds include both E and Z geometric isomers.

"Enantiomeric purity" as used herein refers to the relative amounts, expressed as a percentage, of the presence of a specific enantiomer relative to the other enantiomer. For example, if a compound, which may potentially have an (R)- or an (S)-isomeric configuration, is present as a racemic mixture, the enantiomeric purity is about 50% with respect to either the (R)- or (S)-isomer. If that compound has one isomeric form predominant over the other, for example, 80% (S)-isomer and 20% (R)-isomer, the enantiomeric purity of the compound with respect to the (S)-isomeric form is 80%. The enantiomeric purity of a compound can be determined in a number of ways known in the art, including but not limited to chromatography using a chiral support, polarimetric measurement of the rotation of polarized light, nuclear magnetic resonance spectroscopy using chiral shift reagents which include but are not limited to lanthanide containing chiral complexes or Pirkle's reagents, or derivatization of a compounds using a chiral compound such as Mosher's acid followed by chromatography or nuclear magnetic resonance spectroscopy.

In preferred embodiments, the enantiomerically enriched composition has a higher potency with respect to therapeutic utility per unit mass than does the racemic mixture of that composition. Enantiomers can be isolated from mixtures by methods known to those skilled in the art, including chiral high pressure liquid chromatography (HPLC) and the formation and crystallization of chiral salts; or preferred enantiomers can be prepared by asymmetric syntheses. See, for example, Jacques, et al., Enantiomers, Racemates and Resolutions, Wiley Interscience, New York, 1981; Eliel, Stereochemistry of Carbon Compounds, McGraw-Hill, N.Y., 1962; and Eliel and Wilen, Stereochemistry of Organic Compounds, Wiley-Interscience, New York, 1994.

The terms "enantiomerically enriched" and "non-racemic," as used herein, refer to compositions in which the percent by weight of one enantiomer is greater than the amount of that one enantiomer in a control mixture of the racemic composition (e.g., greater than 1:1 by weight). For example, an enantiomerically enriched preparation of the (S)-enantiomer, means a preparation of the compound having greater than 50% by weight of the (S)-enantiomer relative to the (R)-enantiomer, such as at least 75% by weight, or such as at least 80% by weight. In some embodiments, the enrichment can be significantly greater than 80% by weight, providing a "substantially enantiomerically enriched" or a "substantially non-racemic" preparation, which refers to preparations of compositions which have at least 85% by weight of one enantiomer relative to other enantiomer, such as at least 90% by weight, or such as at least 95% by weight. The terms "enantiomerically pure" or "substantially enantiomerically pure" refers to a composition that comprises at least 98% of a single enantiomer and less than 2% of the opposite enantiomer.

"Pharmaceutically acceptable" means approved or approvable by a regulatory agency of the Federal or a state government or the corresponding agency in countries other than the United States, or that is listed in the U.S. Pharmacopoeia or other generally recognized pharmacopoeia for use in animals, and more particularly, in humans.

"Pharmaceutically acceptable salt" refers to a salt of a compound of the disclosure that is pharmaceutically acceptable and that possesses the desired pharmacological activity of the parent compound. In particular, such salts are non-toxic may be inorganic or organic acid addition salts and base addition salts. Specifically, such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, N-methylglucamine and the like. Salts further include, by way of example only, sodium, potassium, calcium, magnesium, ammonium, tetraalkylammonium, and the like; and when the compound contains a basic functionality, salts of nontoxic organic or inorganic acids, such as hydrochloride, hydrobromide, tartrate, mesylate, acetate, maleate, oxalate and the like.

"Pharmaceutically acceptable vehicle" refers to a diluent, adjuvant, excipient or carrier with which a compound of the disclosure is administered. A "pharmaceutically acceptable excipient" refers to a substance that is non-toxic, biologically tolerable, and otherwise biologically suitable for administration to a subject, such as an inert substance, added to a pharmacological composition or otherwise used as a vehicle, carrier, or diluent to facilitate administration of an agent and that is compatible therewith. Examples of excipients include calcium carbonate, calcium phosphate, various sugars and types of starch, cellulose derivatives, gelatin, vegetable oils, and polyethylene glycols.

"Subject" as used herein refers to a mammalian animal. In one embodiment, the patient or subject is a human. In another embodiment, the patient or subject is a veterinary or farm animal, a domestic animal or pet, or animal normally used for clinical research. In further embodiments, the subject is a canine, feline, or primate The terms "human," "patient," and "subject" are used interchangeably herein.

"Treating" or "treatment" of any disease or disorder refers, in one embodiment, to ameliorating the disease or disorder (i.e., arresting or reducing the development of the disease or at least one of the clinical symptoms thereof). In another embodiment "treating" or "treatment" refers to ameliorating at least one physical parameter, which may not be discernible by the subject. In yet another embodiment, "treating" or "treatment" refers to modulating the disease or disorder, either physically, (e.g., stabilization of a discernible symptom), physiologically, (e.g., stabilization of a physical parameter), or both. In yet another embodiment, "treating" or "treatment" refers to delaying the onset of the disease or disorder.

Compounds of Formula (I) and (II)
The present disclosure is directed to compounds of Formula (I) or Formula (II):
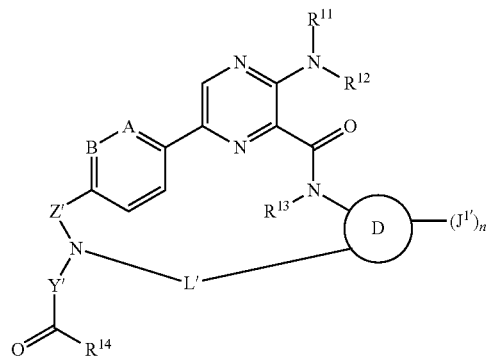
(I)
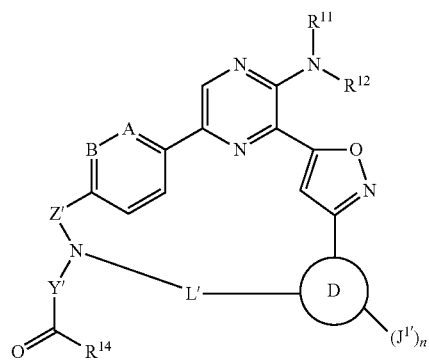
(II)
Preferred embodiments of Formula (I) include compounds of Formula (I-A)-(I-H) and (IK):
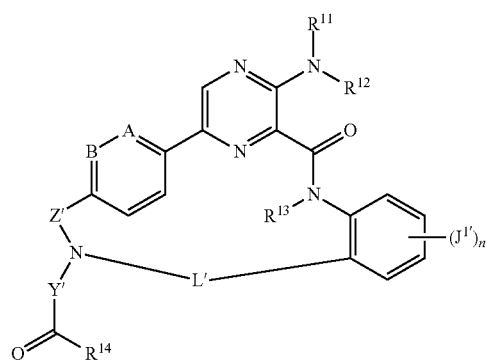
(I-A)
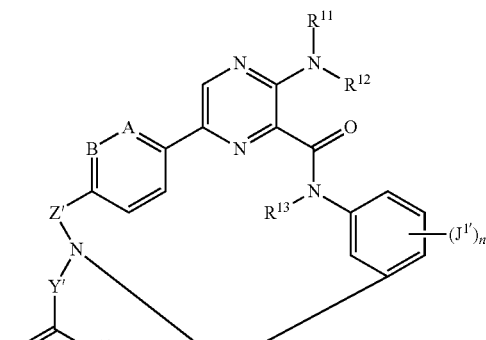
(I-B)
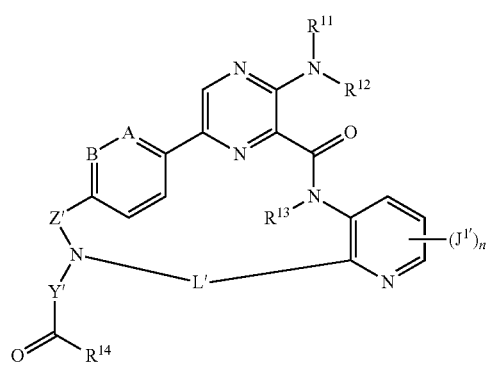
(I-C)
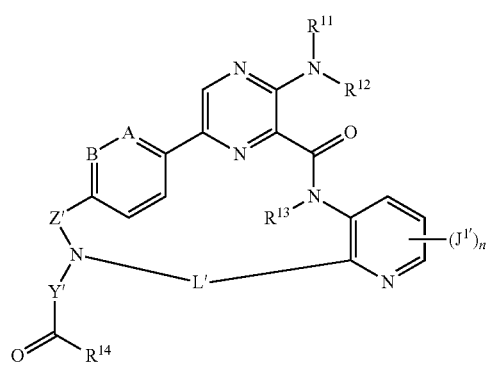
(I-D)
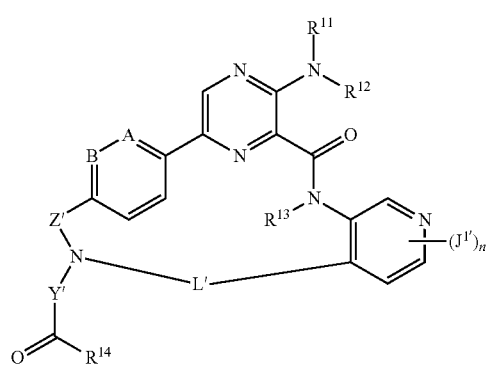
(I-E)

(I-F)
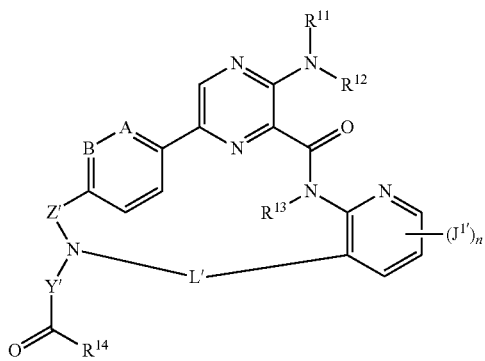
(I-G)
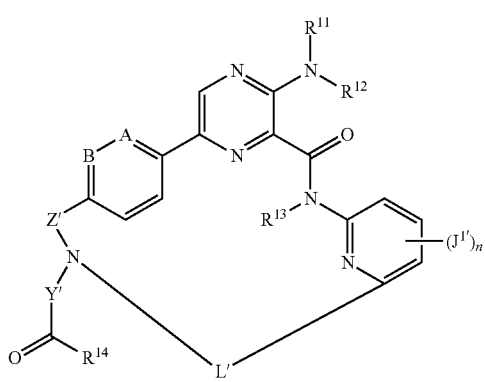
(I-H)
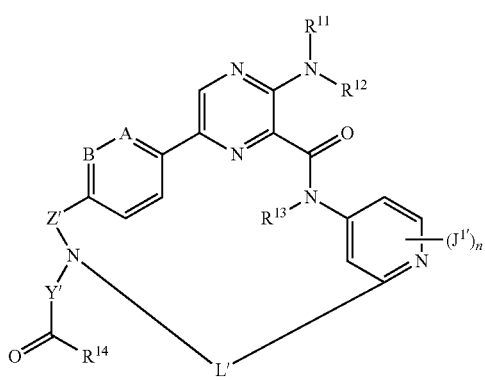
(I-J)
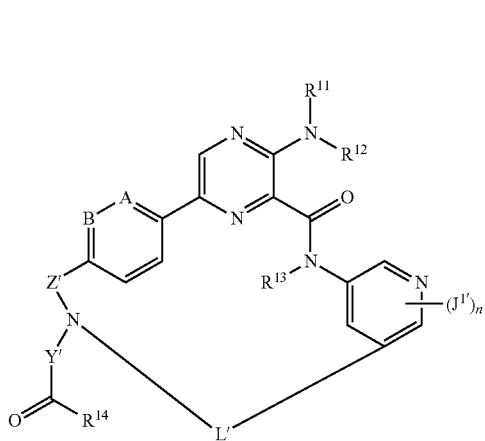
(I-K)
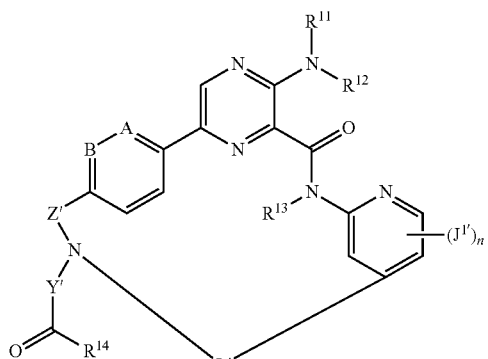
Preferred embodiments of Formula (II) include compounds of Formula (II-A)-(II-H) and (II-K):
(II-A)
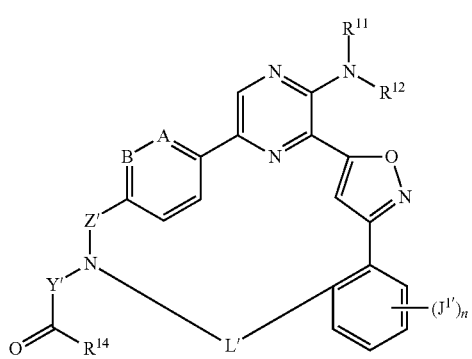
(II-B)
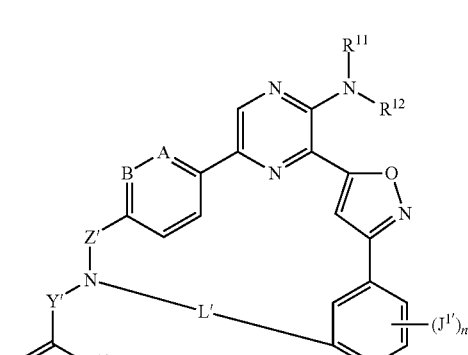
(II-C)
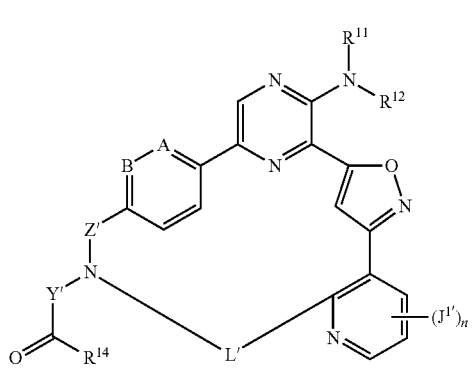

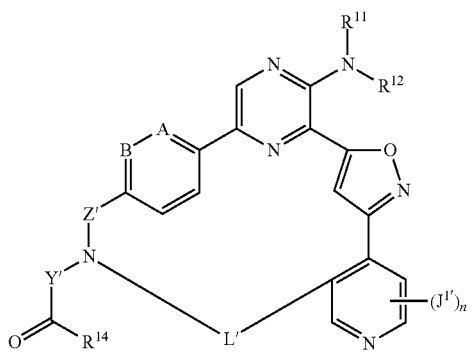
(II-D)
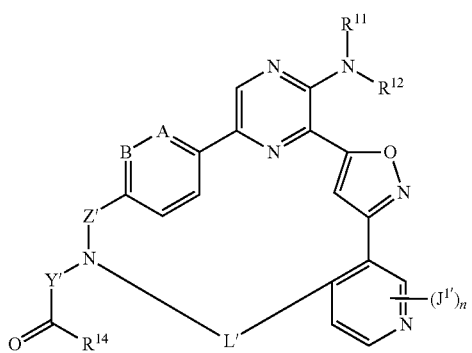
(II-E)
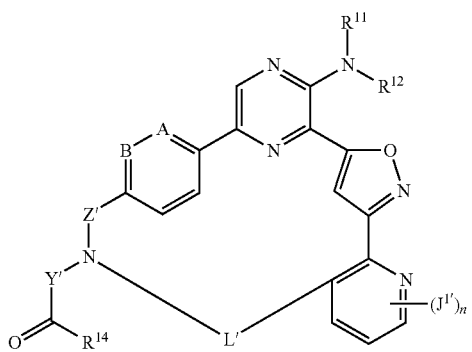
(II-F)
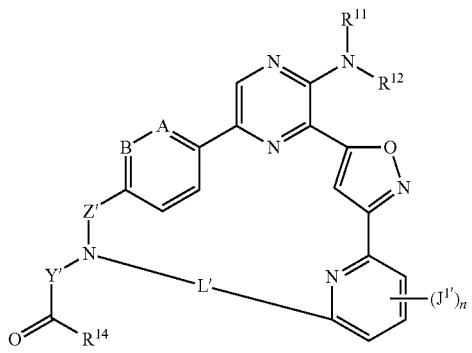
(II-G)
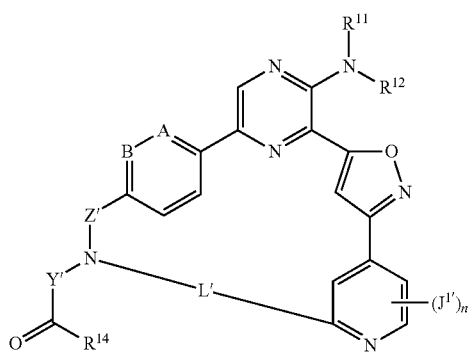
(II-H)
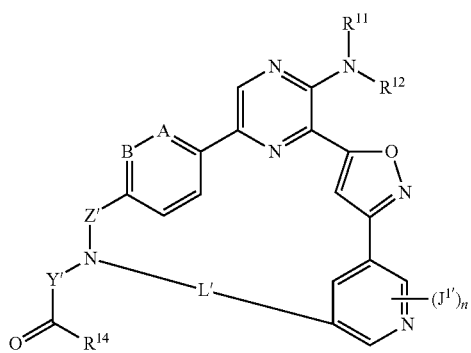
(II-J)
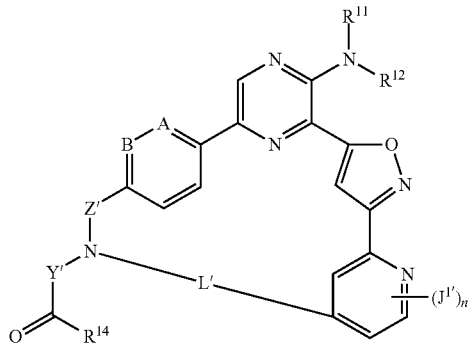
(II-K)
Further preferred compounds of Formula (I) include compounds of Formula (I-L)-(I-P):
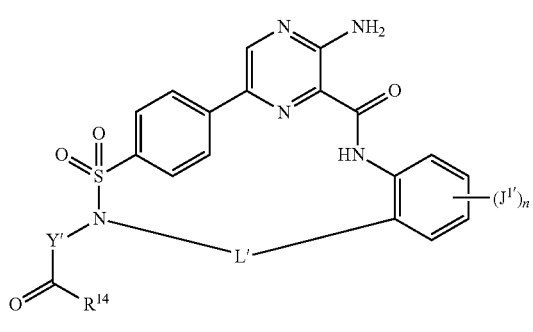
(I-L)

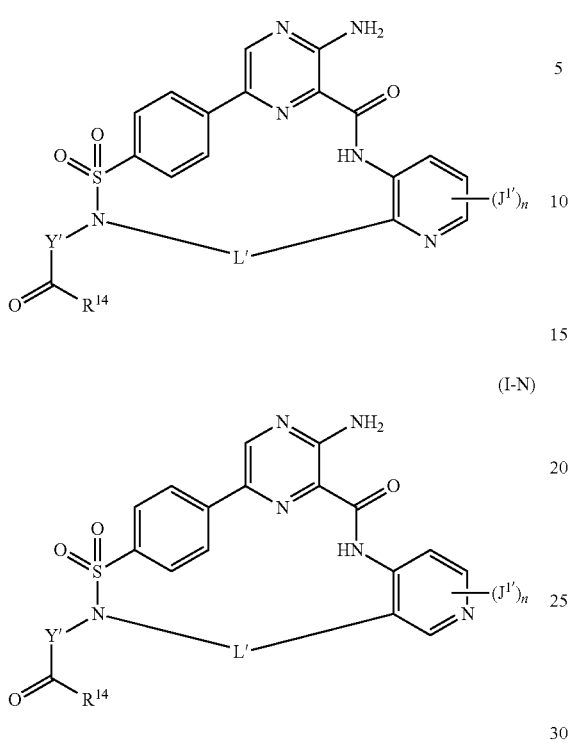
(I-M)
(I-N)
(I-O)
(I-P)
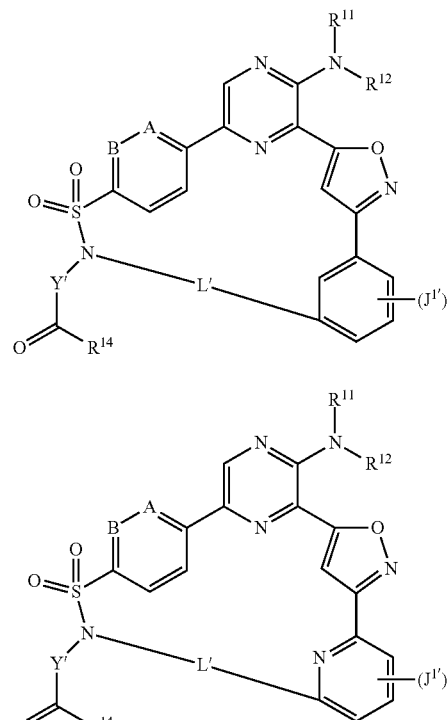
(II-L)
(II-M)
(II-N)
(II-O)
Other preferred compounds of Formula (II) include compounds of Formula (II-L)-(II-P):

(II-P)
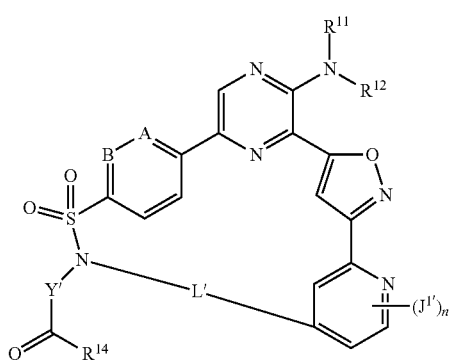
Yet further preferred compounds of Formula (I) include compounds of Formula (I-Q)-(I-U):
(I-Q)
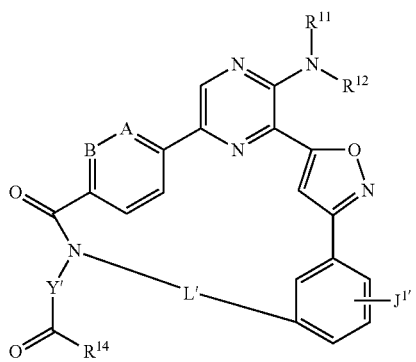
(I-R)
(I-S)
(I-T)
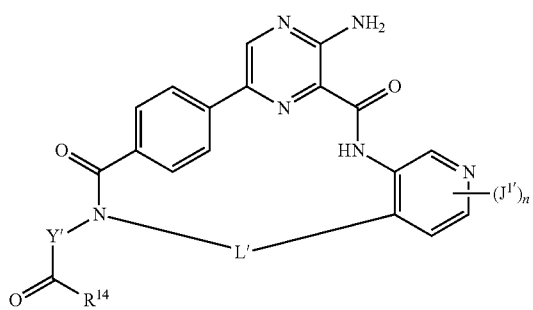
(I-U)
Still other preferred compounds of Formula (II) include compounds of Formula (II-Q)-(II-U):
(II-Q)
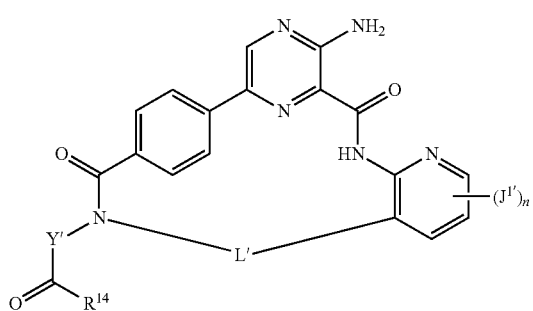
(II-R)
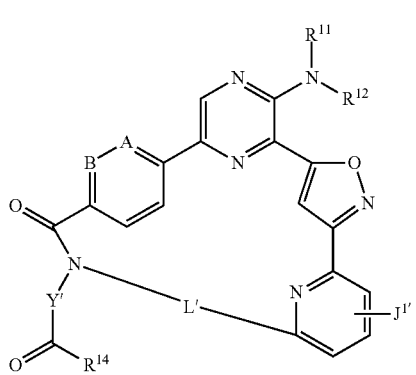

-continued
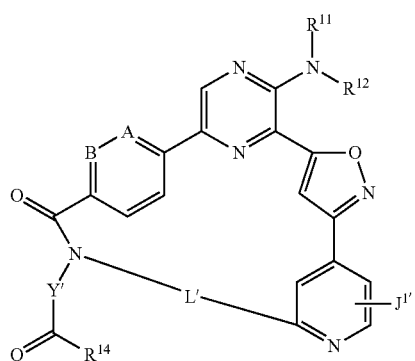
(II-S)
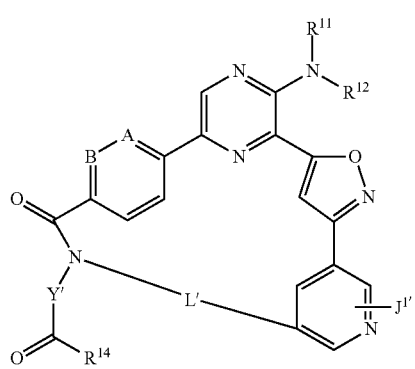
(II-T)
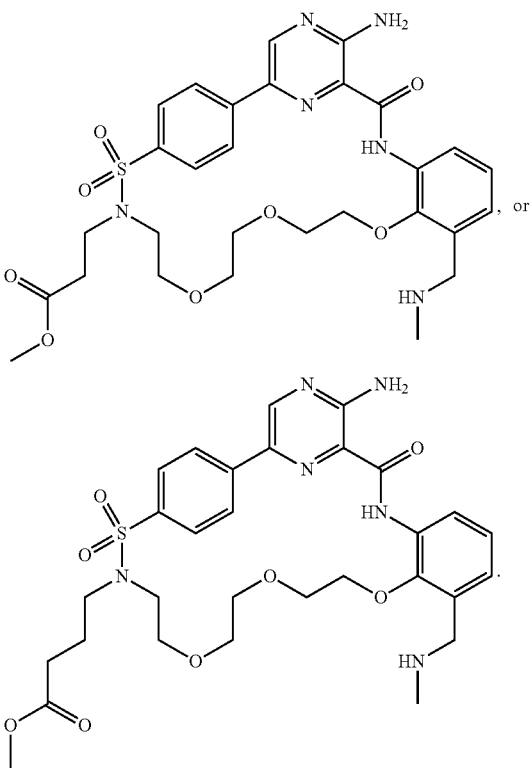
-continued
Further preferred compounds of Formula (I) include:
(II-U)
Other preferred compounds of Formula (I) include:
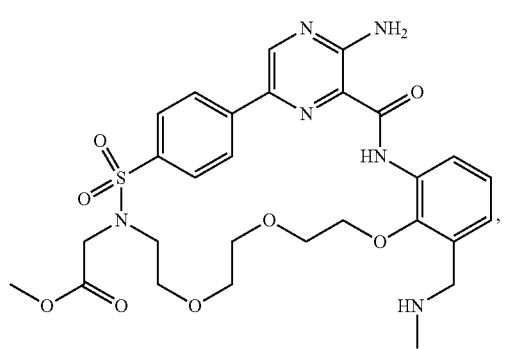
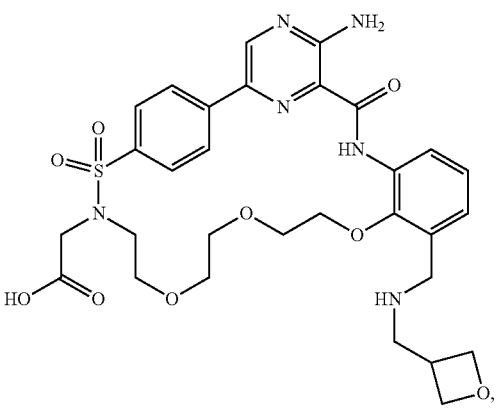

23
-continued
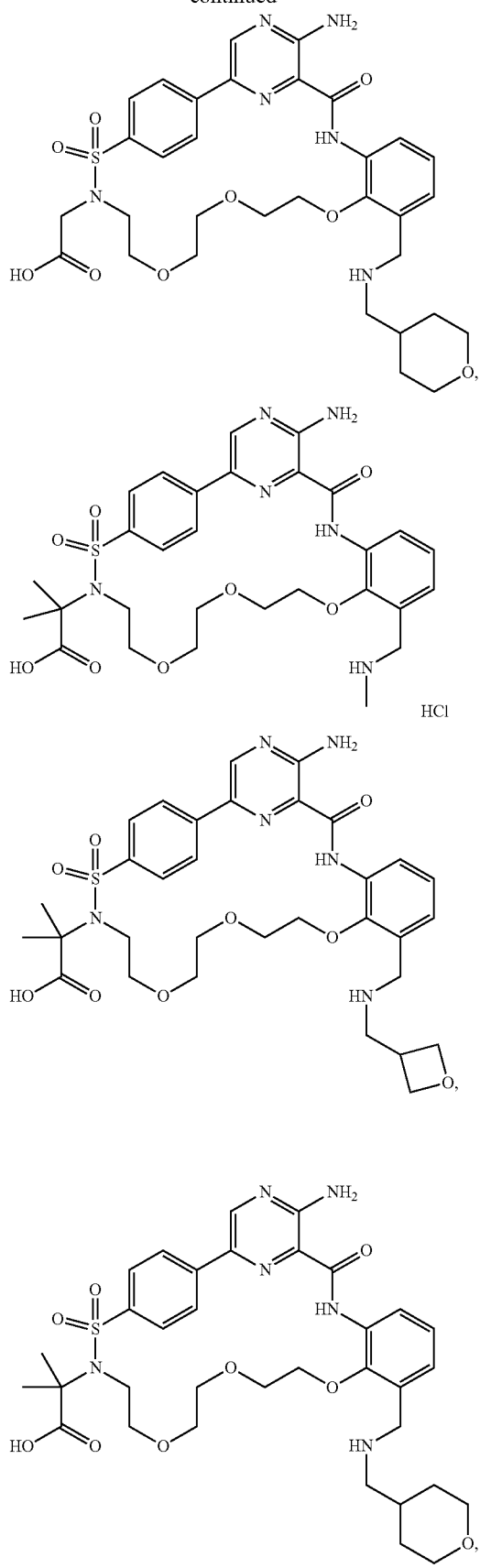
24
-continued
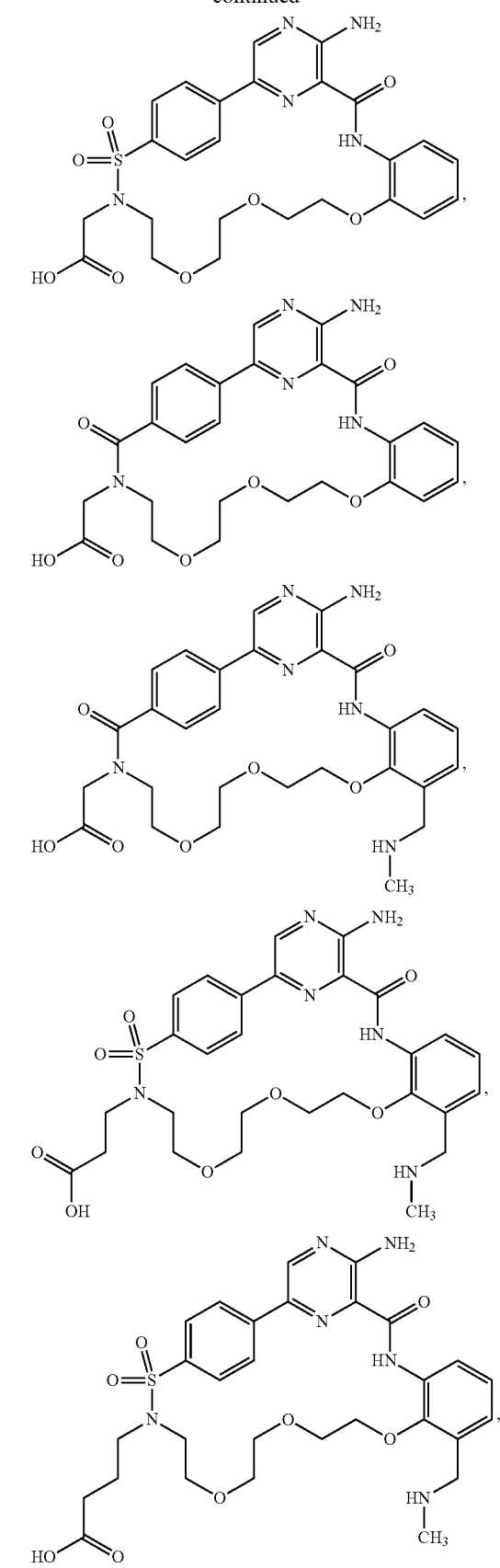

-continued
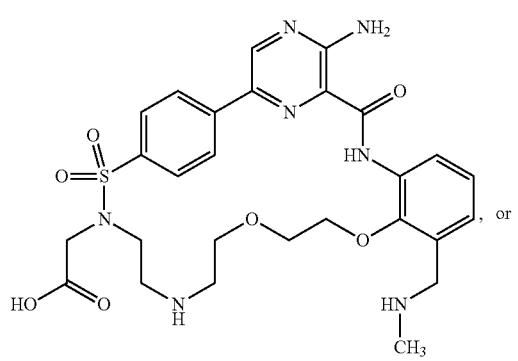
Other preferred compounds of Formula (I) include:
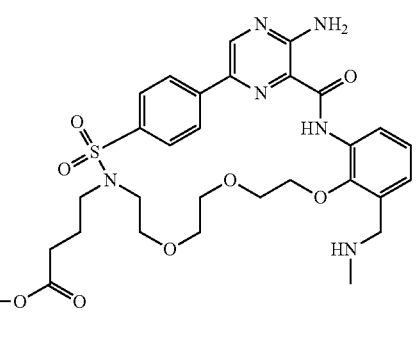
or
Other preferred compounds of Formula (I) are:
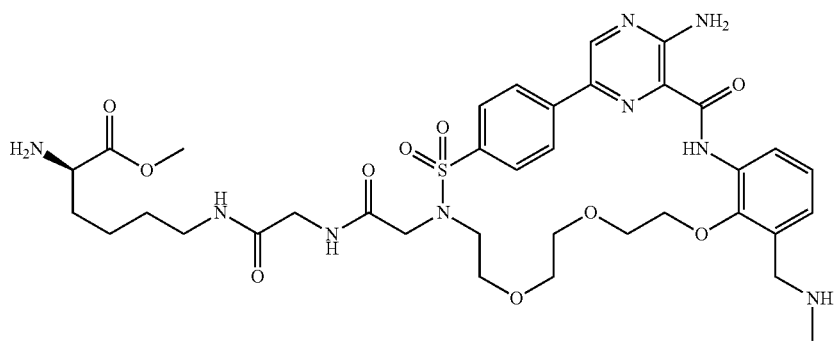
ATRN 6

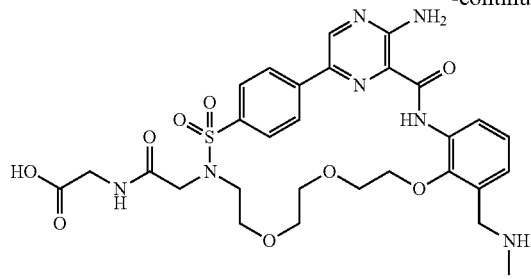
ATRN 6-A

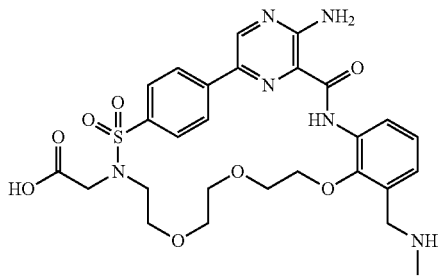
ATRN 6-B

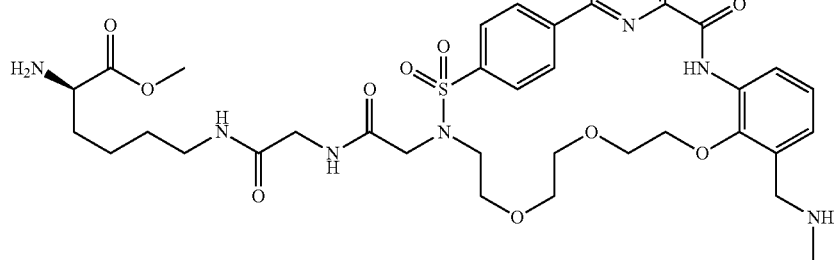
ATRN 7

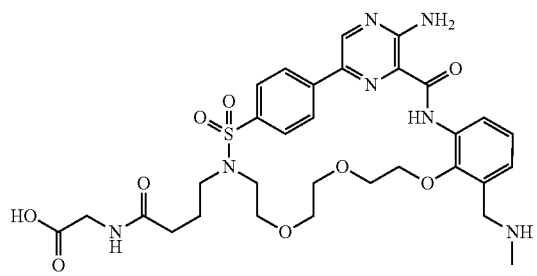
ATRN 7-A

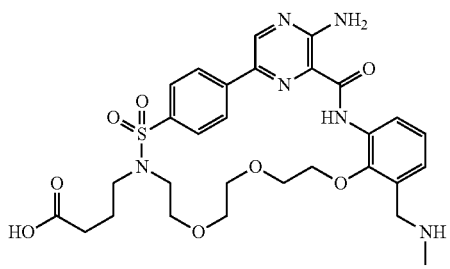
ATRN 7-B

According to the disclosure, A is CH, C—$C_{1-6}$alkyl, C—$C_{1-6}$haloalkyl, or N. In some aspects, A is CH. In other aspects, A is C—$C_{1-6}$alkyl. In further aspects, A is C—$C_{1-6}$haloalkyl. In still other aspects, A is N.

Also according to the disclosure, B is CH, C—$C_{1-6}$alkyl, C—$C_{1-6}$haloalkyl, or N. In some aspects, B is CH. In other aspects, B is C—$C_{1-6}$alkyl. In further aspects, B is C—$C_{1-6}$haloalkyl. In still other aspects, B is N.

In preferred embodiments, A is CH and B is CH. In other embodiments, A is N and B is CH. In yet other embodiments, A is CH and B is N. In still other embodiments, A is N and B is N. In further embodiments, one or both of A an B is C—$C_{1-6}$alkyl. In other embodiments, one or both of A and B is C—$CHCH_3$. In still further embodiments, one or both of A and B is C—$C_{1-6}$fluoroalkyl. In yet other embodiments, one or both of A and B is C—$CH_2F$ or C—$CF_3$.

According to the disclosure, D is a ring, preferably a 6-membered ring, preferably an aryl ring. In some embodiments, ring D is phenylene. In other embodiments, ring D is pyridylene. In some aspects, ring D is

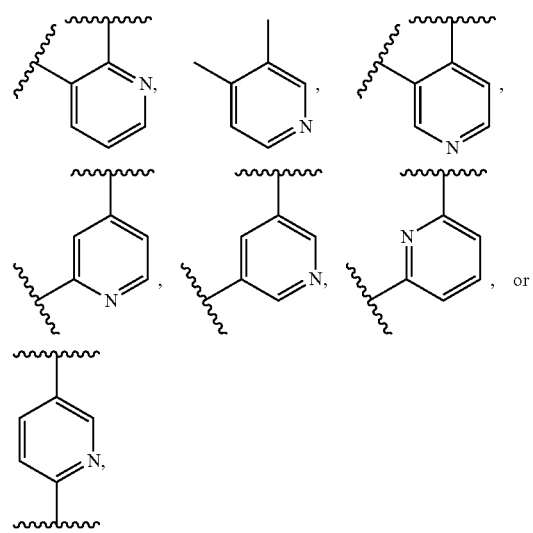

where ∼∼∼ signifies the point of attachment to the L' moiety, $NR^{13}$ of Formula (I), or oxazole of Formula (II).

According to the disclosure, $R^{11}$ is H or $C_{1-6}$alkyl. In some aspects, $R^{11}$ is H. In other aspects, $R^{11}$ is $C_{1-6}$alkyl, for example, methyl, ethyl, propyl, isopropyl, butyl, isobutyl, tert-butyl, pentyl, or hexyl.

According to the disclosure, $R^{12}$ is H or $C_{1-6}$alkyl. In some aspects, $R^{12}$ is H. In other aspects, $R^{12}$ is $C_{1-6}$alkyl, for example, methyl, ethyl, propyl, isopropyl, butyl, isobutyl, tert-butyl, pentyl, or hexyl.

According to the disclosure, $R^{13}$ is H or $C_{1-6}$alkyl. In some aspects, $R^{13}$ is H. In other aspects, $R^{13}$ is $C_{1-6}$alkyl, for example, methyl, ethyl, propyl, isopropyl, butyl, isobutyl, tert-butyl, pentyl, or hexyl.

In preferred aspects, each of $R^{11}$, $R^{12}$, and $R^{13}$ is H. In some aspects, $R^{11}$ is H and $R^{12}$ and $R^{13}$ are each independently $C_{1-6}$alkyl. In some aspects, $R^{12}$ is H and $R^{11}$ and $R^{13}$ are each independently $C_{1-6}$alkyl. In some aspects, $R^{13}$ is H and $R^{11}$ and $R^{12}$ are each independently $C_{1-6}$alkyl. In other aspects, $R^{11}$ and $R^{12}$ are each H and $R^{13}$ is $C_{1-6}$alkyl. In other aspects, $R^{11}$ and $R^{13}$ are each H and $R^{12}$ is $C_{1-6}$alkyl. In other aspects, $R^{12}$ and $R^{13}$ are each H and $R^{11}$ is $C_{1-6}$alkyl.

According to the disclosure, Z' is —$SO_2$— or —C(O)—. In some aspects, Z' is —$SO_2$—. In other aspects, Z' is —C(O)—.

According to the disclosure, Y' is an alkylene (i.e., an "alk"), for example, a $C_1$-$C_{12}$alkylene, preferably a $C_{1-6}$alkylene. In preferred aspects, Y' is $C_1$alkylene, $C_2$alkylene, $C_3$alkylene, $C_4$alkylene, $C_4$alkylene, $C_5$alkylene, $C_6$alkylene, $C_7$alkylene, $C_8$alkylene, $C_9$alkylene, $C_{10}$alkylene, $C_{11}$alkylene, or $C_{12}$alkylene. In some embodiments, Y' is $C_1$alkylene. In other embodiments, Y' is $C_2$alkylene. In yet other embodiments, Y' is $C_3$alkylene. In still other embodiments, Y' is $C_4$alkylene.

According to the disclosure, one or more $J^{1'}$ are present on the D ring. In some embodiments, the D-ring contains "n" (i.e., an integer that is 1, 2, or 3) independently selected $J^{1'}$ substituents. Each $J^{1'}$ substituent is bound to a carbon-atom of the D-ring. In some embodiments, n is 1 or 2. In other embodiments, n is 1. In further embodiments, n is 2. Each $J^{1'}$ is selected from H, optionally substituted —$C_{1-6}$alkyl, optionally substituted $C_{1-6}$haloalkyl, optionally substituted —$C_{1-6}$alkoxy, $NH_2$, NH-(optionally substituted $C_{1-6}$alkyl), N-(optionally substituted $C_{1-6}$alkyl)(optionally substituted $C_{1-6}$alkyl), —$C_{1-6}$alk-NH-(optionally substituted $C_{1-6}$alkyl), or —$C_{1-6}$alk-NH—$C_{0-6}$alk-(optionally substituted $C_{3-6}$heterocycloalkyl).

In some aspects, $J^{1'}$ is H.

In other aspects, $J^{1'}$ is —$C_{1-6}$alkyl, for example methyl, ethyl, propyl, isopropyl, butyl, isobutyl, tert-butyl, pentyl, or hexyl. In some embodiments, wherein $J^{1'}$ is substituted —$C_{1-6}$alkyl, the $C_{1-6}$alkyl is substituted with one, two, or three substituents independently selected from halo (F, Cl, Br, or I, preferably F), —OH, —$OC_{1-6}$alkyl, and —CN.

In further aspects, $J^{1'}$ is optionally substituted —$C_{1-6}$haloalkyl, where one or more hydrogen atom is replaced with a halogen. Preferably, the —$C_{1-6}$haloallkyl is a —$C_{1-6}$fluoroalkyl, for example, fluorinated methyl ($CF_3$), fluorinated ethyl, fluorinated propyl, fluorinated isopropyl, fluorinated butyl, fluorinated isobutyl, flyrinated tert0butyl, florinated pentyl, or fluorinated hexyl. In some embodiments wherein $J^{1'}$ is —$C_{1-6}$haloalkyl, the $C_{1-6}$haloalkyl is substituted with one, two, or three substituents independently selected from —OH, —$C_{1-6}$alkyl, —$OC_{1-6}$alkyl, and —CN.

In yet other aspects, $J^{1'}$ is optionally substituted —$C_{1-6}$alkoxy, for example, methoxy, ethoxy, propoxy, isopropoxy, butoxy, isobutoxy, tert-butoxy, pentoy, or hexoxy. In some embodiments, one or more carbon atom of the $C_{1-6}$alkoxy is substituted with one, two, or three substituents independently selected from halo (F, Cl, Br, or I, preferably F), —OH, —$C_{1-6}$alkyl, and —CN.

In still other aspects, $J^{1'}$ is $NH_2$.

In other aspects, $J^{1'}$ is NH-(optionally substituted $C_{1-6}$alkyl), where $C_{1-6}$ alkyl is defined above. In some embodiments, $J^{1'}$ is —NH(methyl), —NH(ethyl), —NH(propyl), —NH(isopropyl), —NH(butyl), —NH(isobutyl), —NH(tert-butyl), —NH(pentyl), or —NH(hexyl).

In further aspects, $J^{1'}$ is N-(optionally substituted $C_{1-6}$alkyl)(optionally substituted $C_{1-6}$alkyl), where $C_{1-6}$alkyl is defined above and the $C_{1-6}$alkyl groups may be the same or different. In some embodiments, $J^{1'}$ is —N(methyl)$_2$, —N(ethyl)$_2$, N(methyl)(ethyl), —N(propyl)$_2$, —N(isopropyl)$_2$, —N(butyl)$_2$, —N(isobutyl)$_2$, —N(tert-butyl)$_2$, —N(pentyl)$_2$, or —N(hexyl)$_2$.

In other aspects, $J^{1'}$ is —$C_{1-6}$alk-NH—($C_{1-6}$alkyl) or —$C_{1-6}$alk-NH-(substituted $C_{1-6}$alkyl), for example, —$C_{1-6}$alk-NH—($C_{1-6}$alkyl), —$C_{1-5}$alk-NH—($C_{1-6}$alkyl), —$C_{1-4}$alk-NH—($C_{1-6}$alkyl), —$C_{1-3}$alk-NH—($C_{1-6}$alkyl), —$C_{1-2}$alk-NH—($C_{1-6}$alkyl), —$C_1$alk-NH—($C_{1-6}$alkyl), or —$C_0$alk-NH—($C_{1-6}$alkyl). In other aspects, $J^{1'}$ is —$C_{0-6}$alk-NH—($C_{1-5}$alkyl), for example, —$C_{1-6}$alk-NH—($C_{1-5}$alkyl), —$C_{0-6}$alk-NH—($C_{1-5}$alkyl), $C_{0-6}$alk-NH—($C_{1-4}$alkyl), $C_{0-6}$alk-NH—($C_{1-3}$alkyl), $C_{0-6}$alk-NH—($C_{1-2}$alkyl), or $C_{0-6}$alk-NH—($C_1$alkyl). In some embodiments wherein $J^{1'}$ is —$C_{1-6}$alk-NH—($C_{1-6}$alkyl) or —$C_{0-6}$alk-NH—($C_{1-6}$alkyl), the $C_{1-6}$alkyl is substituted with one, two, or three substituents independently selected from halo (F, Cl, Br, or I, preferably F), —OH, —$OC_{1-6}$alkyl, and —CN.

In some aspects, $J^{1'}$ is —$C_{1-6}$alk-NH—$C_{0-6}$alk-($C_{3-6}$heterocycloalkyl) or —$C_{1-6}$alk-NH—$C_{0-6}$alk-(substituted $C_{3-6}$heterocycloalkyl), for example, —$C_{1-6}$alk-NH—$C_{0-6}$alk-($C_{3-6}$heterocycloalkyl), —$C_{1-5}$alk-NH—$C_{0-6}$alk-($C_{3-6}$heterocycloalkyl), —$C_{1-4}$alk-NH—$C_{0-6}$alk-($C_{3-6}$heterocycloalkyl), —$C_{1-3}$alk-NH—$C_{0-6}$alk-($C_{3-6}$heterocycloalkyl), —$C_{1-2}$alk-NH—$C_{0-6}$alk-($C_{3-6}$heterocycloalkyl), —$C_1$alk-NH—$C_{0-6}$alk-($C_{3-6}$heterocycloalkyl), or —$C_0$alk-NH—$C_{0-6}$alk-($C_{3-6}$heterocycloalkyl). Alternatively, $J^{1'}$ is —$C_{0-6}$alk-NH—$C_{0-5}$alk-($C_{3-6}$heterocycloalkyl), —$C_{1-6}$alk-NH—$C_{0-4}$alk-($C_{3-6}$heterocycloalkyl), —$C_{1-6}$alk-NH—$C_{0-3}$alk-($C_{3-6}$heterocycloalkyl), —$C_{1-6}$alk-NH—$C_{0-2}$alk-($C_{3-6}$heterocycloalkyl), —$C_{1-6}$alk-NH—$C_{0-1}$alk-($C_{3-6}$heterocycloalkyl), or —$C_{1-6}$alk-NH—$C_0$alk-($C_{3-6}$heterocycloalkyl). In other embodiments, $J^{1'}$ is —$C_{1-6}$alk-NH—$C_{0-6}$alk-($C_{3-5}$heterocycloalkyl), —$C_{1-6}$alk-NH—$C_{0-6}$alk-($C_{3-4}$heterocycloalkyl), or $J^{1'}$ is —$C_{1-6}$alk-NH—$C_{0-6}$alk-($C_3$heterocycloalkyl). The heterocycloalkyl moiety can be attached to the compounds of Formula (III) or (IV) via a ring carbon. In those embodiments incorporating a nitrogen-containing heterocycloalkyl, the heterocycloalkyl moiety can be attached via a ring carbon atom or a ring nitrogen atom. Preferred heterocycloalkyl moieties include oxetanyl and tetrahydropyranyl. In some embodiments wherein $J^{1'}$ is —$C_{1-6}$alk-NH—$C_{0-6}$alk-($C_{3-6}$heterocycloalkyl), the heterocycloalkyl is substituted with one, two, or three substituents independently selected from halo (F, Cl, Br, or I, preferably F), —OH, —$OC_{1-6}$alkyl, and —CN.

According to the disclosure, L' is a linking group, preferably a 7 to 17-membered linking group, 7-membered linking group, 8-membered linking group, 9-membered linking group, or 10-membered linking group, for example, an alkylene (i.e., alk) optionally interrupted by 1, 2, 3, 4 or 5 heteroatom moieties independently selected from —O—, —NH—, —N($C_{1-6}$alkyl), —N(optionally substituted $C_{1-6}$alkyl), and —N($C_{1-6}$alkyl)-O(optionally substituted $C_{1-6}$alkyl). In those aspects wherein the alkylene is optionally interrupted by —N($C_{1-6}$alkyl) and/or —N($C_{1-6}$alkyl)-O ($C_{1-6}$alkyl), the $C_{1-6}$alkyl moieties can be optionally substituted with one, two, or three substituents independently selected from halo (F, Cl, Br, or I, preferably F), —OH, —O$C_{1-6}$alkyl, and —CN. In some aspects, L' is a 7 to 10-membered linking group comprising an alkylene optionally interrupted by three —O— heteroatom moieties. In other aspects, L' is a 7 to 10-membered linking group comprising an alkylene optionally interrupted by one —O— heteroatom moiety and one —NH—, —N($C_{1-6}$alkyl), —N(optionally substituted $C_{1-6}$alkyl), or —N($C_{1-6}$alkyl)-O (optionally substituted $C_{1-6}$alkyl) heteroatom moiety. In still other embodiments, L' is a 7 to 10-membered linking group comprising an alkylene optionally interrupted by two —O— heteroatom moieties and one —NH—, —N($C_{1-6}$alkyl), —N(optionally substituted $C_{1-6}$alkyl), or —N($C_{1-6}$alkyl)-O (optionally substituted $C_{1-6}$alkyl) heteroatom moiety. In yet further embodiments, L' is a 7 or 9-membered linking group comprising an alkylene interrupted by three —O— heteroatom moieties. In other embodiments, L' is a 7 or 9-membered linking group comprising an alkylene interrupted by one —O— heteroatom moiety and one —NH—, —N($C_{1-6}$alkyl), —N(optionally substituted $C_{1-6}$alkyl), or —N($C_{1-6}$alkyl)-O(optionally substituted $C_{1-6}$alkyl) heteroatom moiety. In still other embodiments, L' is a 7 or 9-membered linking group comprising an alkylene interrupted by two —O— heteroatom moieties and one —NH—, —N($C_{1-6}$alkyl), —N(optionally substituted $C_{1-6}$alkyl), or —N($C_{1-6}$alkyl)-O(optionally substituted $C_{1-6}$alkyl) heteroatom moiety. Preferred L' moieties include —($CH_2CH_2O)_3$—, —$CH_2$($CH_2CH_2O)_2$—, —CH($C_{1-6}$alkyl)($CH_2CH_2O)_3$— (e.g., —CH($CH_3$)($CH_2CH_2O)_3$—), —($CH_2CH_2CH_2O)_2$—, —$CH_2CH_2$NH($CH_2CH_2O)_2$, and —O—($CH_2CH_2O)_2$—.

According to the disclosure, $R^{14}$ is OH, —O$C_{1-30}$alkyl, —O-aryl, —O—$C_{1-30}$alk-C(O)$C_{1-30}$alkyl, —O—$C_{1-30}$alk-C(O)N($R^{15}$)($R^{16}$), —O-monosaccharide, —S—$C_{1-30}$alkyl, a peptidyl moiety, an isopeptide moiety, or a peptidyl-isopeptide moiety.

In some embodiments, $R^{14}$ is —OH, that is, the compound of the disclosure is a carboxylic acid derivative. Other aspects of the disclosure are directed to prodrugs of the carboxylic acid. Prodrugs for carboxylic acids are known in the art and include esters, ethers, peptides, and the like. In preferred embodiments, the carboxylic acid prodrugs encompass those compounds wherein $R^{14}$ is O$C_{1-30}$alkyl, —O-aryl, —O—$C_{1-30}$alk-C(O)$C_{1-30}$alkyl, —O—$C_{1-30}$alk-C(O)N($R^{15}$)($R^{16}$), —O-monosaccharide, —S—$C_{1-30}$alkyl, a peptidyl moiety, an isopeptide moiety, or a peptidyl-isopeptide moiety.

In other embodiments, $R^{14}$ is —O$C_{1-30}$alkyl, preferably, O$C_{1-20}$alkyl, more preferably O$C_{1-10}$alkyl or O$C_{1-6}$alkyl. Examples of O$C_{1-30}$alkyl include, for example, O$C_1$alkyl, O$C_2$alkyl, O$C_3$alkyl, O$C_4$alkyl, O$C_5$alkyl, O$C_6$alkyl, O$C_7$alkyl, O$C_8$alkyl, O$C_9$alkyl, O$C_{10}$alkyl, O$C_{11}$alkyl, O$C_{12}$alkyl, O$C_{13}$alkyl, O$C_{14}$alkyl, O$C_{15}$alkyl, O$C_{16}$alkyl, O$C_{17}$alkyl, O$C_{18}$alkyl, O$C_{19}$alkyl, O$C_{20}$alkyl, O$C_{21}$alkyl, O$C_{22}$alkyl, O$C_{23}$alkyl, O$C_{24}$alkyl, O$C_{25}$alkyl, O$C_{26}$alkyl, O$C_{27}$alkyl, O$C_{28}$alkyl, O$C_{28}$alkyl, or O$C_{30}$alkyl.

In other embodiments, $R^{14}$ is —Oaryl, where aryl is defined above. In some aspects, $R^{14}$ is —O-phenyl were the phenyl group is optionally substituted.

In further embodiments, $R^{14}$ is —O—$C_{1-30}$alk-C(O)$C_{1-30}$alkyl, preferably, —O—$C_{1-20}$alk-C(O)$C_{1-20}$alkyl, more preferably —O—$C_{1-10}$alk-C(O)$C_{1-10}$alkyl. Examples of —O—$C_{1-30}$alk-C(O)$C_{1-30}$alkyl include, for example, —O-$C_1$alk-C(O)$C_1$alkyl, —O-$C_1$alk-C(O)$C_2$alkyl, —O—$C_1$alk-C(O)$C_3$alkyl, —O—$C_1$alk-C(O)$C_4$alkyl, —O—$C_1$alk-C(O)$C_5$alkyl, —O—$C_2$alk-C(O)$C_1$alkyl, —O—$C_2$alk-C(O)$C_2$alkyl, —O—$C_2$alk-C(O)$C_3$alkyl, —O—$C_2$alk-C(O)$C_4$alkyl, —O—$C_2$alk-C(O)$C_5$alkyl, —O—$C_3$alk-C(O)$C_1$alkyl, —O—$C_3$alk-C(O)$C_2$alkyl, —O—$C_3$alk-C(O)$C_3$alkyl, —O—$C_3$alk-C(O)$C_4$alkyl, —O—$C_3$alk-C(O)$C_5$alkyl, —O—$C_4$alk-C(O)$C_1$alkyl, —O—$C_4$alk-C(O)$C_2$alkyl, -O-$C_4$alk-C(O)$C_3$alkyl, —O—$C_4$alk-C(O)$C_4$alkyl, —O—$C_4$alk-C(O)$C_5$alkyl, —O-$C_5$alk-C(O)$C_1$alkyl, —O-$C_5$alk-C(O)$C_2$alkyl, —O-$C_5$alk-C(O)$C_3$alkyl, —O-$C_5$alk-C(O)$C_4$alkyl, or —O-$C_5$alk-C(O)$C_5$alkyl.'

In other aspects, the carboxylic acid prodrug includes moieties as described in U.S. Pat. No. 5,073,641, incorporated herein by reference. For example, in some embodiments, $R^{14}$ is —O—$C_{1-30}$alk-C(O)N($R^{15}$)($R^{16}$), where $R^{15}$ and $R^{16}$ are, independently, optionally substituted $C_{1-30}$alkyl, $C_{2-20}$alkenyl, aryl, arylalkyl, or $C_{3-10}$cycloalkyl. In some embodiments, $R^{15}$ and $R^{16}$ are, independently, $C_{1-10}$alkyl. In other embodiments, $R^{15}$ and $R^{16}$ are, independently, $C_{2-10}$ alkenyl. In further embodiments, $R^{15}$ and $R^{16}$ are, independently, aryl. In still other embodiments, $R^{15}$ and $R^{16}$ are, independently, arylalkyl. In yet further embodiments, $R^{15}$ and $R^{16}$ are, independently, $C_{3-10}$cycloalkyl. In some aspects, one or both of $R^{15}$ and $R^{16}$ is optionally substituted with one or more halogen, OH, carbonyl, $C_{1-10}$alkoxy, $C_{5-10}$aryloxy, C(O)N$R^{17}R^{18}$ ($R^{17}$ and $R^{18}$ are, independently, H, $C_{1-30}$alkyl, or —$CH_2$N$R^{19}R^{20}$, wherein $R^{19}$ and $R^{20}$ are, independently, H, $C_{1-30}$alkyl, or together form a 4-7-membered heterocyclic ring optionally comprising one or two further nitrogen, oxygen, and sulfur atoms), N$R^{21}R^{22}$, wherein $R^{21}$ and $R^{22}$ are, independently, H, $C_{1-30}$alkyl, or together a 4-7-membered heterocyclic ring optionally further comprising one or two of nitrogen, oxygen, or sulfur atoms, COO$R^{23}$ ($R^{23}$ is $C_{1-20}$alkyl, aryl, or arylalkyl), $R^{24}$COO— ($R^{24}$ is H, $C_{1-30}$alkyl, aryl, arylalkyl, $C_{3-10}$ cycloalkyl, wherein the alkyl, aryl, arylalkyl or cycloalkyl group is optionally substituted with one or more halogen, OH, $C_{1-30}$ alkoxy, CONR$^{17}R^{18}$ as defined above, or NR$^{21}R^{22}$ as defined above. In other aspect, $R^1$ and $R^2$ are combined to form a 4-, 5-, 6- or 7-membered heterocyclic ring optionally comprising one or two further nitrogen, oxygen, or sulfur atoms. In some embodiments, the $R^1$+$R^2$ heterocyclic is substituted with OH, carbonyl, $C_{1-10}$alkyl, $R^{24}$COO— ($R^{24}$ is defined above), or formula —COO$R^{23}$ ($R^{23}$ is defined above). In other embodiments, the $R^{14}$ group is the compound of formula I described in U.S. Pat. No. 5,073,641.

In yet other embodiments, $R^{14}$ is —O-monosaccharide, which is optionally substituted. In some embodiments, $R^{14}$ is a O-(linear-chain monosaccharide). In other embodiments, $R^{14}$ is —O-(cyclic monosachride) such as a 5- or 6-membered cyclic monosaccharide. In some aspects, $R^{14}$ is —O-(optionally substituted furanosyl) such as —O-fructosyl. In other aspects, $R^{14}$ is —O-(optionally substituted pyranosyl) such as —O-ribosyl, —O-arabinosyl, —O-xylosyl, —O-lyxosyl, —O-allosyl, —O-altrosyl, —O-glucosyl, —O-ammosyl, —O-gylosyl, —O-iodosyl, —O-galactosyl, —O-talosyl, or —O-glucuronide. In further embodiments, $R^{14}$ is —O-glucuronide, for example:

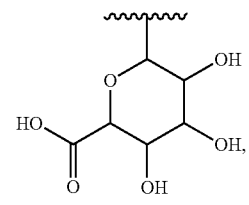

or more preferably

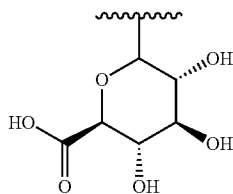 [SMILES: *C1O[C@H](C(=O)O)[C@@H](O)[C@H](O)[C@H]1O]

(β-glucuronide).

In other embodiments, $R^{14}$ is —S—$C_{1-30}$alkyl, preferably, —S—$C_{1-20}$alkyl, more preferably —S—$C_{1-10}$alkyl. Examples of —S—$C_{1-30}$alkyl include, for example, —S—$C_1$alkyl, —S—$C_2$alkyl, —S—$C_3$alkyl, —S—$C_4$alkyl, —S-$C_5$alkyl, —S—$C_6$alkyl, —S—$C_7$alkyl, —S-$C_5$alkyl, —S—$C_9$alkyl, —S—$C_{10}$alkyl, —S-$C_{11}$alkyl, —S-$C_{12}$alkyl, —S—$C_{13}$alkyl, —S—$C_{14}$alkyl, —S-$C_{15}$alkyl, —S—$C_{1-6}$alkyl, —S—$C_{17}$alkyl, —S-$C_{15}$alkyl, —S—$C_{19}$alkyl, —S—$C_{20}$alkyl, —S—$C_{21}$alkyl, —S—$C_{22}$alkyl, —S—$C_{23}$alkyl, —S—$C_{24}$alkyl, —S—$C_{25}$alkyl, —S—$C_{26}$alkyl, —S—$C_{27}$alkyl, —S—$C_{28}$alkyl, —S—$C_{28}$alkyl, or —S—$C_{30}$alkyl.

In further embodiments, $R^{14}$ is a peptidyl moiety. In some aspects, the $R^{14}$ peptide contains 1 to 5 amino acid residues, for example, the $R^{14}$ peptide contains 1 amino acid residue, 2 amino acid residues, 3 amino acid residues, 4 amino acid residues, or 5 amino acid residues. In other aspects, the amino acids are naturally-occurring amino acids, i.e., one of the 20 amino acids that are encoded by the universal genetic code, such as alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, and valine. Preferably, the naturally-occurring amino acids are L-amino acids. In other embodiments, the naturally-occurring amino acids are D-amino acids.

In further aspects, the amino acids are non-naturally-occurring amino acids, i.e., are not encoded by the universal genetic code and that include an amine moiety and a carboxylic acid moiety.

In yet other aspects, the amino acids are a combination of naturally- and non-naturally occurring amino acids. See, e.g., the peptides described in Choi et al., Protease-Activated Drug Development, Theranostics, 2012, 2(2):156-178 and Zhong et al., Cathepsin B-Cleavable Doxorubicin Prodrugs for Targeted Cancer Therapy (Review), International Journal of Oncology, 42:373-383, both of which are herein incorporated by reference.

The peptidyl group of $R^{14}$ may be bound to the compound of Formula (I) or (II) through an oxygen atom, sulfur atom, or nitrogen atom of the peptide group. In some embodiments, the peptidyl group of $R^{14}$ may be bound to the compound of Formula (I) or (II) through an oxygen atom. In other embodiments, the peptidyl group of $R^{14}$ may be bound to the compound of Formula (I) or (II) through a sulfur atom. In further embodiments, the peptidyl group of $R^{14}$ may be bound to the compound of Formula (I) or (II) through a nitrogen atom.

In yet other embodiments, $R^{14}$ is an isopeptide moiety. The term "isopeptide" as used herein refers an amide bond that is not present on the main chain of the amino acid or peptide:

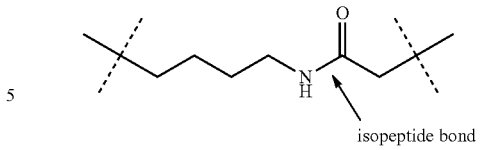

In some embodiments, the isopeptide comprises a first amino acid bound through a carboxyl terminus to an amino group of a second amino acid. In some aspects, $R^{14}$ is —NH—$C_{1-10}$alk-CH(NH$_2$)($C_{1-10}$alkyl)OH, —NH—$C_{1-10}$alk-CH(NHC$_{1-10}$alkyl)($C_{1-10}$alkyl)OH, —NH—$C_{1-10}$alk-CH(N[$C_{1-10}$alkyl]$_2$)($C_{1-10}$alkyl)OH, —NH—$C_{1-10}$alk-CH (NH$_2$)(CO—$C_{1-10}$alkyl), —NH—$C_{1-10}$alk-CH(NHC$_{1-10}$alkyl)(CO—$C_{1-10}$alkyl), —NH—$C_{1-10}$alk-CH(N[$C_{1-10}$alkyl]$_2$)(CO—$C_{1-10}$alkyl), —NH—$C_{1-10}$alk-CH(NH$_2$) (COO—$C_{1-10}$alkyl), —NH—$C_{1-10}$alk-CH(NHC$_{1-10}$alkyl) (COO—$C_{1-10}$alkyl), or —NH—$C_{1-10}$alk-CH(N[$C_{1-10}$alkyl]$_2$)(COO—$C_{1-10}$alkyl). In some aspects, $R^{14}$ is an isopeptide that is —NH—$C_{1-10}$alk-CH(NH$_2$)($C_{1-10}$alkyl)OH, for example, —NH—$C_{1-5}$alk-CH(NH$_2$)($C_{1-5}$alkyl)OH, —NH—$C_{5-10}$alk-CH(NH$_2$)($C_{5-10}$alkyl)OH, or —NH—$C_{7-10}$alk-CH(NH$_2$)($C_{7-10}$alkyl)OH. In other preferred embodiments, $R^{14}$ is —NH—$C_{1-10}$alk-CH(NHC$_{1-10}$alkyl) ($C_{1-10}$alkyl)OH, for example, —NH—$C_{1-5}$alk-CH(NHC$_{1-5}$ alkyl)($C_{1-5}$alkyl)OH, —NH—$C_{5-10}$alk-CH(NHC$_{5-10}$alkyl) ($C_{5-10}$alkyl)OH, or —NH—$C_{7-10}$alk-CH(NHC$_{7-10}$alkyl) ($C_{7-10}$alkyl)OH. In further preferred embodiments, $R^{14}$ is —NH—$C_{1-10}$alk-CH(N[$C_{1-10}$alkyl]$_2$)($C_{1-10}$alkyl)OH, for example, —NH—$C_{1-5}$alk-CH(N[$C_{1-5}$alkyl]$_2$)($C_{1-5}$alkyl) OH, —NH—$C_{5-10}$alk-CH(N[$C_{5-10}$alkyl]$_2$)($C_{5-10}$alkyl)OH, or —NH—$C_{7-10}$alk-CH(N[$C_{7-10}$alkyl]$_2$)($C_{1-10}$alkyl)OH. In still other preferred embodiments, $R^{14}$ is an isopeptide that is —NH—$C_{1-10}$alk-CH(NH$_2$)(CO—$C_{1-10}$alkyl), for example, —NH—$C_{1-15}$alk-CH(NH$_2$)(CO—$C_{1-5}$alkyl), —NH—$C_{5-10}$alk-CH(NH$_2$)(CO—$C_{5-10}$alkyl), or —NH—$C_{7-10}$alk-CH(NH$_2$)(CO—$C_{7-10}$alkyl). In further preferred embodiments, $R^{14}$ is —NH—$C_{1-10}$alk-CH(NHC$_{1-10}$alkyl) (CO—$C_{1-10}$alkyl), for example, —NH—$C_{1-5}$alk-CH (NHC$_{1-5}$ alkyl)(CO—$C_{1-5}$alkyl), —NH—$C_{5-10}$alk-CH (NHC$_{5-10}$alkyl)(CO—$C_{5-10}$alkyl), or —NH—$C_{7-10}$alk-CH (NHC$_{7-10}$alkyl)(CO—$C_{7-10}$alkyl). In yet other embodiments, $R^{14}$ is —NH—$C_{1-10}$alk-CH(N[$C_{1-10}$alkyl]$_2$) (CO—$C_{1-10}$alkyl), for example, —NH—$C_{1-5}$alk-CH(N[$C_{1-5}$ alkyl]$_2$)(CO—$C_{1-5}$alkyl), —NH—$C_{5-10}$alk-CH(N[$C_{5-10}$ alkyl]$_2$)(CO—$C_{5-10}$alkyl), or —NH—$C_{7-10}$alk-CH(N[$C_{7-10}$ alkyl]$_2$)(CO—$C_{7-10}$alkyl). In further embodiments, $R^{14}$ is an isopeptide moiety that is —NH—$C_{5-10}$alk-CH(NH$_2$) (COO—$C_{1-10}$alkyl), for example, —NH—$C_{1-5}$alk-CH (NH$_2$)(COO—$C_{1-5}$alkyl), —NH—$C_{5-10}$alk-CH(NH$_2$) (COO—$C_{5-10}$alkyl), or —NH—$C_{7-10}$alk-CH(NH$_2$)(COO—$C_{7-10}$alkyl). In other aspects, $R^{14}$ is an isopeptide moiety that is —NH—$C_{1-10}$alk-CH(NHC$_{1-10}$alkyl)(COO—$C_{1-10}$alkyl), for example, —NH—$C_{1-5}$alk-CH(NHC$_{1-5}$alkyl)(COO—$C_{1-5}$ alkyl), —NH—$C_{5-10}$alk-CH(NHC$_{5-10}$alkyl)(COO—$C_{5-10}$alkyl), or —NH—$C_{7-10}$alk-CH(NHC$_{7-10}$alkyl) (COO—$C_{7-10}$alkyl). In further aspects, $R^{14}$ is an isopeptide moiety that is —NH—$C_{1-10}$alk-CH(N[$C_{1-10}$alkyl]$_2$)(COO—$C_{1-10}$alkyl), for example, —NH—$C_{1-5}$alk-CH(N[$C_{1-5}$ alkyl]$_2$)(COO—$C_{1-5}$alkyl), —NH—$C_{5-10}$alk-CH(N[$C_{5-10}$ alkyl]$_2$)(COO—$C_{5-10}$alkyl), or —NH—$C_{5-10}$alk-CH(N [$C_{1-10}$alkyl]$_2$)(COO—$C_{1-10}$alkyl).

In some aspects, the OH group of the $R^{14}$ isopeptide moeity that is —NH—$C_{5-10}$alk-CH(NH$_2$)($C_{1-10}$alkyl)OH, —NH—$Cl_{1-10}$alk-CH(NHC$_{1-10}$alkyl)($C_{1-10}$alkyl)OH, —NH—$C_{1-10}$alk-CH(N[$C_{1-10}$alkyl]$_2$)($C_{1-10}$alkyl)OH may be capped with a polyalkylene glycol group, such as a polyethylene glycol. In some embodiments, the molecular weight of the polyethylene glycol is about 100 to about 500,000. In other embodiments, the molecular weight of the polyethylene glycol is about 100 to about 100,000. In further embodiments, the molecular weight of the polyethylene glycol is about 200 to about 10,000. In still other embodiments, the molecular weight of the polyethylene glycol is about 500 to about 5,000. In yet further embodiments, the molecular weight of the polyethylene glycol is about 600 to about 4,000. In other embodiments, the molecular weight of the polyethylene glycol is about 1,000 to about 3,000. In further embodiments, the molecular weight of the polyethylene glycol is about 1,500 to about 2,500. In some aspects, the molecular weight of the polyethylene glycol is about 200, 300, 400, 5000, 600, 700, 800, 810, 900, 1000, 1100, 1200 1300, 1400, 1500, 1540, 1600, 1700, 1800, 1900, 2000, 3000, 4000, 5000, 6000, 7000, 8000, 9000, 10000, 50000, 100000, 200000, 300000, or 400000 are available. In some preferred aspects, the molecular weight of the polyethylene glycol is about 200, 300, 400, 600, 810, 1000, 1500, 1540, 4000, 6000, 10000, 400000. Examples of the isopeptide include:

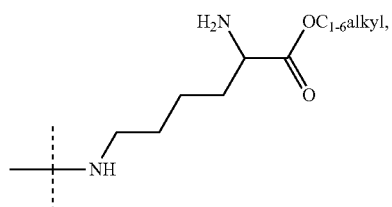

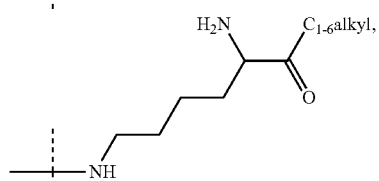

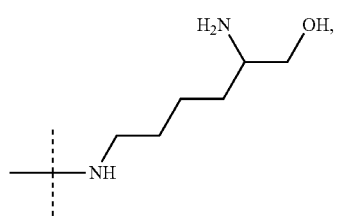

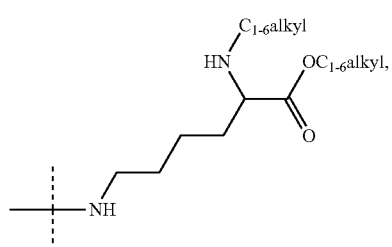

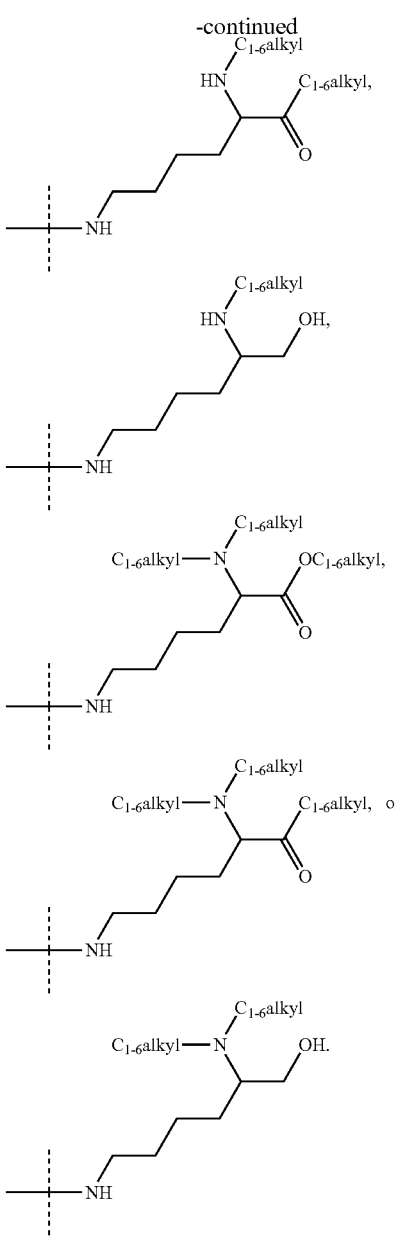

In still further embodiments, $R^{14}$ is a peptidyl-isopeptide moiety. In the peptidyl-isopeptide, the peptide is linked through an oxygen atom, sulfur atom, or nitrogen atom of the peptide to the isopeptide. In some aspects, the peptide is linked through an oxygen atom. In other aspects, the peptide is linked through a sulfur atom. In further aspects, the peptide is linked trough a nitrogen atom of the peptide. The hydroxy, thiol, or amino linking group may be present at any position of the peptidyl moiety, provided that it forms a stable bond with the isopeptidyl moiety. In some embodiments, the peptide of the peptidyl-isopeptide comprises naturally-occurring amino acids, non-naturally-occurring amino acids, or a combination thereof. In further embodiments, the peptidyl moiety contains about 1 to about 5 amino acids. In some aspects, the peptidyl moiety contains 1 amino acid. In further aspects, the peptidyl moiety contains 2 amino acids. In further aspects, the peptidyl moiety contains 3 amino acids. In other aspects, the peptidyl moiety contains 4 amino acids. In still further aspects, the peptidyl moiety contains 5 amino acids. In other embodiments, $R^{14}$ is -Q-NH—$C_{1-10}$alk-CH(NH$_2$)($C_{1-10}$alkyl)OH, -Q-NH—$C_{1-10}$alk-CH(NHC$_{1-10}$alkyl)($C_{1-10}$alkyl)OH, -Q-NH—$C_{1-10}$alk-CH(N[$C_{1-10}$alkyl]$_2$)($C_{1-10}$alkyl)OH, -Q-NH—$C_{1-10}$alk-CH(NH$_2$)(CO—$C_{1-10}$alkyl), -Q-NH—$C_{1-10}$alk-CH(NHC$_{1-10}$alkyl)(CO—$C_{1-10}$alkyl), -Q-NH—$C_{1-10}$alk-CH(N[$C_{1-10}$alkyl]$_2$)(CO—$C_{1-10}$alkyl), -Q-NH—$C_{1-10}$alk-CH(NH$_2$)(COO—$C_{1-10}$alkyl), -Q-NH—$C_{1-10}$alk-CH(NHC$_{1-10}$alkyl)(COO—$C_{1-10}$alkyl), or -Q-NH—$C_{1-10}$alk-CH(N[$C_{1-10}$alkyl]$_2$)(COO—$C_{1-10}$alkyl). In some preferred embodiments, $R^{14}$ is -Q-NH—$C_{1-10}$alk-CH(NH$_2$)($C_{1-10}$alkyl)OH, for example, -Q-NH—$C_{1-5}$alk-CH(NH$_2$)($C_{1-5}$alkyl)OH, -Q-NH—$C_{5-10}$alk-CH(NH$_2$)($C_{5-10}$alkyl)OH, or -Q-NH—$C_{7-10}$alk-CH(NH$_2$)($C_{7-10}$alkyl)OH. In other preferred embodiments, $R^{14}$ is -Q-NH—$C_{1-10}$alk-CH(NHC$_{1-10}$alkyl)($C_{1-10}$alkyl)OH, for example, -Q-NH—$C_{1-5}$alk-CH(NHC$_{1-5}$alkyl)($C_{1-5}$alkyl)OH, -Q-NH—$C_{5-10}$alk-CH(NHC$_{5-10}$alkyl)($C_{5-10}$alkyl)OH, or -Q-NH—$C_{7-10}$alk-CH(NHC$_{7-10}$alkyl)($C_{7-10}$alkyl)OH. In further preferred embodiments, $R^{14}$ is —NH—$C_{1-10}$alk-CH(N[$C_{1-10}$alkyl]$_2$)($C_{1-10}$alkyl)OH, for example, —NH—$C_{1-5}$alk-CH(N[$C_{1-5}$alkyl]$_2$)($C_{1-5}$alkyl)OH, —NH—$C_{5-10}$alk-CH(N[$C_{5-10}$alkyl]$_2$)($C_{5-10}$alkyl)OH, or —NH—$C_{7-10}$alk-CH(N[$C_{7-10}$alkyl]$_2$)($C_{1-10}$alkyl)OH. In still other preferred embodiments, $R^{14}$ is -Q-NH—$C_{1-10}$alk-CH(NH$_2$)(CO—$C_{1-10}$alkyl), for example, -Q-NH—$C_{1-15}$alk-CH(NH$_2$)(CO—$C_{1-5}$alkyl), -Q-NH—$C_{5-10}$alk-CH(NH$_2$)(CO—$C_{5-10}$alkyl), or -Q-NH—$C_{7-10}$alk-CH(NH$_2$)(CO—$C_{7-10}$alkyl). In further preferred embodiments, $R^{14}$ is -Q-NH—$C_{1-10}$alk-CH(NHC$_{1-10}$alkyl)(CO—$C_{1-10}$alkyl), for example, -Q-NH—$C_{1-5}$alk-CH(NHC$_{1-5}$alkyl)(CO—$C_{1-5}$alkyl), -Q-NH—$C_{5-10}$alk-CH(NHC$_{5-10}$alkyl)(CO—$C_{5-10}$alkyl), or -Q-NH—$C_{7-10}$alk-CH(NHC$_{7-10}$alkyl)(CO—$C_{7-10}$alkyl). In yet other embodiments, $R^{14}$ is -Q-NH—$C_{1-10}$alk-CH(N[$C_{1-10}$alkyl]$_2$)(CO—$C_{1-10}$alkyl), for example, -Q-NH—$C_{1-5}$alk-CH(N[$C_{1-5}$alkyl]$_2$)(CO—$C_{1-10}$alkyl), -Q-NH—$C_{5-10}$alk-CH(N[$C_{5-10}$alkyl]$_2$)(CO—$C_{5-10}$alkyl), or -Q-NH—$C_{7-10}$alk-CH(N[$C_{7-10}$alkyl]$_2$)(CO—$C_{7-10}$alkyl). In further embodiments, $R^{14}$ is -Q-NH—$C_{1-10}$alk-CH(NH$_2$)(COO—$C_{1-10}$alkyl), for example, -Q-NH—$C_{1-5}$alk-CH(NH$_2$)(COO—$C_{1-5}$alkyl), -Q-NH—$C_{5-10}$alk-CH(NH$_2$)(COO—$C_{5-10}$alkyl), or -Q-NH—$C_{7-10}$alk-CH(NH$_2$)(COO—$C_{7-10}$alkyl). In further preferred embodiments, $R^{14}$ is -Q-NH—$C_{1-10}$alk-CH(NHC$_{1-10}$alkyl)(COO—$C_{1-10}$alkyl), for example, -Q-NH—$C_{1-5}$alk-CH(NHC$_{1-5}$alkyl)(COO—$C_{1-5}$alkyl), -Q-NH—$C_{5-10}$alk-CH(NHC$_{5-10}$alkyl)(COO—$C_{5-10}$alkyl), or -Q-NH—$C_{7-10}$alk-CH(NHC$_{7-10}$alkyl)(COO—$C_{7-10}$alkyl). In further preferred embodiments, $R^{14}$ is -Q-NH—$C_{1-10}$alk-CH(N[$C_{1-10}$alkyl]$_2$)(COO—$C_{1-10}$alkyl), for example, -Q-NH—$C_{1-5}$alk-CH(N[$C_{1-5}$alkyl]$_2$)(COO—$C_{1-5}$alkyl), -Q-NH—$C_{5-10}$alk-CH(N[$C_{5-10}$alkyl]$_2$)(COO—$C_{5-10}$alkyl), or -Q-NH—$C_{7-10}$alk-CH(N[$C_{7-10}$alkyl]$_2$)(COO—$C_{7-10}$alkyl).

Examples of peptidyl-isopeptide moieties include:

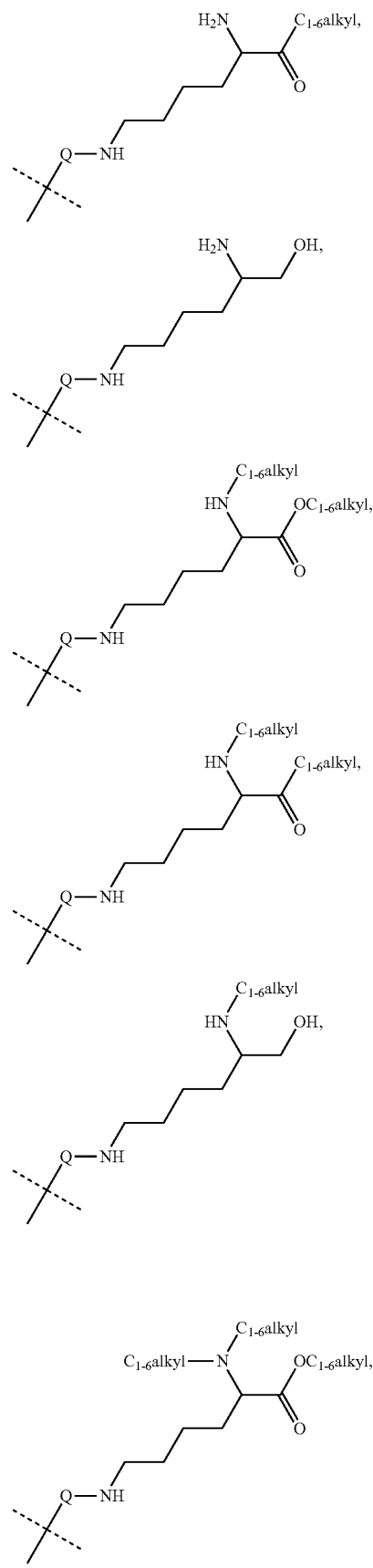

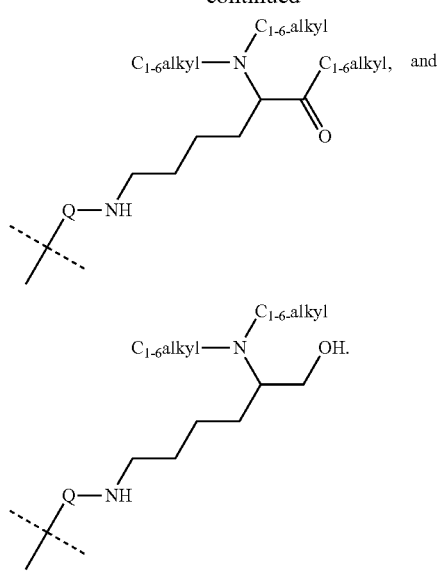
wherein Q is the peptidyl moiety.
In some preferred embodiments, the compound is:
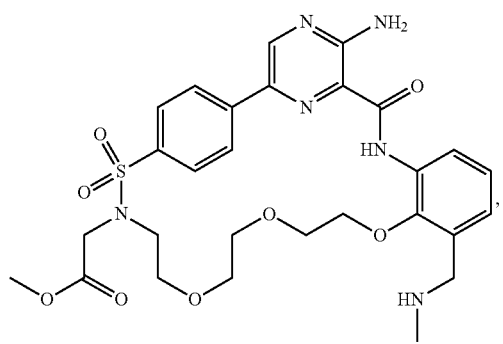
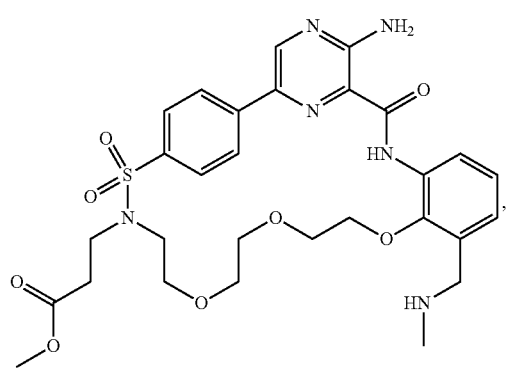
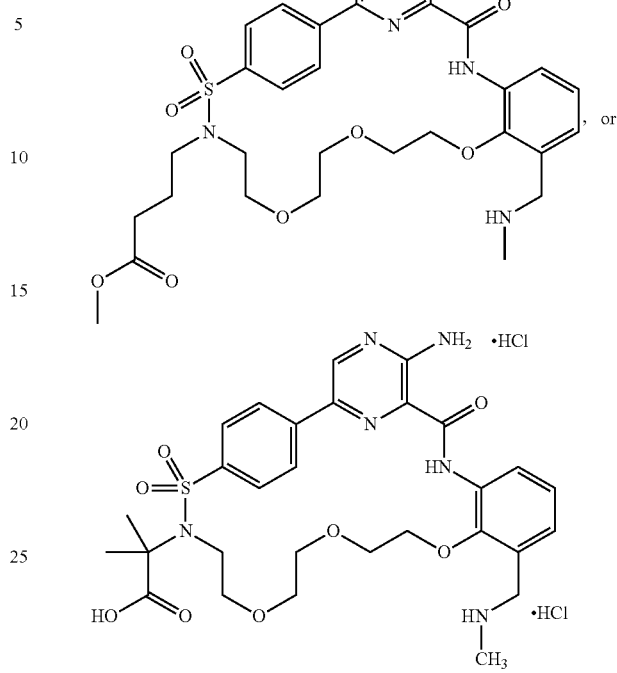
or a pharmaceutically acceptable salt thereof.
In other preferred embodiments, the compound is
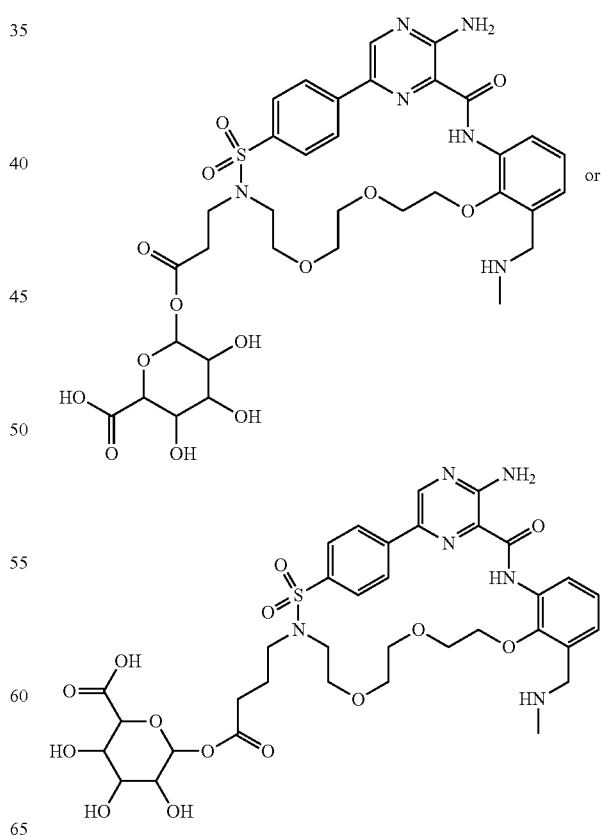
or a pharmaceutically acceptable salt thereof.

In still further embodiments, the compound is:
Compounds of Formula (III) and (IV)
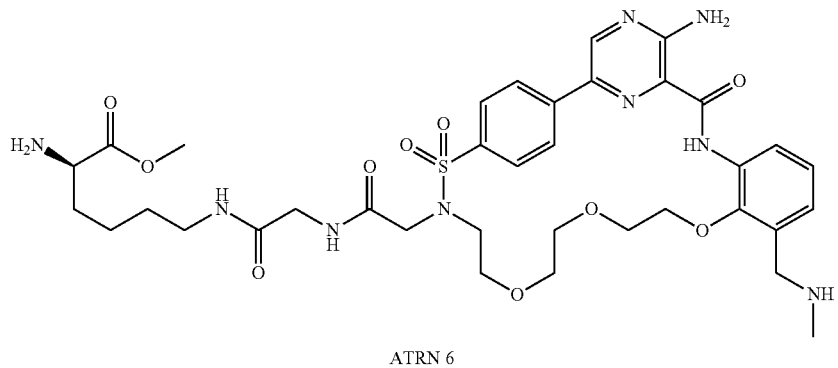 [SMILES: CNCc1cccc2c1OCCOCCOCCN(CC(=O)NCC(=O)NCCCC[C@@H](N)C(=O)OC)S(=O)(=O)c1ccc(cc1)-c1cnc(N)c(n1)C(=O)N2]
ATRN 6
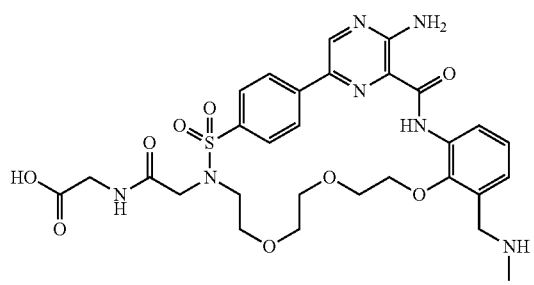
ATRN 6-A
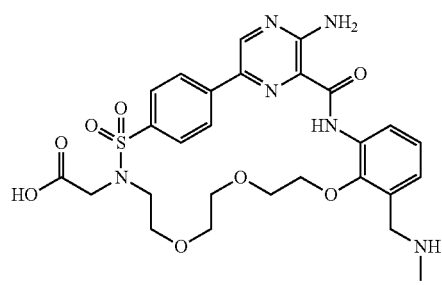
ATRN 6-B
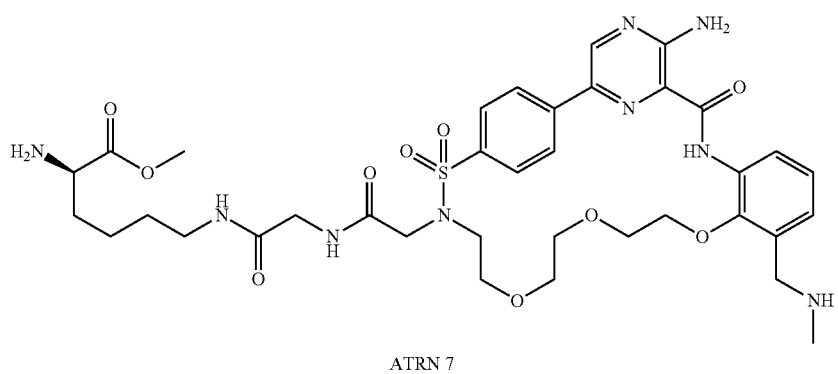
ATRN 7
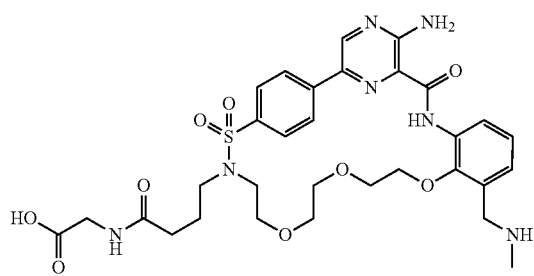
ATRN 7-A
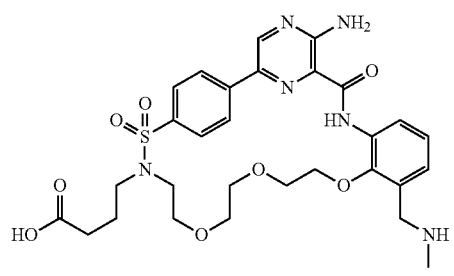
ATRN 7-B The present disclosure is directed to compounds of Formula (III) and Formula (IV):

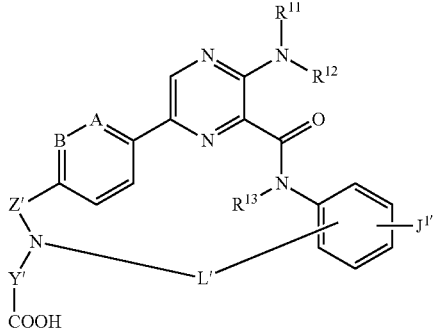
(III)

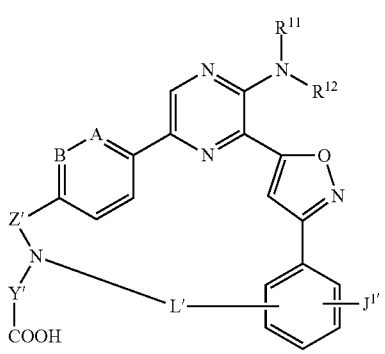
(IV)

Preferred embodiments of Formula (III) include compounds of Formula (III-A) and (III-B):

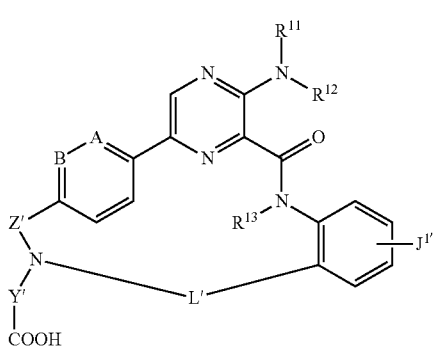
(III-A)

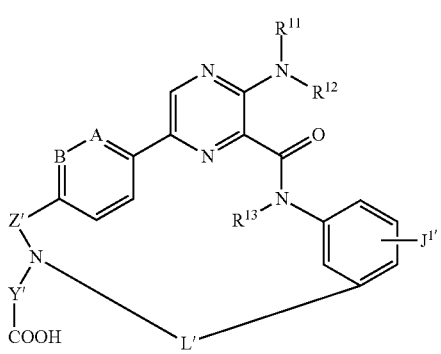
(III-B)

Preferred embodiments of Formula (I) include compounds of Formula (IV-A) and (IV-B):

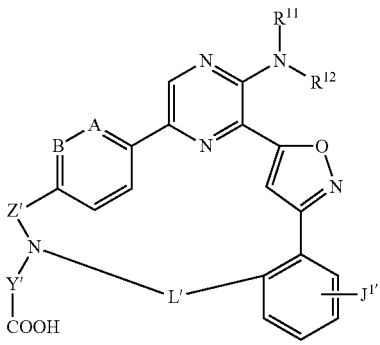
(IV-A)

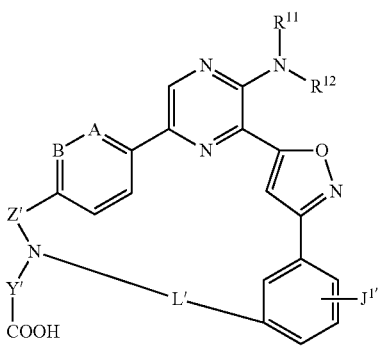
(IV-B)

According to the disclosure, A is CH or N. In some aspects, A is CH. In other aspects, A is N. Also according to the disclosure, B is CH or N. In some aspects, B is CH. In other aspects, B is N. In preferred embodiments, A is CH and B is CH. In other embodiments, A is N and B is CH. In yet other embodiments, A is CH and B is N. In still other embodiments, A is N and B is N.

According to the disclosure, $R^{11}$ is H or $C_{1-6}$alkyl. In some aspects, $R^{11}$ is H. In other aspects, $R^{11}$ is $C_{1-6}$alkyl, for example, methyl, ethyl, propyl, isopropyl, butyl, isobutyl, tert-butyl, pentyl, or hexyl.

According to the disclosure, $R^{12}$ is H or $C_{1-6}$alkyl. In some aspects, $R^{12}$ is H. In other aspects, $R^{12}$ is $C_{1-6}$alkyl, for example, methyl, ethyl, propyl, isopropyl, butyl, isobutyl, tert-butyl, pentyl, or hexyl.

According to the disclosure, $R^{13}$ is H or $C_{1-6}$alkyl. In some aspects, $R^{13}$ is H. In other aspects, $R^{13}$ is $C_{1-6}$alkyl, for example, methyl, ethyl, propyl, isopropyl, butyl, isobutyl, tert-butyl, pentyl, or hexyl.

In preferred aspects, each of $R^{11}$, $R^{12}$, and $R^{13}$ is H. In some aspects, $R^{11}$ is H and $R^{12}$ and $R^{13}$ are each independently $C_{1-6}$alkyl. In some aspects, $R^{12}$ is H and $R^{11}$ and $R^{13}$ are each independently $C_{1-6}$alkyl. In some aspects, $R^{13}$ is H and $R^{11}$ and $R^{12}$ are each independently $C_{1-6}$alkyl. In other aspects, $R^{11}$ and $R^{12}$ are each H and $R^{13}$ is $C_{1-6}$alkyl. In other aspects, $R^{11}$ and $R^{13}$ are each H and $R^{12}$ is $C_{1-6}$alkyl. In other aspects, $R^{12}$ and $R^{13}$ are each H and $R^{11}$ is $C_{1-6}$alkyl.

According to the disclosure, Z' is —SO$_2$— or —C(O)—. In some aspects, Z' is —SO$_2$—. In other aspects, Z' is —C(O)—.

According to the disclosure, Y' is an alkylene (i.e., an "alk"), for example, a $C_1$-$C_{12}$alkylene, preferably a $C_{1-6}$alkylene. In preferred aspects, Y' is $C_1$alkylene, $C_2$alkylene, $C_3$alkylene, $C_4$alkylene, $C_4$alkylene, $C_5$alkylene, $C_7$alkylene, $C_8$alkylene, $C_9$alkylene, $C_{10}$alkylene, $C_{11}$alkylene, or $C_{12}$alkylene. In some embodiments, Y' is $C_1$alkylene. In other embodiments, Y' is C$_2$alkylene. In yet other embodiments, Y' is C$_3$alkylene. In still other embodiments, Y' is C$_4$alkylene.

According to the disclosure, J$^{1'}$ is H, optionally substituted —C$_{1-6}$alkyl, —C$_{0-6}$alk-NH-(optionally substituted C$_{1-6}$alkyl), or —C$_{0-6}$alk-NH—C$_{0-6}$alk-(optionally substituted C$_{3-6}$heterocycloalkyl). Also according to the disclosure, J$^{1'}$ is H, optionally substituted —C$_{1-6}$alkyl, —C$_{1-6}$alk-NH-(optionally substituted C$_{1-6}$alkyl), or —C$_{1-6}$alk-NH—C$_{0-6}$alk-(optionally substituted C$_{3-6}$heterocycloalkyl). In some aspects, J$^{1'}$ is H. In other aspects, J$^{1'}$ is —C$_{1-6}$alkyl, for example methyl, ethyl, propyl, isopropyl, butyl, isobutyl, tert-butyl, pentyl, or hexyl. In some embodiments wherein J$^{1'}$ is —C$_{1-6}$alkyl, the C$_{1-6}$alkyl is substituted with one, two, or three substituents independently selected from halo (F, Cl, Br, or I, preferably F), —OH, —OC$_{1-6}$alkyl, and —CN.

In other aspects, J$^{1'}$ is —C$_{0-6}$alk-NH—(C$_{1-6}$alkyl), for example, —C$_{1-6}$alk-NH—(C$_{1-6}$alkyl), —C$_{1-5}$alk-NH—(C$_{1-6}$ alkyl), —C$_{1-4}$alk-NH—(C$_{1-6}$alkyl), —C$_{1-3}$alk-NH—(C$_{1-6}$alkyl), —C$_{1-2}$alk-NH—(C$_{1-6}$alkyl), —C$_1$alk-NH—(C$_{1-6}$alkyl), or —C$_0$alk-NH—(C$_{1-6}$alkyl). In other aspects, J$^{1'}$ is —C$_{0-6}$alk-NH—(C$_{1-5}$alkyl), for example, —C$_{1-6}$alk-NH—(C$_{1-5}$alkyl), —C$_{0-6}$alk-NH—(C$_{1-5}$alkyl), C$_{0-6}$alk-NH—(C$_{1-4}$alkyl), C$_{0-6}$alk-NH—(C$_{1-3}$alkyl), C$_{0-6}$alk-NH—(C$_{1-2}$alkyl), or C$_{0-6}$alk-NH—(C$_1$alkyl). In some embodiments wherein J$^{1'}$ is —C$_{1-6}$alk-NH—(C$_{1-6}$alkyl) or —C$_{0-6}$alk-NH—(C$_{1-6}$alkyl), the C$_{1-6}$alkyl is substituted with one, two, or three substituents independently selected from halo (F, Cl, Br, or I, preferably F), —OH, —OC$_{1-6}$ alkyl, and —CN.

In some aspects, J$^{1'}$ is —C$_{0-6}$alk-NH—C$_{0-6}$alk-(C$_{3-6}$heterocycloalkyl), for example, —C$_{1-6}$alk-NH—C$_{0-6}$alk-(C$_{3-6}$heterocycloalkyl), —C$_{1-5}$alk-NH—C$_{0-6}$alk-(C$_{3-6}$heterocycloalkyl), —C$_{1-4}$alk-NH—C$_{0-6}$alk-(C$_{3-6}$heterocycloalkyl), —C$_{1-3}$alk-NH—C$_{0-6}$alk-(C$_{3-6}$heterocycloalkyl), —C$_{1-2}$alk-NH—C$_{0-6}$alk-(C$_{3-6}$heterocycloalkyl, —C$_1$alk-NH—C$_{0-6}$alk-(C$_{3-6}$heterocycloalkyl), or —C$_0$alk-NH—C$_{0-6}$alk-(C$_{3-6}$heterocycloalkyl). Alternatively, J$^{1'}$ is —C$_{0-6}$alk-NH—C$_{0-5}$alk-(C$_{3-6}$heterocycloalkyl), —C$_{1-6}$alk-NH—C$_{0-4}$alk-(C$_{3-6}$heterocycloalkyl), —C$_{1-6}$alk-NH—C$_{0-3}$alk-(C$_{3-6}$heterocycloalkyl), —C$_{1-6}$alk-NH—C$_{0-2}$alk-(C$_{3-6}$heterocycloalkyl), —C$_{1-6}$alk-NH—C$_{0-1}$alk-(C$_{3-6}$heterocycloalkyl), or —C$_{1-6}$alk-NH—C$_{0-2}$alk-(C$_{3-6}$heterocycloalkyl). In other embodiments, J$^{1'}$ is —C$_{1-6}$alk-NH—C$_{0-6}$alk-(C$_{3-5}$heterocycloalkyl), —C$_{1-6}$alk-NH—C$_{0-6}$alk-(C$_{3-4}$heterocycloalkyl), or J$^{1'}$ is —C$_{1-6}$alk-NH—C$_{0-6}$alk-(C$_3$heterocycloalkyl). The heterocycloalkyl moiety can be attached to the compounds of Formula (III) or (IV) via a ring carbon. In those embodiments incorporating a nitrogen-containing heterocycloalkyl, the heterocycloalkyl moiety can be attached via a ring carbon atom or a ring nitrogen atom. Preferred heterocycloalkyl moieties include oxetanyl and tetrahydropyranyl. In some embodiments wherein J$^{1'}$ is —C$_{1-6}$alk-NH—C$_{0-6}$alk-(C$_{3-6}$heterocycloalkyl), the heterocycloalkyl is substituted with one, two, or three substituents independently selected from halo (F, Cl, Br, or I, preferably F), —OH, —OC$_{1-6}$alkyl, and —CN.

According to the disclosure, L' is a linking group, preferably a 7 to 17-membered linking group, 7-membered linking group, 8-membered linking group, 9-membered linking group, or 10-membered linking group, for example, an alkylene (i.e., alk) optionally interrupted by 1, 2, 3, 4 or 5 heteroatom moieties independently selected from —O—, —NH—, —N(C$_{1-6}$alkyl), —N(C$_{1-6}$alkyl), and —N(C$_{1-6}$alkyl)-O(C$_{1-6}$alkyl). In those aspects wherein the alkylene is optionally interrupted by —N(C$_{1-6}$alkyl) and/or —N(C$_{1-6}$alkyl)-O(C$_{1-6}$alkyl), the C$_{1-6}$alkyl moieties can be optionally substituted with one, two, or three substituents independently selected from halo (F, Cl, Br, or I, preferably F), —OH, —OC$_{1-6}$alkyl, and —CN. In some aspects, L' is a 7 to 10-membered linking group comprising an alkylene optionally interrupted by three —O— heteroatom moieties. In other aspects, L' is a 7 to 10-membered linking group comprising an alkylene optionally interrupted by one —O— heteroatom moiety and one —NH—, —N(C$_{1-6}$alkyl), —N(optionally substituted C$_{1-6}$alkyl), or —N(C$_{1-6}$alkyl)-O (optionally substituted C$_{1-6}$alkyl) heteroatom moiety. In still other embodiments, L' is a 7 to 10-membered linking group comprising an alkylene optionally interrupted by two —O— heteroatom moieties and one —NH—, —N(C$_{1-6}$alkyl), —N(optionally substituted C$_{1-6}$alkyl), or —N(C$_{1-6}$alkyl)-O (optionally substituted C$_{1-6}$alkyl) heteroatom moiety.

Preferred L' moieties include —(CH$_2$CH$_2$O)$_3$—, —CH$_2$(CH$_2$CH$_2$O)$_2$—, —CH(C$_{1-6}$alkyl)(CH$_2$CH$_2$O)$_3$— (e.g., —CH(CH$_3$)(CH$_2$CH$_2$O)$_3$—), —(CH$_2$CH$_2$CH$_2$O)$_2$—, —CH$_2$CH$_2$NH(CH$_2$CH$_2$O)$_2$, and —O—(CH$_2$CH$_2$O)$_2$—.

Preferred compounds of Formula (III) and (IV) include the compounds of Formula (III-C), (III-D), (IV-C), and (IV-D):

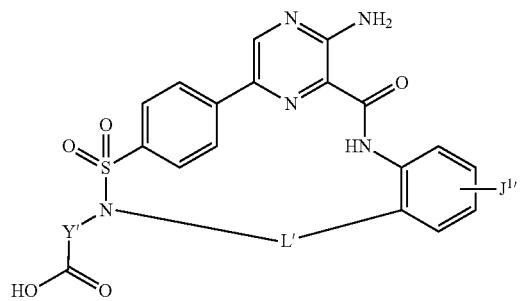

(III-C)

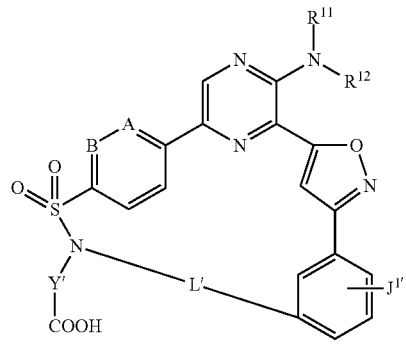

(IV-C)

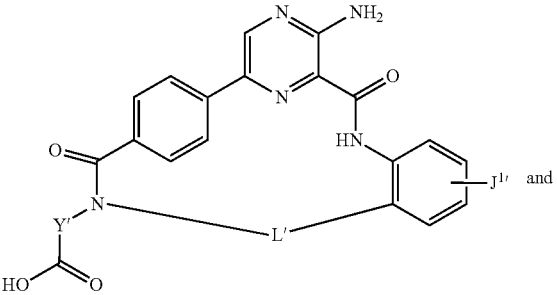

(III-D) and

Other preferred compounds of Formula (III) include:

49
-continued
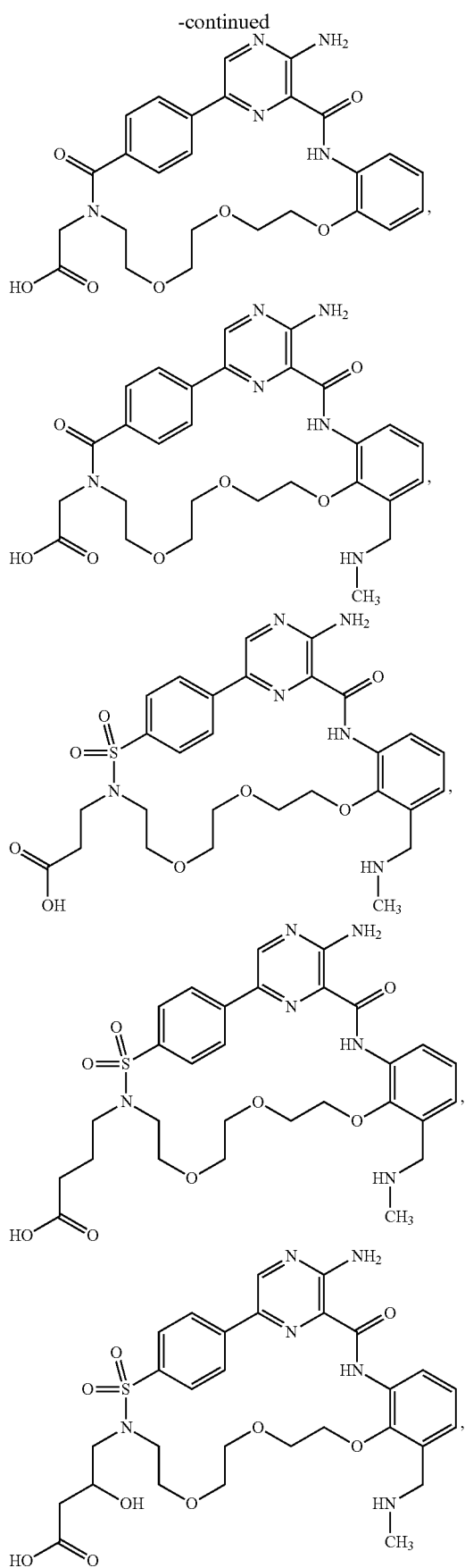
50
-continued
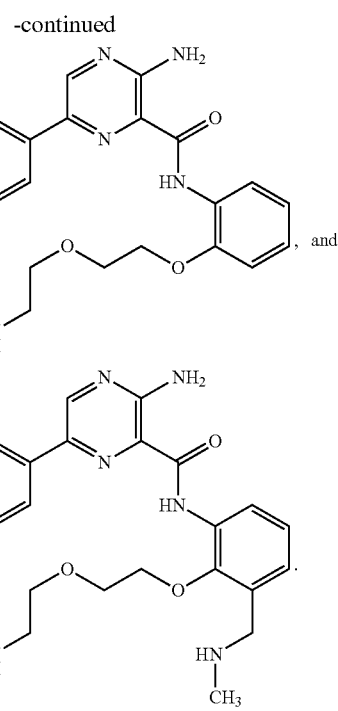
, and
Other preferred compounds of Formula (IV) include:
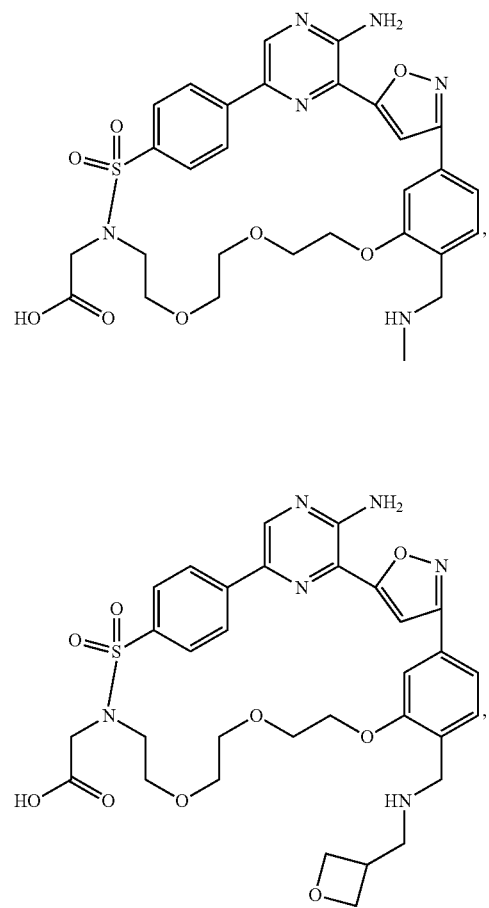

-continued

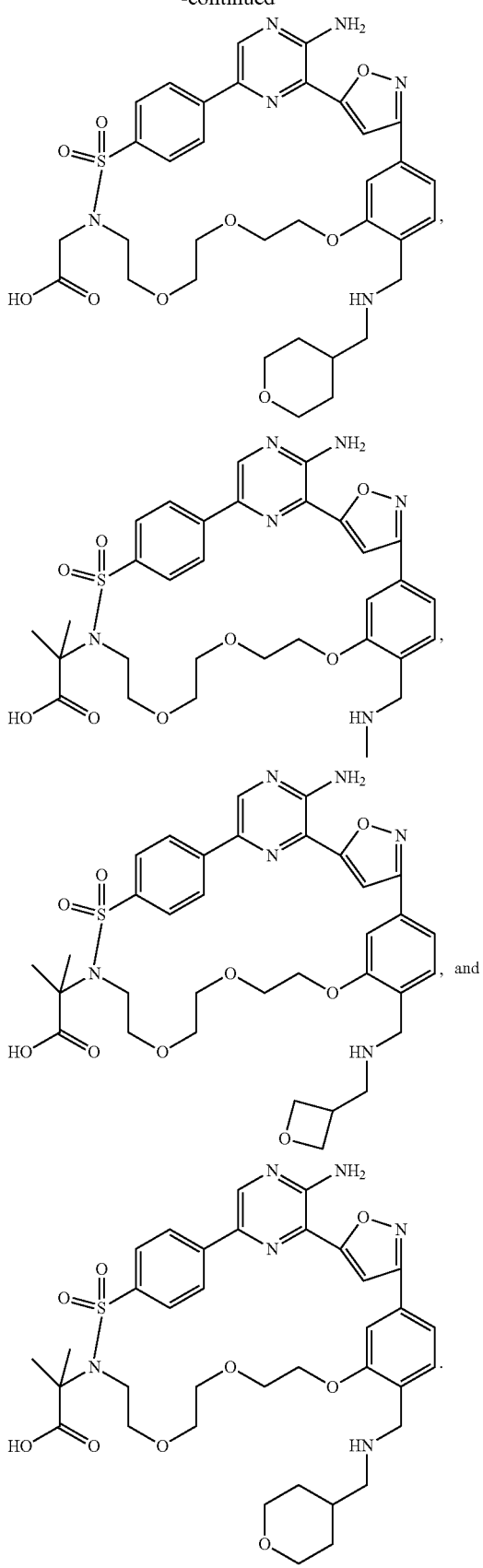

Synthesis of Compounds of Formula (I) and (II)

The compounds of the disclosure may be prepared in light of the specification using steps generally known to those of ordinary skill in the art. Those compounds may be analyzed by known methods, including but not limited to LCMS (liquid chromatography mass spectrometry) and NMR (nuclear magnetic resonance). Below are a set of generic schemes that illustrate generally how to prepare the compounds of the present disclosure.

Scheme A:

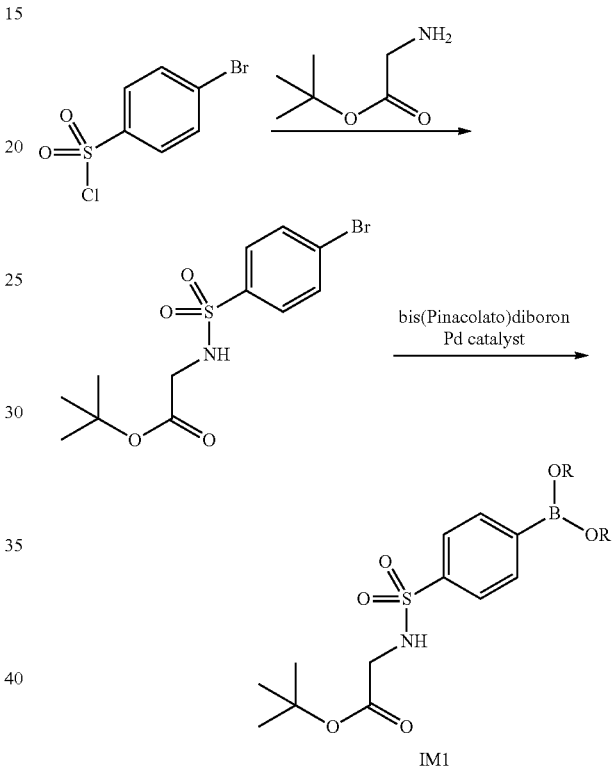

Scheme B:

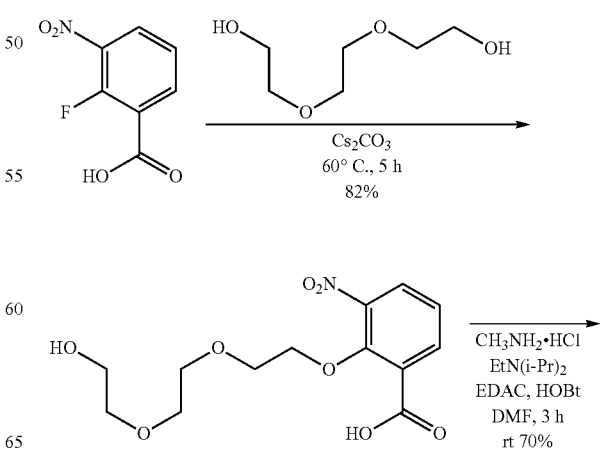

Scheme C:
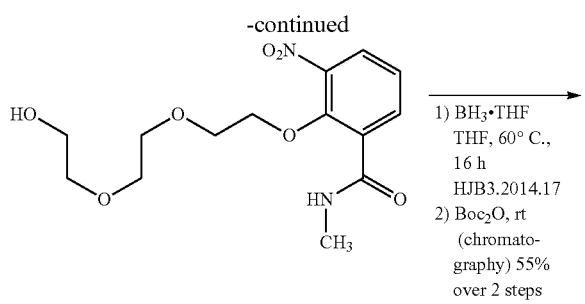
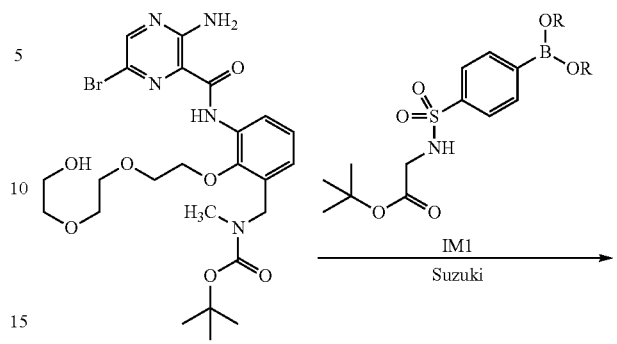
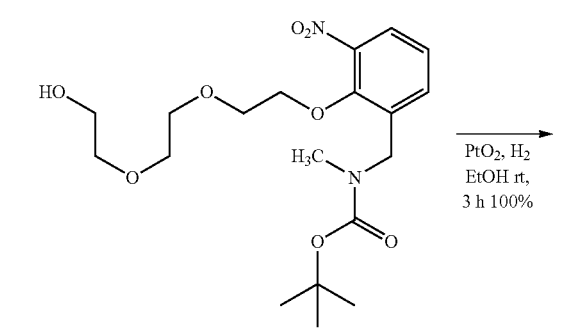
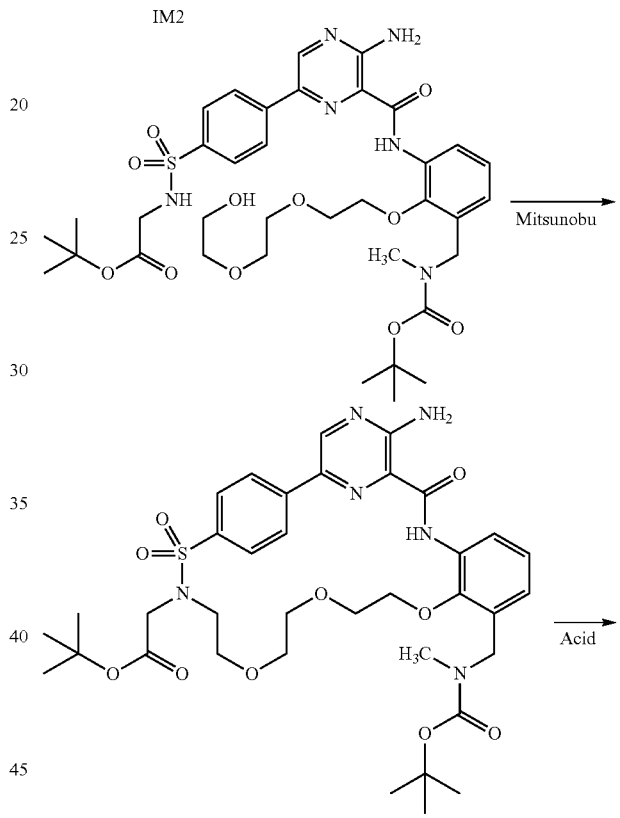
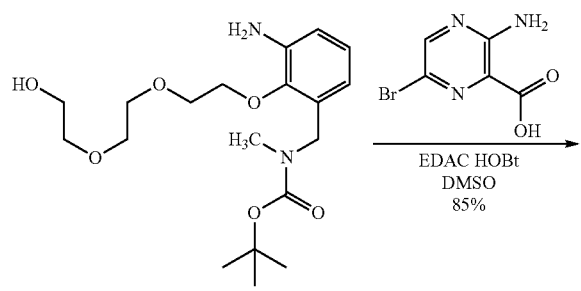
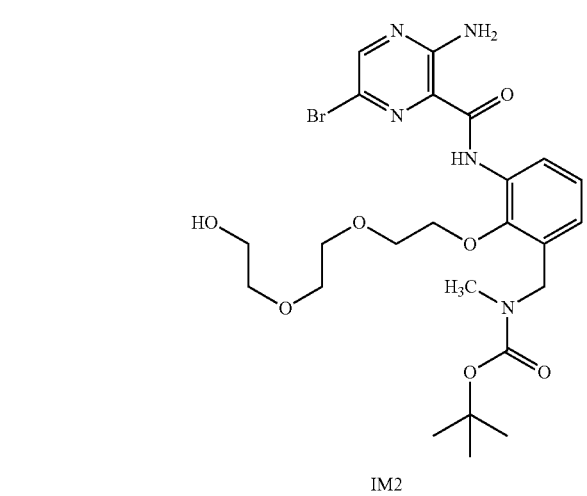
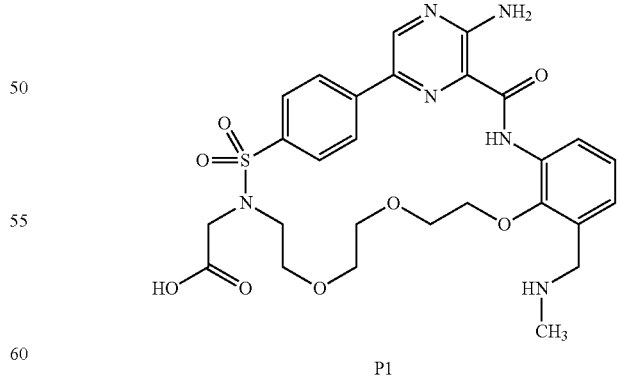
Compounds of Formula (I) and (II) where $R^{14}$ is —$OC_{1-30}$alkyl, —O-aryl, —O—$C_{1-30}$alk-C(O)$C_{1-30}$alkyl, —O-monosaccharide, or —S—$C_{1-30}$alkyl may be prepared by functionalizing a compound of Formula (I) or (II) where $R^{14}$ is OH with the corresponding —$OC_{1-30}$alkyl, —O-aryl, —O—$C_{1-30}$alk-C(O)$C_{1-30}$alkyl, —O-monosaccharide, or —S—$C_{1-30}$alkyl group. See, e.g., the preparation of compounds described in Zawilska, Prodrugs: A Challenge for the Drug Development, Pharmacological Reports, 2013, 65, 1-14 and Wadouachi, Synthesis of Glycosides of Glycuronic, Galacturonic and Mannuronic Acids: An Overview, Molecules, 2011, 16, 3933-3968, which are incorporated herein by reference.

Isopeptide prodrugs can be prepared using methods known to those of ordinary skill in the art, and by reference to Schemes 1, 2, and 3.

-continued

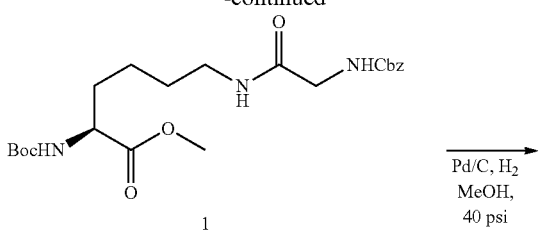

Scheme 1

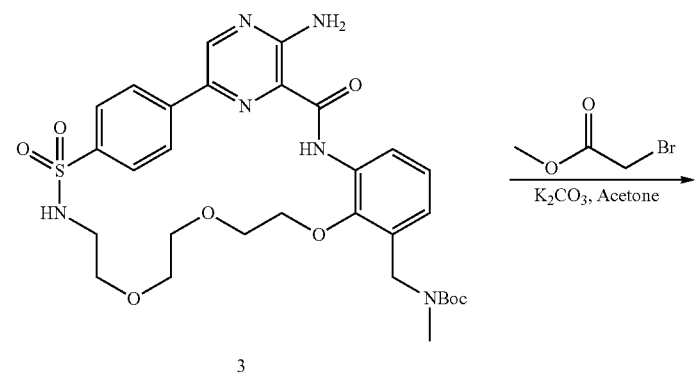

Scheme 2

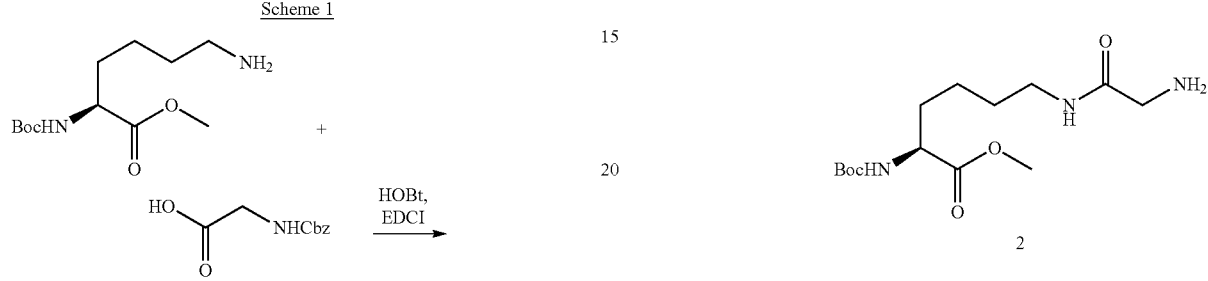

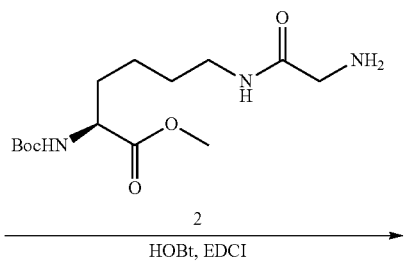

-continued
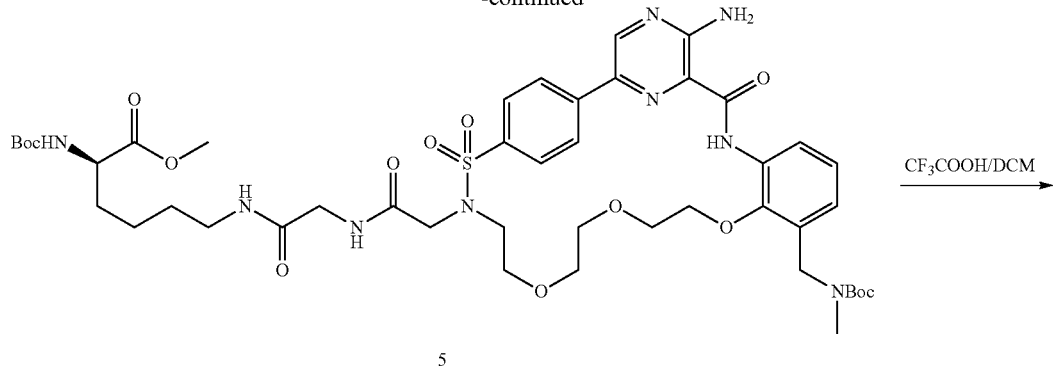
5
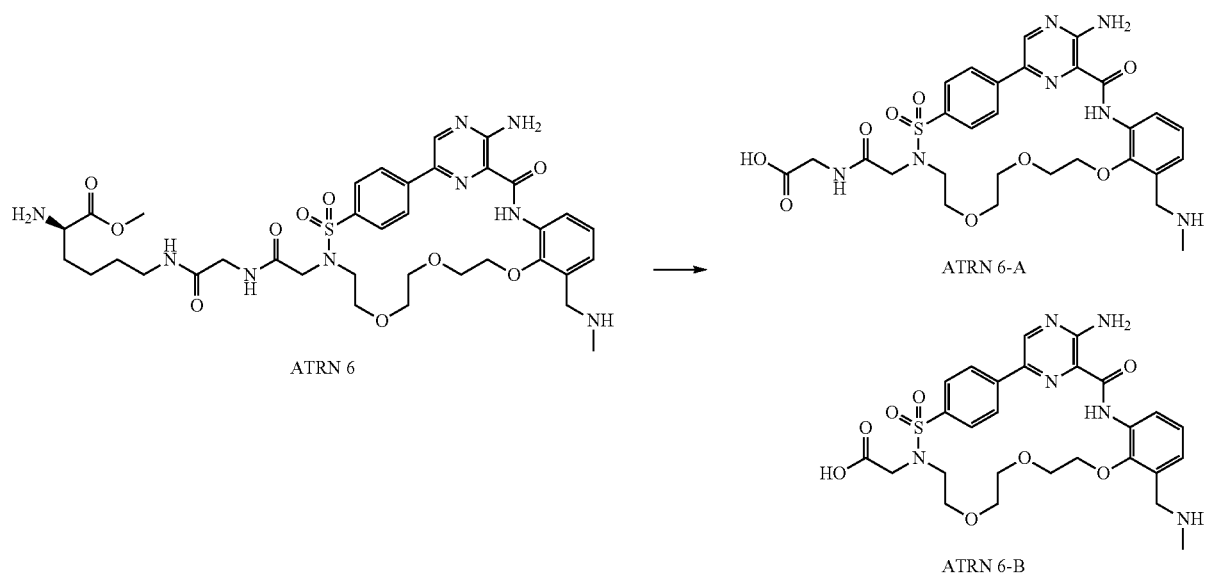
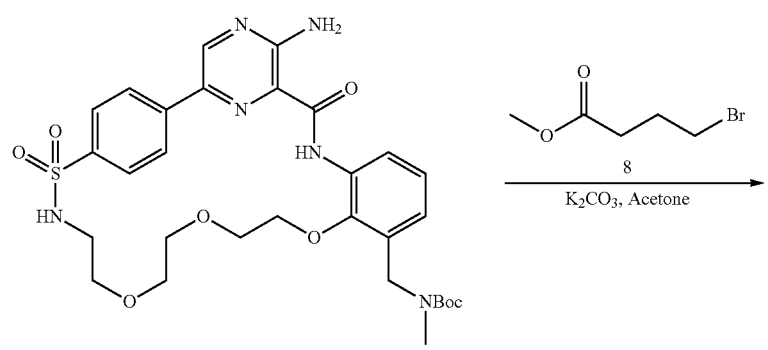

-continued

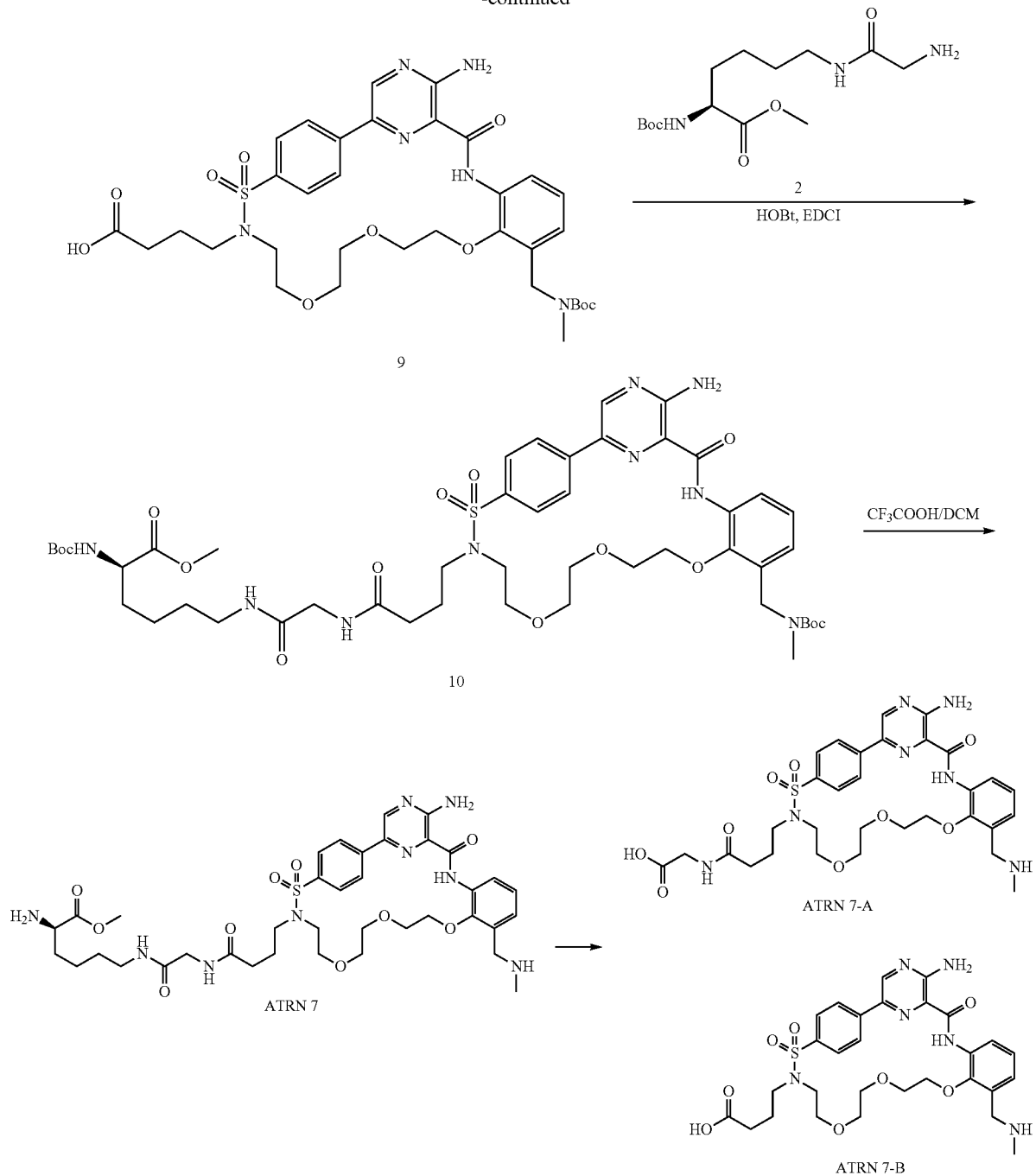

Compositions

The compounds of the disclosure are used, alone or in combination with one or more additional active ingredients, to formulate pharmaceutical compositions of the disclosure. A pharmaceutical composition of the disclosure comprises: (a) an effective amount of at least one compound in accordance with the disclosure; and (b) a pharmaceutically acceptable excipient.

The compositions may be administered in the inventive methods by a suitable route of delivery, e.g., oral, parenteral, rectal, topical, or ocular routes, or by inhalation.

For oral administration, the compounds of the disclosure can be provided in the form of tablets or capsules, or as a solution, emulsion, or suspension. To prepare the oral compositions, the compounds may be formulated to yield a dosage of, e.g., from about 0.05 to about 100 mg/kg daily, or from about 0.05 to about 35 mg/kg daily, or from about 0.1 to about 10 mg/kg daily. For example, a total daily dosage of about 5 mg to 5 g daily may be accomplished by dosing once, twice, three, or four times per day.

Oral tablets or capsules may include a compound according to the disclosure mixed with pharmaceutically acceptable excipients such as inert diluents, disintegrating agents, binding agents, lubricating agents, sweetening agents, flavoring agents, coloring agents and preservative agents.

The active agents of this disclosure may also be administered by non-oral routes. For example, the compositions may be formulated for rectal administration as a suppository. For parenteral use, including intravenous, intramuscular, intraperitoneal, or subcutaneous routes, the compounds of the disclosure may be provided in sterile aqueous solutions or suspensions, buffered to an appropriate pH and isotonicity or in parenterally acceptable oil. Suitable aqueous vehicles include Ringer's solution and isotonic sodium chloride.

The compounds described herein may also be formulated in combination with an enzyme inhibitor. In some embodiments, the enzyme inhibitor is an elastase inhibitor, more preferably elastatinal. In other embodiments, the enzyme inhibitor is a trypsin inhibitor, more preferably antipain or leupeptin. In further embodiments, the enzyme inhibitor is an aminopeptidase N inhibitor, preferably puromycin, amastatin, bestatin, or phosphinate inhibitor VI. In still other embodiments, the enzyme inhibitor is a pepsin inhibitor, preferably pepstatin. In yet further embodiments, the enzyme inhibitor is a chymotrypsin inhibitor, preferably chymostatin. In other embodiments, the enzyme inhibitor is a neutral aminopeptidase inhibitor, preferably phosphoramidon.

Methods of Treatment

The macrocyclic compounds, compositions containing the same and methods of treatment of the present disclosure have utility in treating many disease conditions, including cancer (e.g., central nerve system, breast, pancreatic, lung, ovarian, leukemia, Lymphoma, melanoma, renal, prostate, colorectal, brain, and glioblastoma). In at least one embodiment, the compositions and methods are used to treat diseases such as ocular melanoma, desmoplastic round cell tumor, chondrosarcoma, leptomengial disease, diffuse large B-cell lymphoma, Acute Lymphoblastic Leukemia, Acute Myeloid Leukemia, Adrenocortical Carcinoma, AIDS-Related Cancers, AIDS-Related Lymphoma, Anal or Rectal Cancer, Appendix Cancer, Astrocytomas, and Atypical Teratoid/Rhabdoid Tumor. In at least one embodiment, the compositions and methods are used to treat diseases such as Basal Cell Carcinoma, Bile Duct Cancer, Bladder Cancer, Bone Cancer, Osteosarcoma and Malignant Fibrous Histiocytoma, Brain Tumor, Breast Cancer, Prostate Cancer, Bronchial Tumors, Burkitt Lymphoma, and Spinal Cord Tumors. In at least one embodiment, the compositions and methods are used to treat diseases such as Carcinoid Tumor, Carcinoma of Unknown Primary, Central Nervous System Atypical Teratoid/Rhabdoid Tumor, Leptomeningeal Disease, Central Nervous System Embryonal Tumors, Central Nervous System Lymphoma, Cervical Cancer, Chordoma, Chronic Lymphocytic Leukemia, Chronic Myelogenous Leukemia, Chronic Myeloproliferative Disorders, Colon Cancer, Colorectal Cancer, Craniopharyngioma, and Cutaneous T-Cell Lymphoma. In at least one embodiment, the compositions and methods are used to treat diseases such as Endometrial Cancer, Ependymoblastoma, Ependymoma, Esophageal Cancer, Ewing Sarcoma Family of Tumors, Extracranial Germ Cell Tumor, Extragonadal Germ Cell Tumor, Extrahepatic Bile Duct Cancer, and Eye Cancer. In at least one embodiment, the compositions and methods are used to treat diseases such as Gallbladder Cancer, Gastric (Stomach) Cancer, Gastrointestinal Carcinoid Tumor, Gastrointestinal Stromal Tumor (GIST), Germ Cell Tumor, Gestational Trophoblastic Tumor, and Glioma. In at least one embodiment, the compositions and methods are used to treat cancer selected from the group consisting of Hairy Cell Leukemia, Head and Neck Cancer, Hepatocellular (Liver) Cancer, Histiocytosis, Hodgkin Lymphoma, and Hypopharyngeal Cancer. In at least one embodiment, the compositions and methods are used to treat diseases such as Kaposi Sarcoma, and Kidney (Renal Cell) Cancer. In at least one embodiment, the compositions and methods are used to treat diseases such as Langerhans Cell Histiocytosis, Laryngeal Cancer, Lip and Oral Cavity Cancer, Liver Cancer, Lung Cancer, Non-Hodgkin Lymphoma, and Primary Central Nervous System Lymphoma. In at least one embodiment, the compositions and methods are used to treat diseases such as Waldenström's macroglobulinemia (lymphoplasmacytic lymphoma), Malignant Fibrous Histiocytoma of Bone and Osteosarcoma, Medulloblastoma, Medulloepithelioma, Melanoma, Merkel Cell Carcinoma, Mesothelioma, Metastatic Squamous Neck Cancer with Occult Primary, Multiple Endocrine Neoplasia Syndrome, Mouth Cancer, Multiple Myeloma/Plasma Cell Neoplasm, Mycosis Fungoides, Myelodysplastic Syndromes, Myelodysplastic/Myeloproliferative Neoplasms, Multiple Myeloma, and Myeloproliferative Disorders. In at least one embodiment, the compositions and methods are used to treat cancer. In at least one embodiment, the compositions and methods are used to treat diseases such as Nasal Cavity and Paranasal Sinus Cancer, Nasopharyngeal Cancer, and Neuroblastoma. In at least one embodiment, the compositions and methods are used to treat diseases such as Oropharyngeal Cancer, Osteosarcoma and Malignant Fibrous Histiocytoma of Bone, Ovarian Cancer, Ovarian Germ Cell Tumor, Ovarian Epithelial Cancer, and Ovarian Low Malignant Potential Tumor. In at least one embodiment, the compositions and methods are used to treat diseases such as Pancreatic Cancer, Papillomatosis, Paranasal Sinus and Nasal Cavity Cancer, Parathyroid Cancer, Penile Cancer, Pharyngeal Cancer, Pineal Parenchymal Tumors of Intermediate Differentiation, Pineoblastoma and Supratentorial Primitive Neuroectodermal Tumors, Pituitary Tumor, Pleuropulmonary Blastoma, Pregnancy and Breast Cancer, and Prostate Cancer. In at least one embodiment, the compositions and methods are used to treat cancer selected from the group consisting of Rectal Cancer, Renal Pelvis and Ureter, Respiratory Tract Carcinoma Involving the NUT Gene on Chromosome 15, Retinoblastoma, and Rhabdomyosarcoma. In at least one embodiment, the compositions and methods are used to treat high grade prostate cancer. In at least one embodiment, the compositions and methods are used to treat medium grade prostate cancer. In at least one embodiment, the compositions and methods are used to treat low grade prostate cancer. In at least one embodiment, the compositions and methods are used to treat castration-resistant prostate cancer. In some embodiments, the cancer is breast cancer, prostate cancer, pancreatic cancer, lung cancer, colorectal cancer, ovarian cancer, liver cancer, melanoma, renal cancer, a central nervous system cancer, brain cancer, glioblastoma, a leukemia, or a lymphoma.

In at least one embodiment, the compositions and methods are used to treat a proliferative skin disorder. In at least one embodiment, the compositions and methods are used to treat a proliferative skin disorder, wherein the proliferative skin disorder is psoriasis. In at least one embodiment, the compositions and methods are used to treat cancer selected from the group consisting of Salivary Gland Cancer, Sarcoma, Sézary Syndrome, Skin Cancer, Ocular Cancer, Skin Carcinoma, Small Intestine Cancer, Soft Tissue Sarcoma, Squamous Cell Carcinom, Squamous Neck Cancer with Occult Primary, and Supratentorial Primitive Neuroectodermal Tumors. In at least one embodiment, the compositions and methods are used to treat cancer selected from the group consisting of T-Cell Lymphoma, Testicular Cancer, Throat Cancer, Thymoma and Thymic Carcinoma, Thyroid Cancer, Transitional Cell Cancer of the Renal Pelvis and Ureter, and Gestational Trophoblastic Tumor. In at least one embodiment, the compositions and methods are used to treat cancer selected from the group consisting of Carcinoma of Unknown Primary Site, Cancer of Unknown Primary Site such as carcinoma of unknown primary site, Unusual Cancers of Childhood, Urethral Cancer, and Uterine Sarcoma. In at least one embodiment, the compositions and methods are used to treat cancer selected from the group consisting of Vaginal Cancer, Vulvar Cancer, Wilm's tumor, or a women's cancer. In at least one embodiment, the compositions and methods are used to treat cancer selected from the group consisting of Wilms Tumor, and Women's Cancers.

The utility of the methods and compositions is not limited to any particular animal species. In at least one embodiment, a subject treated according to methods and using compositions, can be mammalian or non-mammalian. In at least one embodiment, a mammalian subject can be any mammal including, but not limited to, a human; a non-human primate; a rodent such as a mouse, rat, or guinea pig; a domesticated pet such as a cat or dog; a horse, cow, pig, sheep, goat, or rabbit. In at least one embodiment, a non-mammalian subject can be any non-mammal including, but not limited to, a bird such as a duck, goose, chicken, or turkey. In at least one embodiment, subjects can be either gender and can be any age. In at least one embodiment, the compositions and methods can also be used to prevent cancer. In at least one embodiment, the compositions and methods can also be used to stimulate the immune system.

The compounds of the disclosure can also be used in combination with other therapeutic chemotherapy agents such as, for example, enzyme inhibitors, PARP inhibitors, tyrosine kinase inhibitors, DNA binding agents, mitotic inhibitors, alkylating agents, anti-metabolites, anti-tumor antibiotics, topoisomerase inhibitors, microtubule inhibitors, angiogenesis inhibitors, signal transduction inhibitors, cell cycle inhibitors, bisphosphonates, telomerase inhibitors, biological response modifiers (such as antibodies, immunotherapy and peptide mimics), anti-hormones, anti-androgens, gene silencing agents, gene activating agents, and anti-vascular agents.

Another embodiment of the disclosure provides administering a compound of this disclosure with an additional therapeutic chemotherapy agent that inhibits or modulates a base excision repair protein. In some embodiments, the base excision repair protein is selected from UNG, SMUG1, MBD4, TDG, OGG1, MYH, NTH1, MPG, NEIL1, NEIL2, NEIL3 (DNA glycosylases); APEI, APEX2 (AP endonucleases); LIG1, LIG3 (DNA ligases I and III); XRCC1 (LIG3 accessory); PNK, PNKP (polynucleotide kinase and phosphatase); PARP1, PARP2 (Poly(ADP-Ribose) Polymerases); PolB, PolG (polymerases); FEN1 (endonuclease) or Aprataxin. In other embodiments, the base excision repair protein is selected from PARP1, PARP2, or PolB. In yet other embodiments, the base excision repair protein is selected from PARP1 or PARP2. In some embodiments, the agent is selected from Olaparib (also known as AZD2281 or KU-0059436), Iniparib (also known as BSI-201 or SAR240550), Veliparib (also known as ABT-888), Rucaparib (also known as PF-01367338), CEP-9722, INO-1001, MK-4827, E7016, BMN673, or AZD2461. In one embodiment, the dosage of the additional therapeutic agent is from about 1 mg/kg to about 500 mg/kg, from about 10 mg/kg to about 400 mg/kg, from about 20 mg/kg to about 300 mg/kg, from about 10 mg/kg to about 100 mg/kg, from about 10 mg/kg to about 200 mg/kg; from about 10 mg/kg to about 150 mg/kg; from about 10 mg/kg to about 250 mg/kg; about 25 mg/kg; or about 300 mg/kg.

The compounds described herein may also be administered in combination with an enzyme inhibitor. The enzyme inhibitor may be selected by one skilled in the art as determined by cancer being treated. See, e.g., the enzyme inhibitors described in Bemkop-Schnürch, Presystemic Metabolism of Orally Administered Peptide Drugs and Strategies to Overcome It, Current Drug Metabolism, 2007, 8, 509-517, which is herein incorporated by reference. In some embodiments, the enzyme inhibitor is an elastase inhibitor, more preferably elastatinal. In other embodiments, the enzyme inhibitor is a trypsin inhibitor, more preferably antipain or leupeptin. In further embodiments, the enzyme inhibitor is an aminopeptidase N inhibitor, preferably puromycin, amastatin, bestatin, or phosphinate inhibitor VI. In still other embodiments, the enzyme inhibitor is a pepsin inhibitor, preferably pepstatin. In yet further embodiments, the enzyme inhibitor is a chymotrypsin inhibitor, preferably chymostatin. In other embodiments, the enzyme inhibitor is a neutral aminopeptidase inhibitor, preferably phosphoramidon.

All references, including publications, patent applications, and patents, cited herein, as well as International Patent Publication No. WO-2016/061097, are hereby incorporated by reference to the same extent as if each reference were individually and specifically indicated to be incorporated by reference and were set forth in its entirety herein.

EXAMPLES

The inventions will be illustrated by the following non-limiting examples: The following examples describe the preparation of representative compounds of the present invention. Melting points are reported as uncorrected in degrees centigrade. The infrared data is reported as wave numbers at maximum absorption, $v_{max}$, in reciprocal centimeters, $cm^{-1}$. Mass spectral data is reported as the mass-to-charge ratio, m/z; and for high resolution mass spectral data, the calculated and experimentally found masses, $[M^+H]^+$, for the neutral formulae M are reported. Nuclear magnetic resonance data is reported as δ in parts per million (ppm) downfield from the standard, tetramethylsilane, along with the solvent, nucleus, and field strength parameters. The spin-spin homonuclear coupling constants are reported as J values in hertz; and the multiplicities are reported as: s, singlet; d, doublet; t, triplet; q, quartet; quintet; or br, broadened.

Example 12

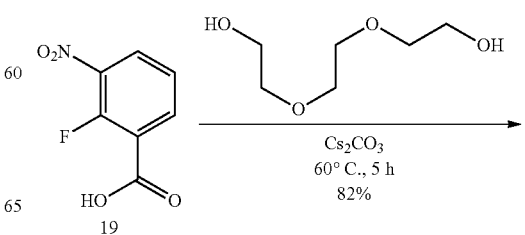

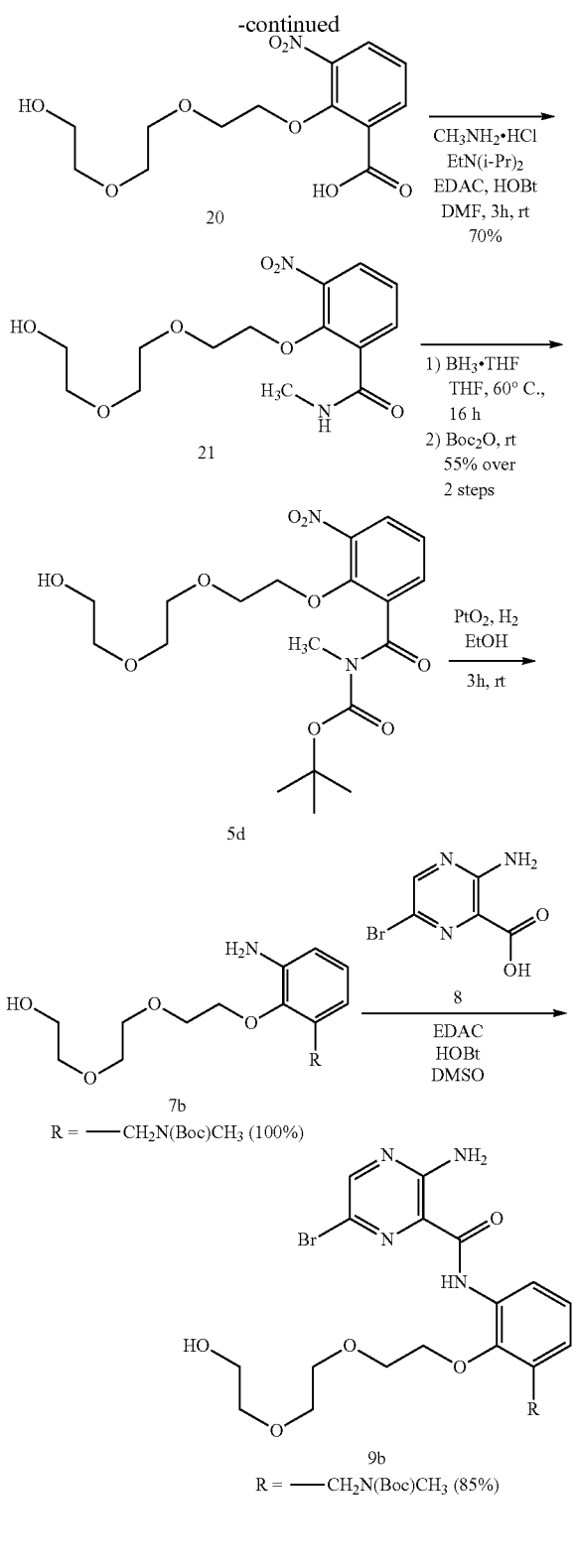

2-(2-(2-(2-Hydroxyethoxy)ethoxy)ethoxy)-3-nitrobenzoic acid (20)

A heterogeneous mixture of triethyleneglycol (183 mL, 1375 mmol), (2-fluoro-3-nitrobenzoic acid 19) (10.18 g, 55 mmol), and cesium carbonate ($Cs_2CO_3$) (39.4 g, 121 mmol) was warmed to 60° C. to give a homogenous solution. After 16 hours, heating was discontinued and the mixture was cooled to room temperature. The cooled reaction mixture was diluted with water (400 mL) and, with cooling and swirling, slowly acidified with 12N HCl to pH 2-3 (16 mL of 12 N HCl; 190 mmol). The resulting acidic solution was then extracted with $Et_2O$ (~75 mL). The layers were separated and the aqueous phase was washed with $CHCl_3$ (3×; 400 mL, 300 mL and 150 mL respectively). The $CHCl_3$ layers were combined and washed with water (2×; 100 mL each), and then with brine (100 mL). The $CHCl_3$ organic phase was then dried over $Na_2SO_4$, filtered, concentrated under reduced pressure and then under high vacuum overnight to yield 14.11 g (82%) of a yellow tinted oil. LC/MS: >95% (M+23=338.4, consistent with desired product). The isolated 2-(2-(2-(2-Hydroxyethoxy)ethoxy)ethoxy)-3-nitrobenzoic acid was used for the subsequent step without further manipulation.

2-(2-(2-(2-Hydroxyethoxy)ethoxy)ethoxy)-N-methyl-3-nitrobenzamide (21)

EDAC (12.65 g, 66 mmol) was added neat to a room temperature, homogeneous solution of 2-(2-(2-(2-Hydroxyethoxy)ethoxy)ethoxy)-3-nitrobenzoic acid (13.87 g, 44 mmol), methylamine hydrochloride (5.94 g, 88 mmol), N,N-diisopropylethylamine (DIPEA) (16.9 mL, 96.8 mmol) and HOBt (2.97 g, 2.76 mmol) in DMF (150 mL). After 2.5 hours the mixture was concentrated under reduced pressure at 45° C. The concentrated reaction mixture was partitioned between EtOAc (4×; 350 mL, 250 mL and 100 mL×2 respectively) and water (150 mL). The combined organics were then washed sequentially with water (50 mL), saturated aqueous $NaHCO_3$ (100 mL) and brine (100 mL), dried over $Na_2SO_4$, filtered and concentrated under reduced pressure at 50° C. to yield 10.14 g (70%) of desired 2-(2-(2-(2-Hydroxyethoxy)ethoxy)ethoxy)-N-methyl-3-nitrobenzamide as an oil. LC/MS: >95% (M+H=329.4; M+23=351.4, consistent with desired product).

tert-Butyl (2-(2-(2-(2-hydroxyethoxy)ethoxy)ethoxy)-3-nitrobenzyl) (methyl)carbamate (5D)

A solution of 2-(2-(2-(2-Hydroxyethoxy)ethoxy)ethoxy)-N-methyl-3-nitrobenzamide (10.01 g, 30.5 mmol) in THF (125 mL) was added dropwise over 30 minutes to a stirring 0° C. solution of 1M $BH_3$.THF in THF (137.25 mL, 137.25 mmol) and stirred for 30 more minutes at ° C. The reaction mixture was brought to room temperature for 1 hour and then the reaction was warmed to 65° C. After 24 hours the reaction was cooled to 0° C. and slowly diluted with 1N HCl (350 mL) after which the reaction was brought to room temperature. After a half hour the reaction mixture was warmed to 60° C., then 3 hours later re-cooled to 0° C. and treated with aqueous NaOH to reach a pH of 8-9. The resulting 0° C. solution of 2-{2-[2-(2-Methylaminomethyl-6-nitro-phenoxy)-ethoxy]-ethoxy}-ethanol (TLC: 10:1:0.5 EtOAc:MeOH:$NH_4OH$ Rf=0.6 (major spot); trace of starting material amide at Rf=0.7) was treated with a solution of $Boc_2O$ (8.43 g, 39.65 mmol) in THF (35 mL). After 0.5 hour the mixture was warmed to room temperature and stirred for 16 hours. The resulting mixture was concentrated under reduced pressure to remove the majority of THF, then the remaining aqueous solution was extracted with $CH_2Cl_2$ (2×; 250 mL and 100 mL respectively). The $CH_2Cl_2$ organic phases were combined and washed sequentially with 1N HCl (75 mL), saturated aqueous $NaHCO_3$ (100 mL) and brine (50 mL), then dried over $Na_2SO_4$, filtered and concentrated under reduced pressure. The concentrate was placed under high vacuum overnight to yield 11.75 g of crude tert-Butyl (2-(2-(2-(2-hydroxyethoxy)ethoxy)ethoxy)-3-nitrobenzyl) (methyl)carbamate as an amber oil. This material was adsorbed onto a silica gel column with CH$_2$Cl$_2$, and then purified by normal phase chromatography eluting with a gradient solvent system (20%-100% EtOAc/hexane). The desired fractions were combined and concentrated under reduced pressure to give 6.92 g (55%) of desired compound as an amber oil. LC/MS: (M+23=437.57, along with a strong base peak at M+H-Boc=315.5). TLC: 100% EtOAc Rf=0.6, homogeneous. The isolated compound was used for the subsequent step without further purification.

tert-Butyl (3-amino-2-(2-(2-(2-hydroxyethoxy)ethoxy)ethoxy)benzyl)(methyl) carbamate (7B)

At room temperature added a solution of tert-Butyl (2-(2-(2-(2-hydroxyethoxy)ethoxy)ethoxy)-3-nitrobenzyl) (methyl)carbamate (3 mmol) in EtOH (30 mL) to PtO$_2$ (100 mg, 0.45 mmol) in a Parr bottle and placed onto a Parr apparatus under a hydrogen atmosphere at 38 psi. After 3 hours the reaction mixture was carefully filtered through Celite, and the resulting filtrate concentrated under reduced pressure to yield 100% yield as a clear oil. LC/MS: (>95%) (M+H=385.5, consistent with desired product tert-Butyl (3-(3-amino-6-bromopyrazine-2-carboxamido)-2-(2-(2-(2-hydroxyethoxy)ethoxy)ethoxy)benzyl)(methyl)carbamate (9B)

A stirring, room temperature solution of 3-amino-6-bromopyrazine-3-carboxylic acid (2.18 g, 10 mmol), tert-Butyl (3-amino-2-(2-(2-(2-hydroxyethoxy)ethoxy)ethoxy)benzyl) (methyl) carbamate (4.61 g, 12 mmol) and HOBt (0.68 g, 5 mmol) in DMSO (16 mL) was treated with neat EDAC (4.79 g, 25 mmol). After 3 hours the reaction mixture was treated with water (50 mL) yielding a goo. The reaction mixture liquid was decanted off and the goo was treated with additional portions of water (40 mL each), again decanting between treatments. The goo was then partitioned between EtOAc (200 mL) and water (50 mL). The resulting organic phase was washed sequentially with saturated aqueous NaHCO$_3$, 1N HCl, and then saturated aqueous NaHCO$_3$ once again. The organic phase was then dried over Na$_2$SO$_4$, filtered and concentrated under reduced pressure to give an oil. This oil was placed under high vacuum overnight to yield 4.97 g (85%) of desired product as an amber oil. LC/MS: (>95%) (weak M+H=585; stronger M+23=607).

Example 13

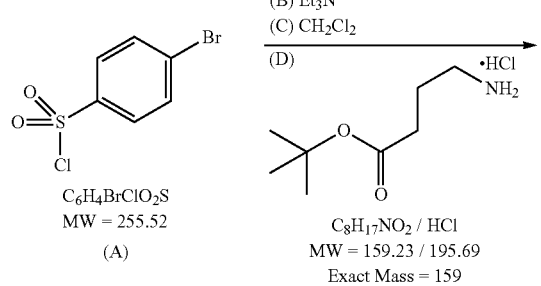

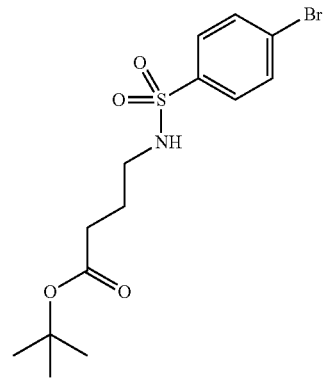

C$_{13}$H$_{18}$BrNO$_4$S
MW = 378.29
Exact Mass = 378

(A): MW 255.51 4 mmol=1.02 g (B): Et$_3$N; MW=101.19; d=0.726; 2.4 equivalents=9.6 mmol=971 mg=1.34 mL (C): CH$_2$Cl$_2$; 100 mL (D): MW=195.69; 1.05 equivalents=4.2 mmol=0.82 g (A) was dissolved in (C), then at 0° C. added (D) neat to given an almost homogeneous solution. (B) was added dropwise. The reaction was monitored via TLC (1:3 EtOAc: hexane: Rf=0.55, homogenous/SM A at solvent front). After 1.5 hours the reaction solution was washed with 1N HCl (25 mL). The organic phase was then washed with saturated aqueous NaHCO$_3$, dried over Na$_2$SO$_4$, filtered, and concentrated under reduced pressure to give 1.44 g (95%) of white solid. LC/MS (dissolved in CH$_3$CN): rt 4.37 minutes≥95% (M+23=401, consistent with desired product). TLC: 1:3 EtOAc:hexane Rf=0.5, homogeneous. $^1$H NMR (CDCl$_3$) was consistent with the structure.

Example 14: Preparation of ATRN-160 and ATRN-161

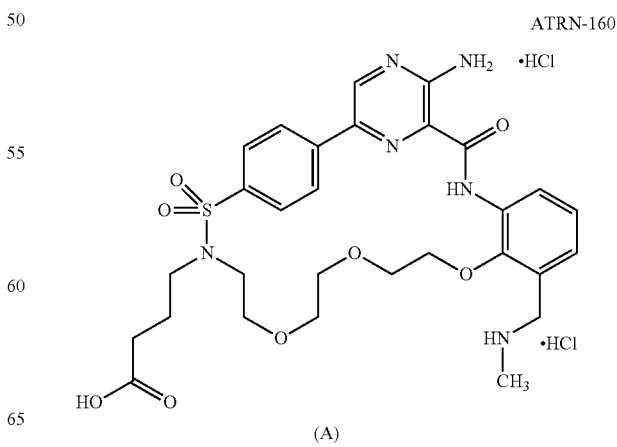

69
-continued

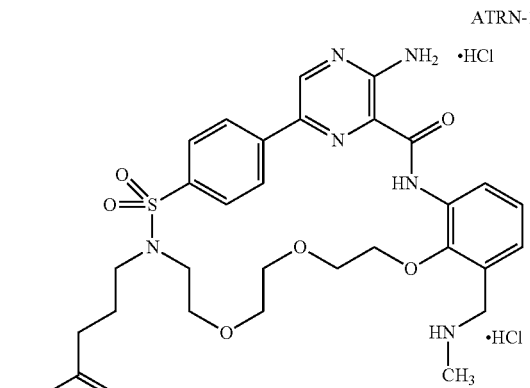

ATRN-161

Step 1

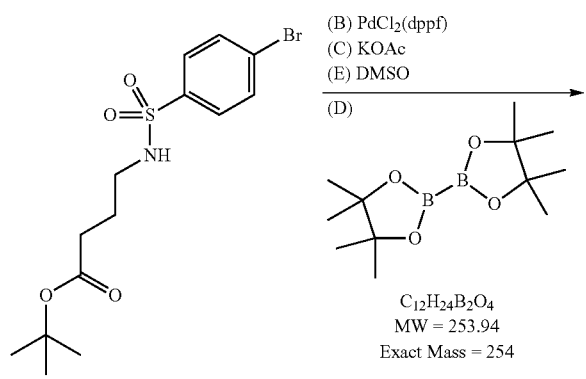

70
-continued

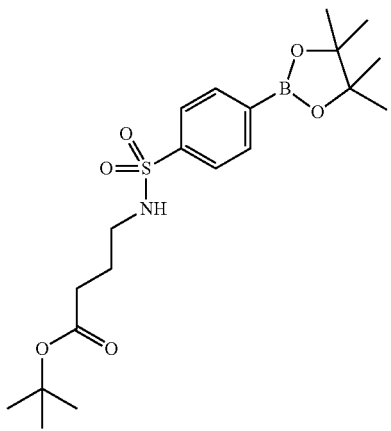

$C_{20}H_{32}BNO_6S$
MW = 425.36
Exact Mass = 425

(A): MW 378.29; 2.5 mmol=0.95 g (B): [1,1'-bis(diphenyphosphino)-ferrocene]dichloropalladium (II) complex with dichloromethane (1:1); $PdCl_2$(dppf); Aldrich; MW=816.63; 0.065 equivalents=0.1625 mmol=0.13 g (C): KOAc; Aldrich; MW=98.14; 3.15 equivalents=7.875 mmol=0.77 g (D): Bis(pinacolato)diboron; Aldrich; MW 253.94; 2.05 equivalents=5.125 mmol=1.30 g (E): DMSO; 12 mL A room temperature, heterogeneous mixture of (A), (C) and (D) in (E) was degassed with nitrogen for two minutes. (B) was then added neat, the mixture was capped, warmed to 80° C. for 3 hours, and the mixture was allowed to cool to room temperature. The reaction mixture was partitioned between EtOAc (75 mL) and water (75 mL). The aqueous phase was washed with a second portion of EtOAc. The combined organic phases were then washed with water and then brine (75 mL each). The organic phase was dried over $Na_2SO_4$, filtered and concentrated under reduced pressure to give 1.82 g of crude product as dark brown oil that crystallized upon sitting.

This material was dissolved in ~5 mL of $CH_2Cl_2$ and adsorbed onto a 40 g Isco column. The chromatography employed a gradient eluent system of 20% EtOAc/hexane, held for one minute, then a gradient over 12 minutes to 60% EtOAc/hexane, then held out to 19 minutes. Material eluted between 4.5-9 minutes (30-45% EtOAc). The fractions were concentrated under reduced pressure to give a clear oil. The NMR was consistent with the structure. The product was employed in the next step without further purification.

Step 2

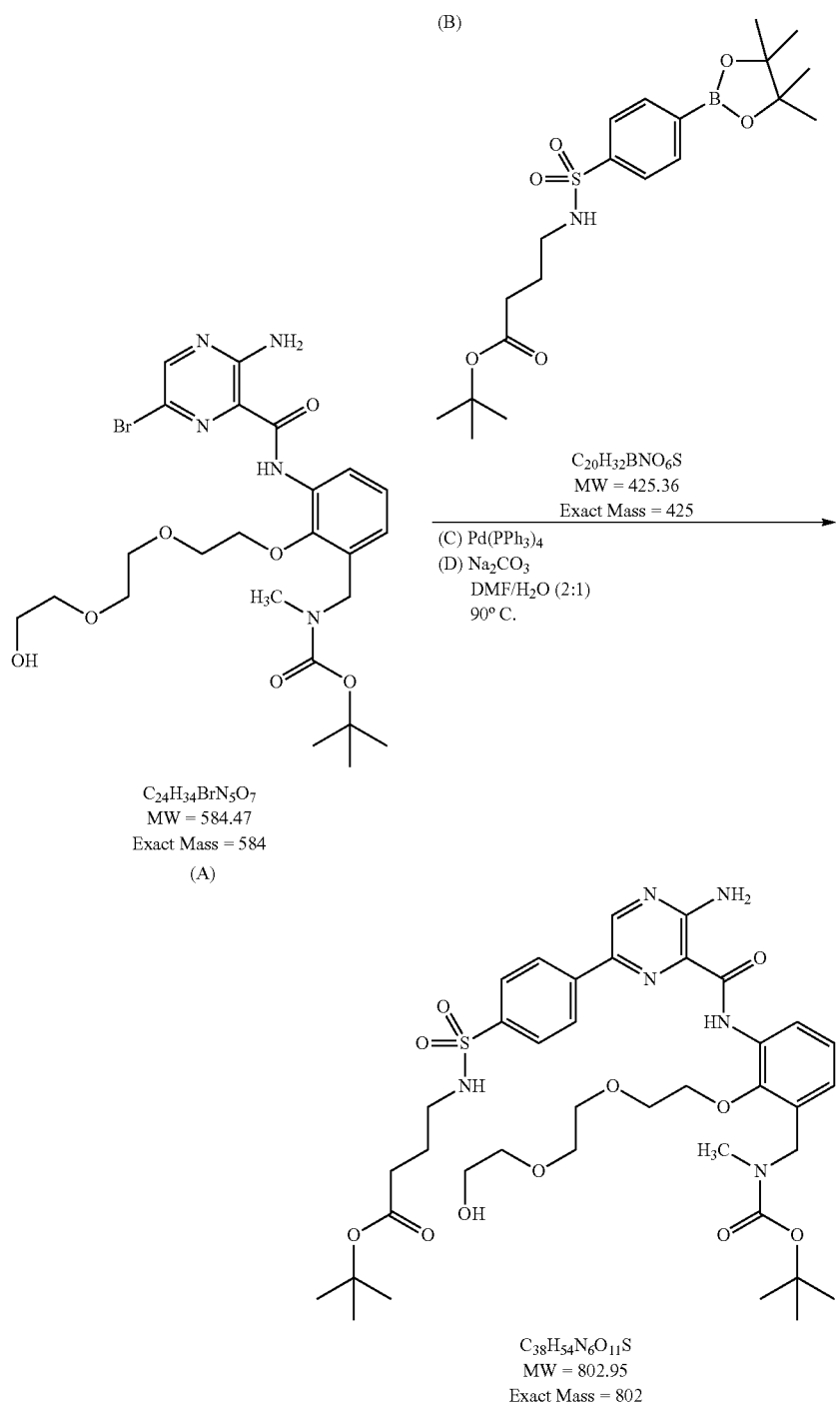

(A): MW=584.47; 0.75 mmol=438 mg (B): MW=425.36; 1.3 equivalent=0.975 mmol=415 mg (C): Pd(PPh₃)₄; MW=1155.57; 0.1 equivalents=0.075 mmol=87 mg (D): 2M Na₂CO₃; 7.5 mL DMF 15 mL In a small pressure reaction vessel, (A) and (B) were mixed with DMF, (D) was added, the solution was capped, the solution as warmed to 85° C. and stirred for 22 hours.

After cooling, an aliquot was partitioned between EtOAc and water and the organic phase was then evaluated by TLC, with 100% EtOAc as eluent. The heterogeneous reaction mixture was partitioned between EtOAc (75 mL) and water (60 mL). The aqueous phase was washed with a second portion of EtOAc (50 mL) and then the combined organic phases were washed sequentially with water (50 mL) and brine (50 mL). The organic phase was dried over Na₂SO₄, filtered and concentrated to give 1.02 g (T.W. 602 mg) of a brown oil. TLC: 100% EtOAc Rf=0.45 as major spot. The sample was dissolved into CH$_2$Cl$_2$ and loaded onto a 12 g column. A gradient system was employed on Isco eluting with 30-100% EtOAc/Hexane system over 16 minutes, where 30% was held for 1 minute, then ramped to 100% by minutes. The relevant fractions were combined, concentrated under reduced pressure and then under high vacuum for 1 hour to yield 420 mg (70%) of a light brown oil. LC/MS (dissolved in CH$_3$CN): rt 4.18 minutes (>95%) (M+H=803.5, consistent with desired product). The oil was used for subsequent step without further purification.

Step 3

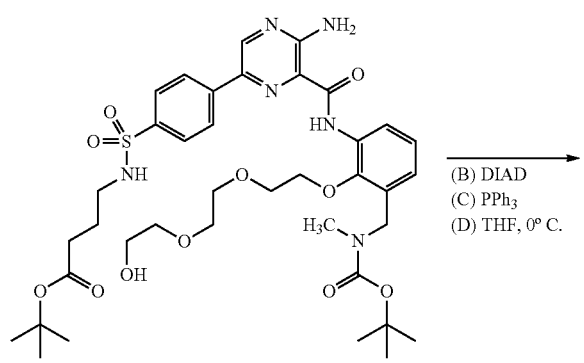

C$_{38}$H$_{54}$N$_6$O$_{11}$S
MW = 802.95
Exact Mass = 802
(A)

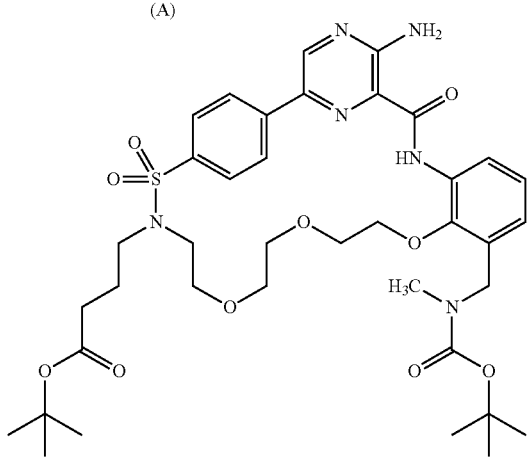

C$_{38}$H$_{52}$N$_6$O$_{10}$S
MW = 784.94
Exact Mass = 784

(A): MW=802.95; 0.50 mmol=401 mg
(B): Diisopropyl azodicarboxylate; MW=202.21; d=1.027 g/mL; 3 equivalent=1.5 mmol=303 mg=295 µL
(C): Triphenylphosphine; MW=262.29; 4 equivalents=2 mmol=525 mg
(D): THF (DriSolv); 10 mL In a reaction vessel, (A) and (C) were dissolved in (D) (5 mL), and at 0° C. the resulting solution was treated with (B) neat dropwise over 30 seconds. After 45 min, the reaction mixture was concentrated under reduced pressure. The residue was dissolved in MeOH (7 mL) and the resulting, stirring solution was diluted with water (12 equivalents=6 mmol=108 µL) followed by AcOH (5 equivalents=2.5 mmol=150 mg=143 µL) at room temperature. A precipitate formed within 1 h. After stirring for additional 2 hours, the precipitate was filtered and rinsed with ice cold MeOH. The solid was air dried overnight and resulted in 197 mg (50%) of product. TLC: 100% EtOAc Rf=0.85, homogenous. LC/MS (dissolved in CH$_3$CN): rt 5.32 minutes (>98%) (M+H=785.4, consistent with desired product). $^1$H NMR (DMSO-d$_6$): Consistent with desired product.

Step 4

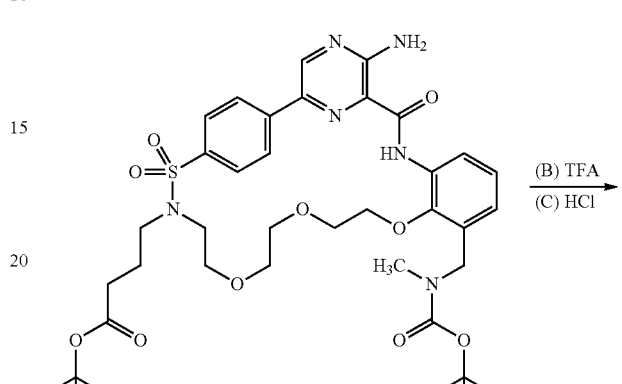

C$_{38}$H$_{52}$N$_6$O$_{10}$S
MW = 784.94
Exact Mass = 784
(A)

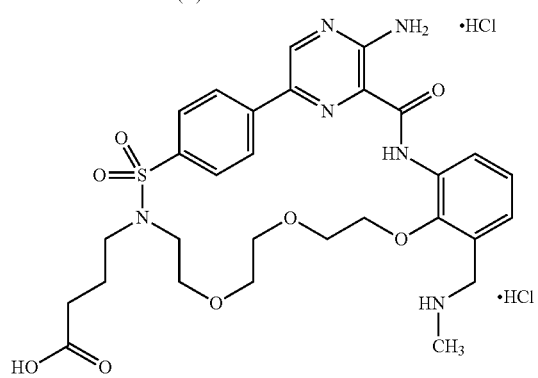

C$_{29}$H$_{36}$N$_6$O$_8$S / 2 HCl
MW = 628.71 / 701.63
Exact Mass = 628

(ATRN-160)
(A): MW=784.94 133 mg=0.17 mmol
(B): TFA; Acros; 3 mL
(C): 3N HCl (A) was dissolved in 0° C. (B) to give a yellow solution. The reaction mixture was removed from the cooling bath after 5 min, allowed to warm to room temperature, brought to dryness, and ultimately dissolved in 3N HCl (4 mL) and some CH$_3$CN. The mixture was lyophilized, resulting in a yellow lyophylate which was dissolved in a 1:1 water/CH$_3$CN mixture, acidified by adding 4 mL of 3N HCl, and re-lyophilized overnight resulting in a yellow solid (73 mg; 61%). LC/MS result (M+H=629.2) was consistent with desired product). LC/MS (MeOH/CH$_3$CN/water) rt 2.78 minutes (M+H=629.2) and $^1$H NMR (DMSO-d$_6$) are consistent with desired carboxylic acid product).

Step 5

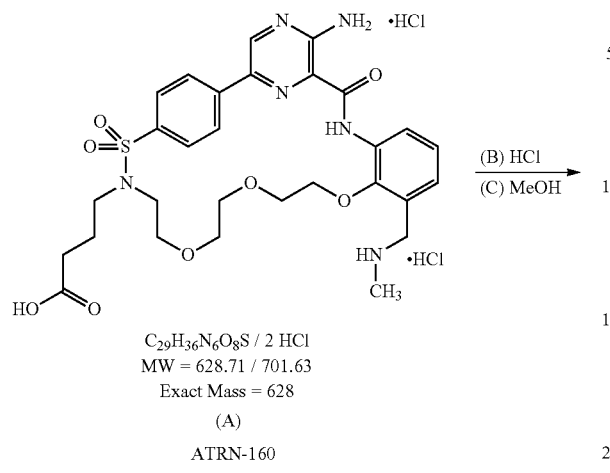

C$_{29}$H$_{36}$N$_6$O$_8$S / 2 HCl
MW = 628.71 / 701.63
Exact Mass = 628
(A)
ATRN-160

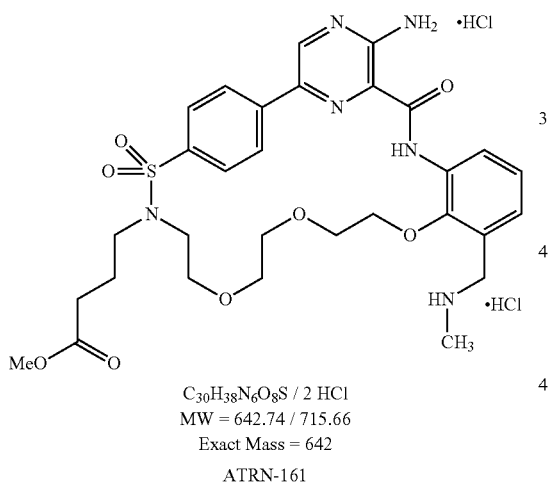

C$_{30}$H$_{38}$N$_6$O$_8$S / 2 HCl
MW = 642.74 / 715.66
Exact Mass = 642
ATRN-161

(A): MW=701.63; 0.066 mmol=46 mg (B): Aldrich; 4 N HCl in Dioxane 2 mL (8 mmol HCl~160 equivalents)

(C): MeOH (Aldrich); 12 mL (A) was combined with (C) and then (B) was added at room temperature to provide the almost homogenous mixture. A solution formed and was stirred overnight at room temperature. The solution was then concentrated under reduced pressure. The residue was treated with EtOAc to yield a yellow solid that was filtered and rinsed liberally with EtOAc. After air drying for 1 h, 26 mg (55%) of yellow solid remained. LC/MS (MeOH/H$_2$O) showed one major peak (>95%) at rt 3.11 minutes (M+H=643.2, consistent with desired product). $^1$H NMR (DMSO-d$_6$) was consistent with the structure.

Example 15: Preparation of ATRN-150

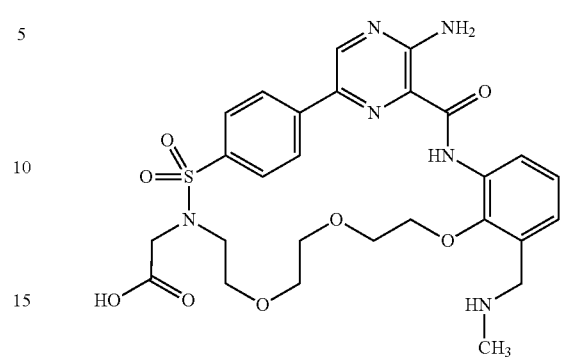

ATRN-150

Step 1

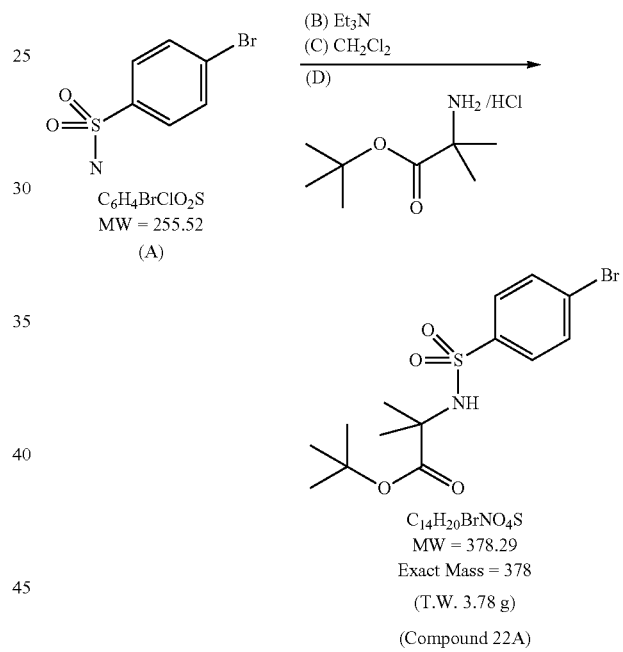

(A): TCI America; MW=255.51; 10 mmol=2.55 g (B): Et$_3$N; MW=101.19; d=0.726; 2.4 equivalents=24 mmol=2.43 g=3.35 mL (C): CH$_2$Cl$_2$ 100 mL (D): α-Aminoisobutyric acid t-butyl ester. HCl (Chem Impex); MW=195.69; 1.05 equivalents=10.5 mmol=2.05 g This step was performed as described in International Patent Application No. 2014146493.

In a reaction vial, (A) was dissolved in (C), (D) was added neat at 0° C. to give an almost homogeneous solution. (B) was then added dropwise, the reaction warmed to room temperature and stirred over the weekend.

The reaction mixture was then washed with 1N HCl (25 mL). The organic phase was then washed with saturated aqueous NaHCO$_3$, dried over Na$_2$SO$_4$, filtered, and concentrated under reduced pressure to give 3.21 g (85%) of white solid.

LC/MS (dissolved in CH$_3$CN): rt 4.72 minutes≥95%; also ~5% impurity at rt 4.47 minutes. TLC: 1:3 EtOAc:hexane Rf=0.8, homogeneous. ¹H NMR (CDCl₃): consistent with structure. Compound 22A was used without further manipulation.

Step 2

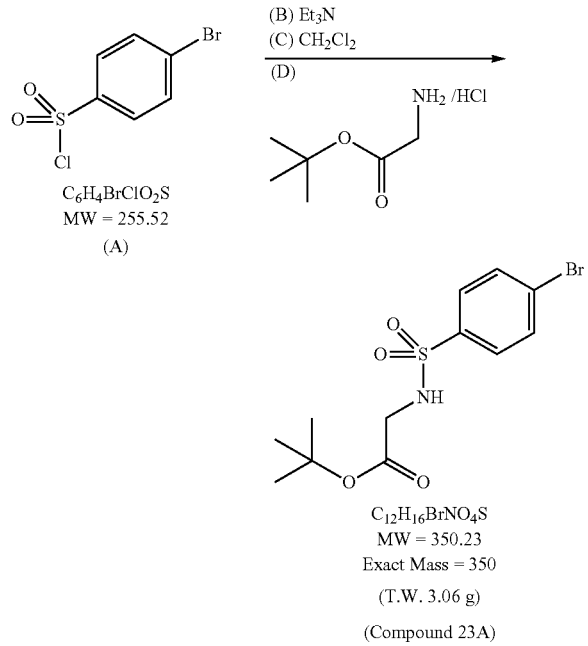

(Compound 23A)

(A): TCI America; MW=255.51 8.75 mmol=2.24 g (B): Et₃N; MW=101.19; d=0.726; 2.4 equivalents=21 mmol=2.12 g=2.92 mL (C): CH₂Cl₂ 100 mL (D): Aldrich; MW=167.64; 1.05 equivalents=9.18 mmol=1.54 g In a reaction vial, (A) was dissolved in (C), (D) was added neat at 0° C. to give an almost homogeneous solution. (B) was then added dropwise, the reaction warmed to room temperature and stirred overnight.

The reaction mixture was washed with 1N HCl (25 mL). The organic phase was then washed with saturated aqueous NaHCO₃, dried over Na₂SO₄, filtered, and concentrated under reduced pressure to give 3.04 g (99%) of white solid of Compound 23A. LC/MS (dissolved in CH₃CN): rt 4.22 minutes≥95%. TLC: 1:3 EtOAc:hexane Rf=0.5, homogeneous. ¹H NMR (CDCl₃): consistent with structure, trace of CH₂Cl₂ remains. Compound 23A was used without further manipulation.

Step 3

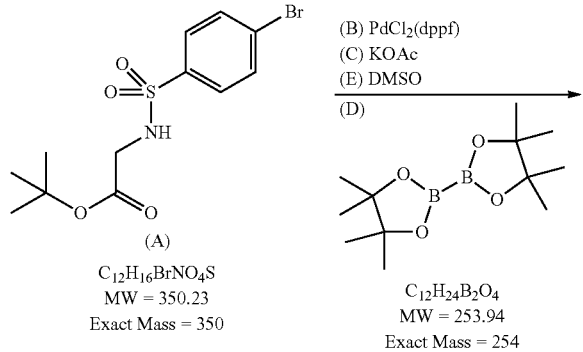

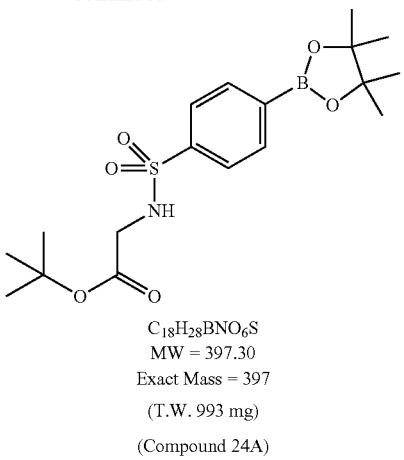

(Compound 24A)

(A): Compound 23A; MW=350.23; 2.5 mmol=0.88 g (B): [1,1'-bis(diphenyphosphino)-ferrocene]dichloropalladium (II) complex with dichloromethane (1:1); PdCl₂(dppf); Aldrich; MW=816.63; 0.065 equivalents=0.1625 mmol=0.13 g (C): KOAc; Aldrich; MW=98.14; 3.15 equivalents=7.875 mmol=0.77 g (D): bis(pinacolato)diboron; Aldrich; MW=253.94; 2.05 equivalents=5.125 mmol=1.30 g (E): DMSO; 12 mL This step was performed as described in U.S. Patent Application Publication No. 20050143422.

A room temperature, a heterogeneous mixture of (A), (C) and (D) in (E) was degassed with nitrogen for two minutes, (B) was added neat, the mixture was capped and warmed to 80° C. After several hours, the sample was removed from the heat and let cool to room temperature.

The reaction mixture was partitioned between EtOAc (75 mL) and brine (75 mL). The organic phase was washed with brine twice more (75 mL each). The organic phase was dried over Na₂SO₄, filtered and concentrated under reduced pressure to give 2.50 g of crude product as a dark brown solid. This material was dissolved in ~5 mL of CH₂Cl₂ and adsorbed onto a 40 g Isco column. A gradient eluent system of 0% EtOAc/hexane was ran, held one minute; a gradient over 16 minutes to 40% EtOAc/hexane was then ran, then held out to 21 minutes. A major peak came out between 10 minutes (25% EtOAc at that point F2) and 13 minutes (35% EtOAc; F6). These fractions were evaluated by TLC and proved consistent with Rf=0.4 in 1:3 EtOAc:hexane. These fractions were combined and concentrated under reduced pressure to give 0.97 g (98%) of white solid of Compound 24A. LC/MS (dissolved in CH₃CN). TLC: 1:3 EtOAc:hexane Rf=0.4, homogeneous. ¹H NMR (CDCl₃): consistent with desired product, with 2/3 eqvt EtOAc. Compound 24A was used for subsequent step without further manipulation.

Step 4

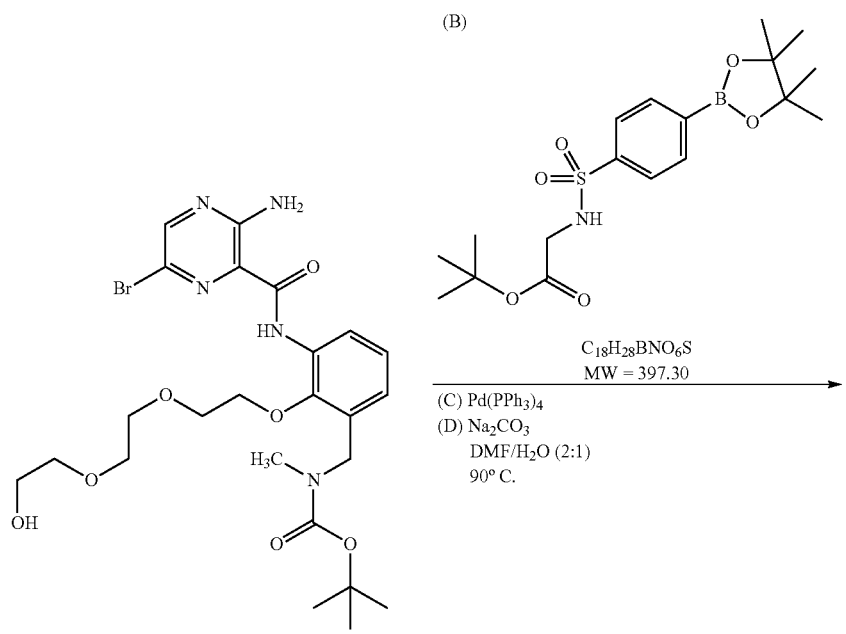

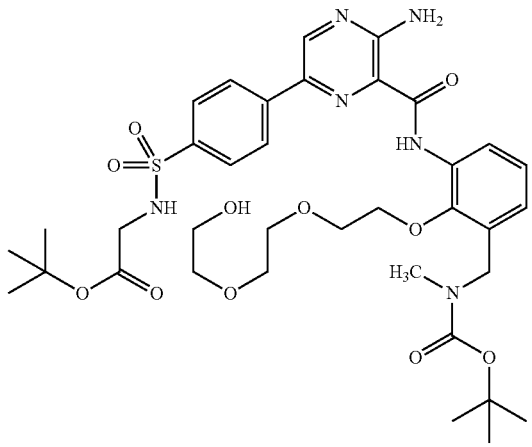

(Compound 26B)

(A): Compound 7b from Example 12; MW=584.47; 0.75 mmol=438 mg
(B): 1.3 equivalent=0.975 mmol=387 mg
(C): Pd(PPh$_3$)$_4$; Strem; MW=1155.57; 0.1 equivalents=0.075 mmol=87 mg
(D): 2M Na$_2$CO$_3$; 7.5 mL
DMF; Acros; 15 mL This step was performed following the procedure of *J. Med. Chem.*, 2011, 54, 2320-2330

In a small pressure reaction vessel, (A) and (B) were mixed with DMF, (D) was added and the solution degassed under a stream of N$_2$ for 2 minutes. Solid then started to precipitate. Under nitrogen, (C) was added, the vessel was capped and warmed to 85° C. After several hours, the reaction mixture was removed from heat, and cooled. The vessel was then placed back onto heat at 85° C. and heated overnight.

The sample was removed from the heat. After cooling, the heterogeneous reaction mixture was partitioned between EtOAc (75 mL) and water (60 mL). The aqueous phase was washed with a second portion of EtOAc (50 mL) and then the combined organic phases were washed sequentially with water (50 mL) and brine (50 mL). The organic phase was dried over Na$_2$SO$_4$, filtered and concentrated to give 480 mg of a brown oil of Compound 26A. TLC: 100% EtOAc— consistent with desired product. LC/MS (dissolved in CH₃CN): ~70% at rt 4.97 minutes (M+H=775.4, consistent with desired product).

The material was loaded onto a 12 g column with EtOAc and ran a gradient system on Isco eluting with 30-100% EtOAc/Hexane system over 18 minutes, where 100% was reached at 8 minutes. The purest fractions were combined and concentrated under reduced pressure to yield 160 mg (28%) of a yellow glass. TLC (dissolved in THF): 100% EtOAc Rf=0.55, homogeneous. LC/MS (dissolved in CH₃CN): rt 4.89 minutes (~90%) (M+H=775.4, consistent with desired product). Compound 26B was used for the subsequent step without further manipulation.

Step 5

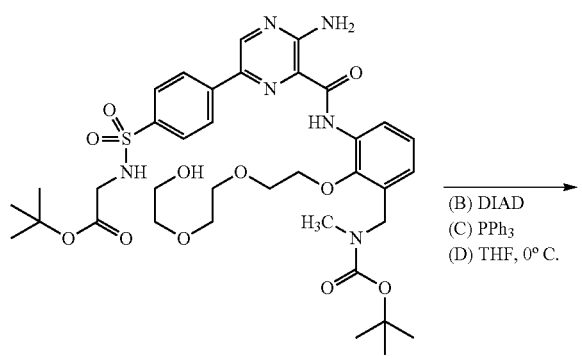

$C_{36}H_{50}N_6O_{11}S$
MW = 774.90
Exact Mass = 774
(A)

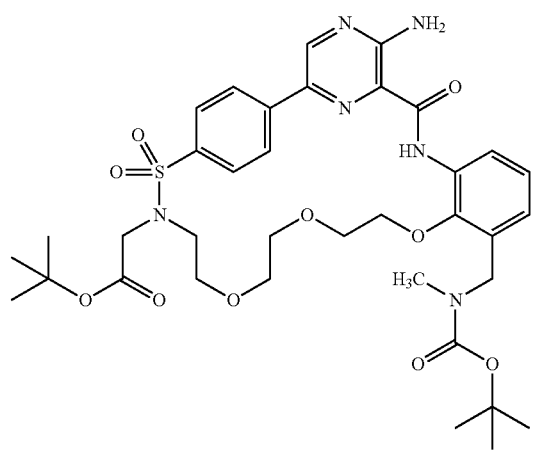

$C_{36}H_{48}N_6O_{10}S$
MW = 756.88
Exact Mass = 756
(T.W. 156 mg)
(Compound 27B)

(A): Compound 26B; MW=774.90; 0.206 mmol=160 mg
(B): diisopropyl azodicarboxylate; Acros; MW=202.21; d=1.027 g/mL; 3 equivalent=0.62 mmol=125 mg=122 µL (C): Triphenylphosphine; Alfa Aesar; MW=262.29; 4 equivalents=0.83 mmol=217 mg (D): THF; DriSolv In a reaction vessel, (A) and (C) were dissolved in (D) (3 mL), and at 0° C. the resulting solution was treated with (B) neat dropwise over 30 seconds. The reaction was warmed to room temperature. Thereafter, the reaction mixture was concentrated under a stream of nitrogen. The residue was dissolved in MeOH (3 mL) and the resulting, stirring solution was diluted with water (12 equivalents=2.48 mmol=45 µL) followed by AcOH (MW 60.05, d=1.049; 5 equivalents=1.03 mmol=62 mg=59 µL) at room temperature. Several hours later, extra equivalents of water and AcOH were added. About one hour later, an aliquot of the reaction was taken, diluted with MeOH and ran a TLC and LC/MS. LC/MS: rt 5.60 minutes (~50%) (M+H=757.3, consistent with desired product). One hour later, the mixture was placed in a 4° C. refrigerator and let sit overnight.

The mixture was blown to dryness, CH₂Cl₂ added, dried over Na₂SO₄, filtered and the solution loaded onto a 20 g Isco silica gel column. A gradient EtOAc/hexane system was rn, starting at 25%, holding for 1 minute, then ramping to 60% over 12 minutes, then held for 6 minutes. Fractions 4 and 5 were combined and concentrated under reduced pressure to give 40 mg of yellow glass of Compound 27B. TLC: 1:1 EtOAc:hexane Rf=0.35, homogeneous. LC/MS: rt 4.05 minutes (~2%) (M+H=279=Ph₃P=O), rt 5.64 minutes (~98%) (M+H=757.3, consistent with desired product). ¹H NMR (CDCl₃): Consistent with desired product.

Step 6

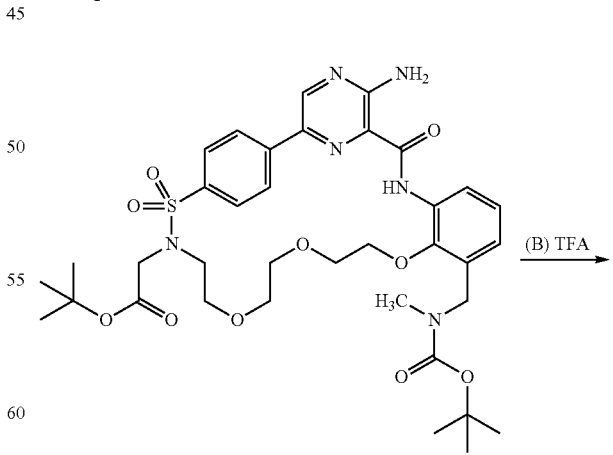

(A)
$C_{36}H_{48}N_6O_{10}S$
MW = 756.88
Exact Mass = 756

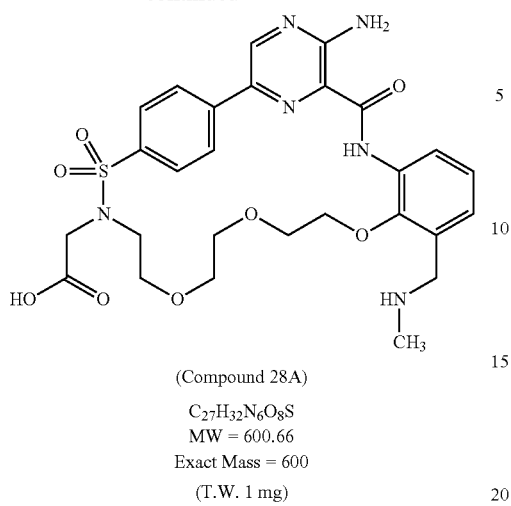

(Compound 28A)

$C_{27}H_{32}N_6O_8S$
MW = 600.66
Exact Mass = 600
(T.W. 1 mg)

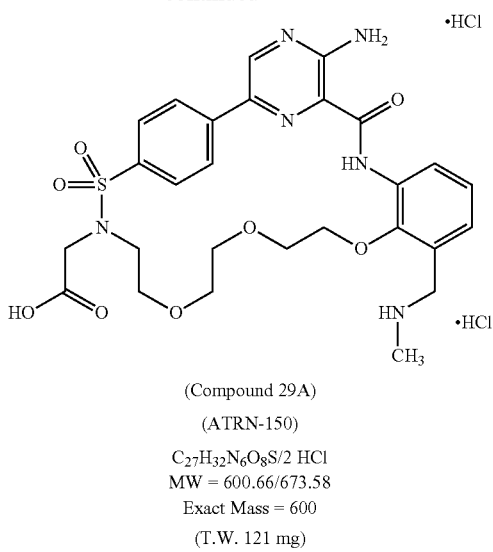

(Compound 29A)
(ATRN-150)
$C_{27}H_{32}N_6O_8S/2$ HCl
MW = 600.66/673.58
Exact Mass = 600
(T.W. 121 mg)

(A): Compound 27B MW 756.88 used ~1 mg (B): TFA 2 drops

In a small vial, (A) was dissolved in (B) to give a yellow solution. About one hour later, the reaction mixture was blown to dryness and some $CH_3CN$ was added, followed by some $H_2O$. LC/MS: rt 3.01 minutes (~98%) (M+H=601.2, consistent with desired product), rt 4.05 minutes (~2%) (M=279.1, consistent with $Ph_3P=O$, from prior reaction).

(A): Compound 27C; MW 756.88; 140 mg of crude material (0.18 mmol)

(B): TFA; 3 mL

In a small vial, (A) was dissolved in (C) to give a yellow solution. Shortly thereafter, the reaction mixture was blown to dryness and DMSO (1.5 mL) was added to dissolve residue for purification on the Gilson. The material was run over two runs (0.75 mL each) with a gradient of 10:50. The desired fractions were combined, concentrated a bit to remove most of $CH_3CN$ and then lyophylized over the weekend. LC/MS of both crude (~75:25 product:$Ph_3P=O$ from previous step). For crude, the desired product came out at rt 3.00 minutes (M+H=601.2, consistent with desired product) The Gilson purified material came off clean at 3.01 minutes (M+H=601.21, consistent for desired product).

The fluffy, statical yellow lyophylate was dissolved in ~3 mL of concentrated HCl, then 6 mL of water was added, the mixture frozed and retained on the lyophylizer. Thereafter, the material had a different consistency as a yellow lyophylate. Ran an LC/MS to confirm that product is fine (dissolved in $CH_3CN$/water mix).

Compound 29B was dissolved in >40 mL of a $CH_3CN$/1N HCl mix, placed on lyophylizer after freezing, and lyophylized overnight to provide a yellow lyophylate as compound 29C. Analysis of compound 29C: LC/MS (dissolved in DMSO): clean at rt 3.03 minutes (M+H=601.2, consistent with desired product); $^1H$ NMR (DMSO-$d_6$): Consistent with desired product.

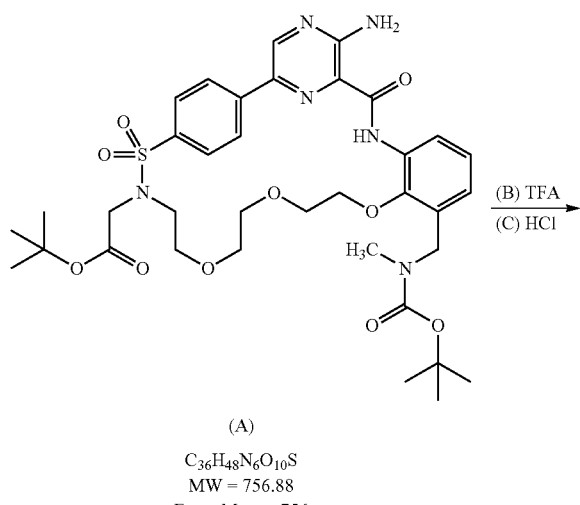

(A)

$C_{36}H_{48}N_6O_{10}S$
MW = 756.88
Exact Mass = 756

Example 16

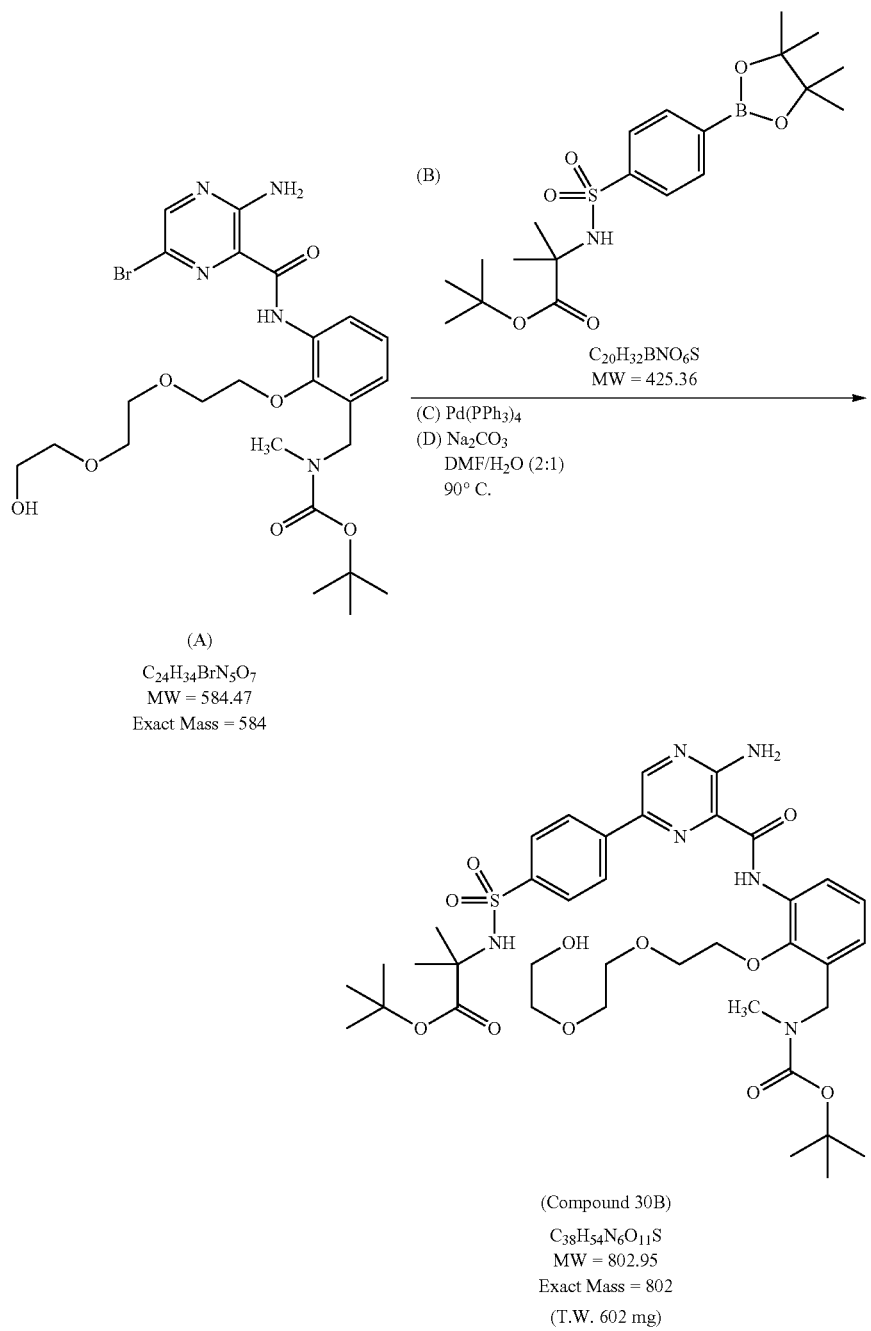

(A): Compound 7b from Example 12; MW=584.47; 0.75 mmol=438 mg (B): Compound 25A; MW=425.36; 1.5 equivalent=1.125 mmol=479 mg (C): Pd(PPh$_3$)$_4$; Strem; MW=1155.57; 0.1 equivalents=0.075 mmol=87 mg (D): 2M Na$_2$CO$_3$ 7.5 mL DMF (Acros) 15 mL This example was performed using part of all of the procedures described in *J. Med. Chem* 2011, 54, 2320-2330.

In a small pressure reaction vessel, (A) and (B) were mixed with DMF, (D) was added and the solution degassed under a stream of N$_2$ for 2 minutes. Under nitrogen, (C) was added, the mixture was capped, warmed to 85° C., and heated overnight.

The sample was removed from the heat and, after cooling, an aliquot was evaluated by TLC. Took a sample of the aliquot, blew to dryness, dissolved in CH$_3$CN and ran a LC/MS. Major peak at rt 5.21 minutes (~80%) (M+H=803.4, consistent with desired product. The heterogeneous reaction mixture was partitioned between EtOAc (75 mL) and water (60 mL). The aqueous phase was washed with a second portion of EtOAc (50 mL) and then the combined organic phases were washed sequentially with water (2×50 mL) and brine (50 mL). The organic phase was dried over Na$_2$SO$_4$, filtered and concentrated to give 950 mg of a brown oil of Compound 30A. TLC: 100% EtOAc same as above. The material was loaded onto a 20 g column with CH$_2$Cl$_2$ and a gradient system was run on Isco eluting with 30-100% EtOAc/hexane system over 18 minutes, where 100% was reached at 11 minutes. Initially kept at 30% EtOAc for 1 minute. The purest fractions were combined and concentrated under reduced pressure to yield 380 mg (63%) of a orange glass of Compound 30B. TLC (dissolved in THF): 100% EtOAc Rf=0.55, homogeneous. Compound 30B was used for subsequent steps without further manipulation.

Example 17

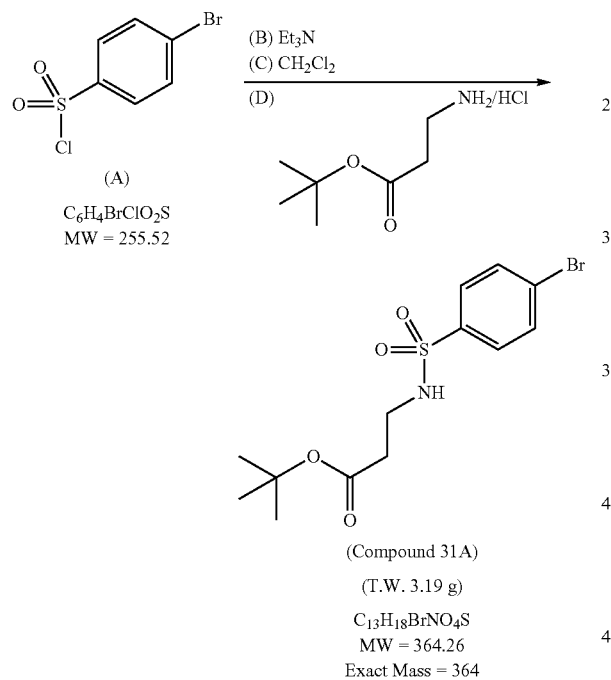

(Compound 31A)
(T.W. 3.19 g)
C$_{13}$H$_{18}$BrNO$_4$S
MW = 364.26
Exact Mass = 364

(A): TCI America; MW=255.51; 8.75 mmol=2.24 g
(B): Et$_3$N; MW=101.19; d=0.726; 2.4 equivalents=21 mmol=2.12 g=2.92 mL
(C): CH$_2$Cl$_2$; 100 mL
(D): Combi-Blocks; MW=181.66; 1.05 equivalents=9.18 mmol=1.67 g In a reaction vial, (A) was dissolved in (C). At 0° C., (D) was added neat to give an almost homogeneous solution. (B) was then added dropwise, the reaction warmed to room temperature and stirred overnight. The reaction mixture was then washed with 1N HCl (25 mL). The organic phase was then washed with saturated aqueous NaHCO$_3$, dried over Na$_2$SO$_4$, filtered, and concentrated under reduced pressure to give a clear oil, which was placed under vacuum overnight.

The sample was then placed under high vacuum for 1 hour. Left with 3.27 g (T.W. 3.19 g) of clear oil of Compound 31A. LC/MS (dissolved in CH$_3$CN): rt 4.58 minutes≥95%, also ~5% impurity at rt 4.37 minutes. TLC: 1:3 EtOAc:hexane Rf=0.5, homogeneous. $^1$H NMR (CDCl$_3$): consistent with structure. Compound 31A was used without further manipulation.

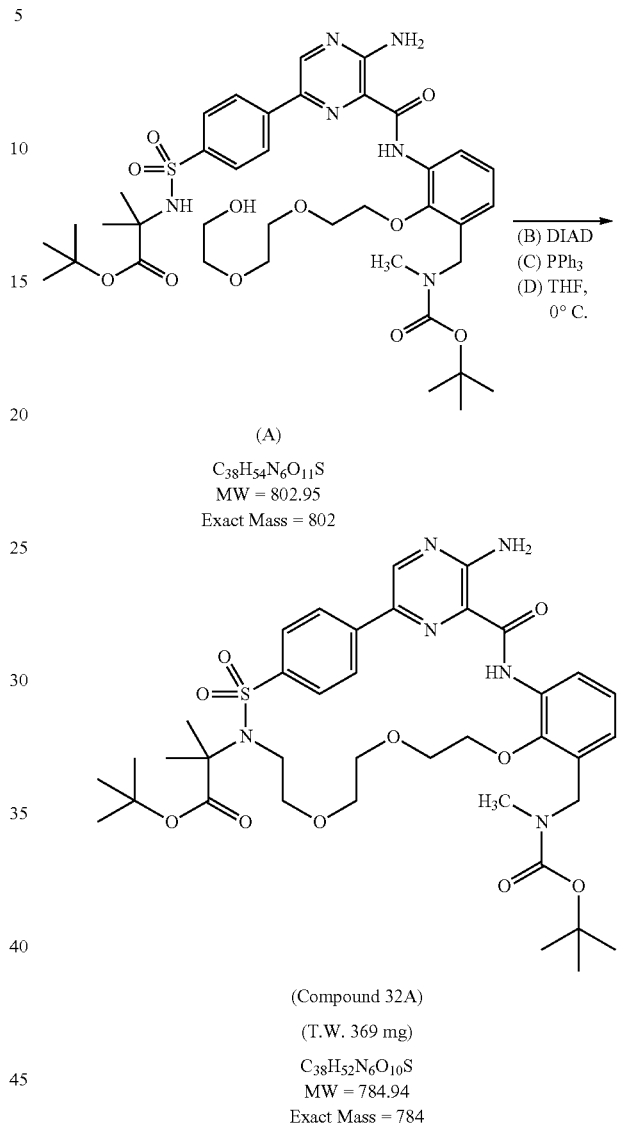

(A)
C$_{38}$H$_{54}$N$_6$O$_{11}$S
MW = 802.95
Exact Mass = 802

(Compound 32A)
(T.W. 369 mg)
C$_{38}$H$_{52}$N$_6$O$_{10}$S
MW = 784.94
Exact Mass = 784

(A): Compound 30B MW 802.95 0.47 mmol=380 mg
(B): Diisopropyl azodicarboxylate (Acros) MW 202.21 d=1.027 g/mL 3 equivalent=1.42 mmol=287 mg=280 µL
(C): Triphenylphosphine (Alfa Aesar) MW=262.29 4 equivalents=1.89 mmol=497 mg
(D): THF (Acros)

In a reaction vessel, (A) and (C) were dissolved in (D) (10 mL), and at 0° C. the resulting solution was treated with (B) neat dropwise over 30 seconds. About 10 minutes later, the reaction was warmed to room temperature. After about an hour, the reaction mixture was concentrated under a stream of nitrogen and the residue dissolved in MeOH (5 mL) and the resulting, stirring solution was diluted with water (12 equivalents=5.64 mmol=102 µL) followed by AcOH (MW 60.05, d=1.049) (5 equivalents=2.35 mmol=141 mg=135 µL) at room temperature. Several hours later, the homogeneous solution was placed in a 4° C. fridge and let sit overnight.

The mixture was then blown to dryness and will work up as time permits.

Dissolved oil in ~10 mL of EtOAc and extracted with saturated aqueous NaHCO₃. The organic phase was dried over Na₂SO₄, filtered and concentrated under reduced pressure. The residue was dissolved in ~4 mL of CH₂Cl₂ and loaded resulting solution onto a 20 g Isco silica gel column (as appears will be a tough separation); TLC: 1:1 EtOAc: hexane Rf=solvent front for one spot, Rf=0.35, the new spot, Rf=0.2 (confirmed as Ph₃P=O by cospot), spot at origin (also consistent with SM A); 100% EtOAc Rf=solvent front, Rf=0.85, new spot, Rf=0.5 (Ph₃P=O as confirmed by co-spot), and also Rf=0.5 (SM A, as confirmed by co-spot). Ran a gradient EtOAc/hexane system, starting at 20%, holding for 1 minute, and then ramping to 65% over 11 minutes, then held for 4 minutes. On inspection, only F4-6 were relatively clean, with F7 around 50:50 with Ph₃P=O and after that mostly Ph₃P=O. Combined F4-6 and concentrated under reduced pressure to give 250 mg (68%) of yellow oil of Compound 27B. This material was dissolved in ~2 mL of MeOH and let sit in ice bath for 1 hour. Saw solid slowly began to precipitate, consistent with reference reaction. Scratching caused more material to crystallize. After sitting an additional hour in an ice bath, the resulting solid was filtered and rinsed with 2 mL of ice cold MeOH. After air drying there remained 122 mg (33%) of yellow solid as Compound 32A. The filtrate was stored in the 4° C. fridge overnight. Analysis of Compound 32A: TLC: 1:1 EtOAc: hexane Rf=0.5, homogeneous. LC/MS (dissolved in CH₃CN): rt 5.84 minutes (virtually clean) (M+H=785.5, consistent with desired product, stronger M+23=807.5).

1H NMR (CDCl₃): Consistent with desired product. Compound 32A was used for subsequent steps without further manipulation.

Example 18

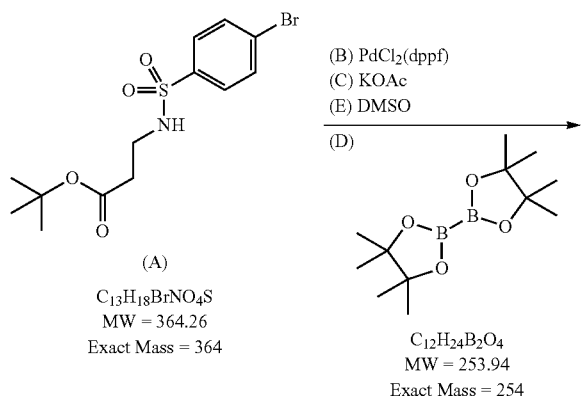

(A)
C₁₃H₁₈BrNO₄S
MW = 364.26
Exact Mass = 364

(B) PdCl₂(dppf)
(C) KOAc
(E) DMSO
(D)

C₁₂H₂₄B₂O₄
MW = 253.94
Exact Mass = 254

-continued

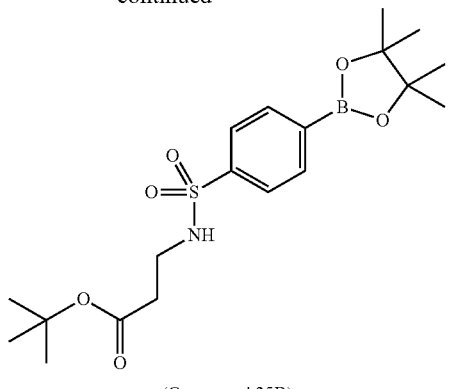

(Compound 35B)
(T.W. 1.03 g)
C₁₉H₃₀BNO₆S
MW = 411.33
Exact Mass = 411

(A): Compound 31A MW 364.26 2.5 mmol=0.91 g (B): [1,1'-Bis(diphenyphosphino)-ferrocene]dichloropalladium (II) complex with dichloromethane (1:1) PdCl₂ (dppf) (Aldrich) MW 816.63 0.065 equivalents=0.1625 mmol=0.13 g (C): KOAc (Aldrich) MW 98.14 3.15 equivalents=7.875 mmol=0.77 g (D): Bis(pinacolato)diboron (Aldrich) MW 253.94 2.05 equivalents=5.125 mmol=1.30 g (E): DMSO 12 mL Some or all of this example was performed using the procedure of U.S. Patent Application Publication No. 20050143422.

A room temperature, heterogeneous mixture of (A), (C) and (D) in (E) was degassed with nitrogen for two minutes, then (B) was added neat, the mixture was capped and warmed to 80° C. After 3 hours, the sample was removed from the heat and let cool to room temperature. Took an aliquot of the reaction mixture and partitioned between EtOAc and water. Took organic and ran a TLC. This organic sample was blown to dryness, dissolved in CH₃CN and ran an LC/MS.

The reaction mixture was partitioned between EtOAc (75 mL) and water (75 mL). The organic phase was then washed with brine twice (75 mL each). The organic phase was dried over Na₂SO₄, filtered and concentrated under reduced pressure to give 2.46 g of crude product as dark brown oil. This material was dissolved in ~5 mL of CH₂Cl₂ and adsorbed onto a 40 g Isco column. Ran a gradient eluent system of 20% EtOAc/hexane, held one minute, then a gradient over 12 minutes to 60% EtOAc/hexane, then held out to 19 minutes. Material came off between 3.5-8 minutes (F6-13; 30-45% EtOAc) and also a major peak between 10-12.5 minutes (F14-17; 55-60% EtOAc).

The purest earlier fractions were concentrated under reduced pressure to give a clear oil, which crystallized to a white solid on sitting of Compound 35B and amounted to 760 mg (74%). The 1H NMR (CDCl₃) spectrum was consistent for the desired product. The latter running fractions were also concentrated and yielded ~100 mg of whitish solid of Compound 35C. LC/MS showed >90% at rt 4.77 minutes (M+H=499). Compound 35B was used for subsequent steps without further manipulation.

Example 19

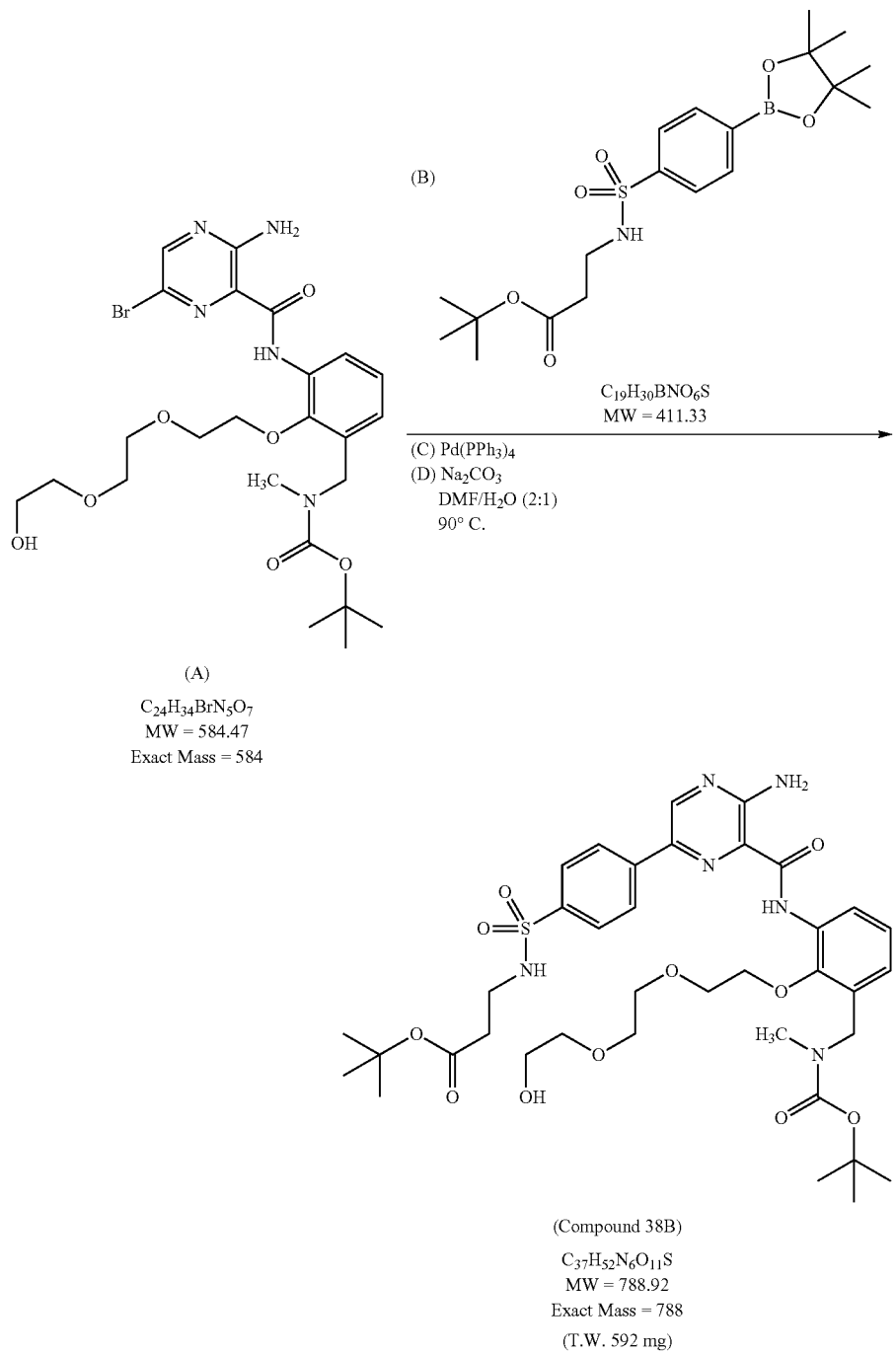

(A): Compound 7b from Example 121; MW 584.47 0.75 mmol=438 mg
(B): Compound 35B MW 411.33 1.3 equivalent=0.975 mmol=401 mg
(C): Pd(PPh$_3$)$_4$ (Strem) MW=1155.57 0.1 equivalents=0.075 mmol=87 mg
(D): 2M Na$_2$CO$_3$ 7.5 mL
DMF (Acros) 15 mL Some or all of this example was performed using the procedure of *J. Med. Chem* 2011, 54, 2320-2330

In a small pressure reaction vessel, (A) and (B) were mixed with DMF, then (D) was added and the solution was capped and warmed to 85° C. (5 PM) overnight.

The sample was then removed from the heat. After cooling, an aliquot was partitioned between EtOAc and water and the organic phase was then evaluated by TLC. An additional portion of (B) was added (20 mg) and the mixture was capped and warmed again to 85° C.

The heat was removed from the reaction and then the heterogeneous reaction mixture was partitioned between EtOAc (75 mL) and water (60 mL). The aqueous phase was washed with a second portion of EtOAc (50 mL) and then the combined organic phases were washed sequentially with water (50 mL) and brine (50 mL). The organic phase was dried over Na$_2$SO$_4$, filtered and concentrated to give 800 mg (T.W. 592 mg) of a brown oil of Compound 38A. TLC: 100% EtOAc Rf=0.45 as major spot, with somewhat large impurity at Rf=0.2 (streaky), and minor impurities at Rf=solvent front, 0.95 and origin. The sample was dissolved into CH$_2$Cl$_2$ and loaded onto a 12 g column. Ran a gradient system on Isco eluting with 30-100% EtOAc/Hexane system over 16 minutes, where 30% was held for 1 minute, then ramped to 100% by minutes. Major peak came off between 8.5 minutes and 13 minutes (F8-12). On TLC examination, F9-12 proved the cleanest by TLC, so combined these purest fractions and concentrated under reduced pressure and then under high vacuum for 1 hour to yield 230 mg (39%) of a yellow oil of Compound 38B. TLC (dissolved in EtOAc): 100% EtOAc Rf=0.65, homogeneous. LC/MS (dissolved in CH$_3$CN): rt 4.95 minutes (~95%) (M+H=789.4, consistent with desired product) and rt 4.02 minutes (~5%) (Ph$_3$P=O). Compound 38B was used for subsequent step without further manipulation.

(A): Compound 38B; MW=788.92; 0.29 mmol=230 mg
(B): Diisopropyl azodicarboxylat; Acros; MW=202.21; d=1.027 g/mL; 3 equivalent=0.87 mmol=176 mg=171 µL
(C): Triphenylphosphine; Alfa Aesar; MW=262.29; 4 equivalents=1.16 mmol=304 mg
(D): THF; DriSolv In a reaction vessel, (A) and (C) were dissolved in (D) (5 mL), and at 0° C. the resulting solution was treated with (B) neat dropwise over 30 seconds. After 30 minutes, the reaction mixture was concentrated under a stream of nitrogen. The residue was dissolved in MeOH (4 mL) and the resulting, stirring solution was diluted with water (12 equivalents=3.48 mmol=62 µL) followed by AcOH (MW 60.05, d=1.049) (5 equivalents=1.45 mmol=87 mg=83 µL) at room temperature. The mixture was cooled for 1 hour, filtered and rinsed with ice cold MeOH. After air during, 120 mg (54%) of yellow solid of Compound 41A remained. Analysis of Compound 41A: TLC: 1:1 EtOAc:hexane Rf=0.35, homogeneous; 100% EtOAc Rf=0.85, homogenous. LC/MS (dissolved in CH$_3$CN): rt 5.66 minutes (>98%) (M+H=771.5, consistent with desired product). $^1$H NMR (CDCl$_3$): Consistent with desired product. Compound 41A was used for subsequent step without further manipulation.

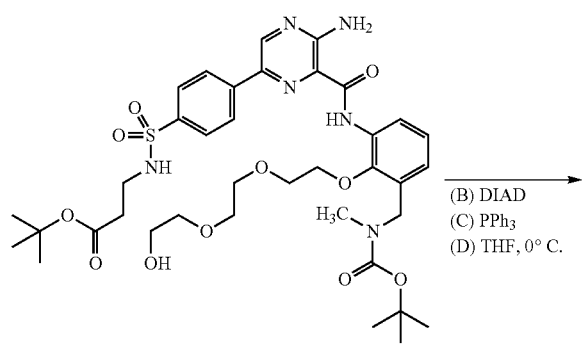

(A)

C$_{37}$H$_{52}$N$_6$O$_{11}$S
MW = 788.92
Exact Mass = 788

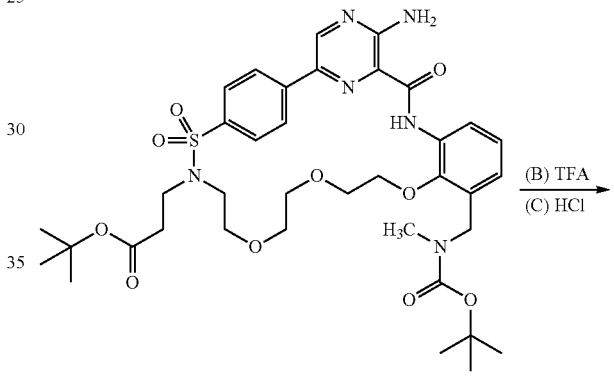

(A)

C$_{37}$H$_{50}$N$_6$O$_{10}$S
MW = 770.91
Exact Mass = 770

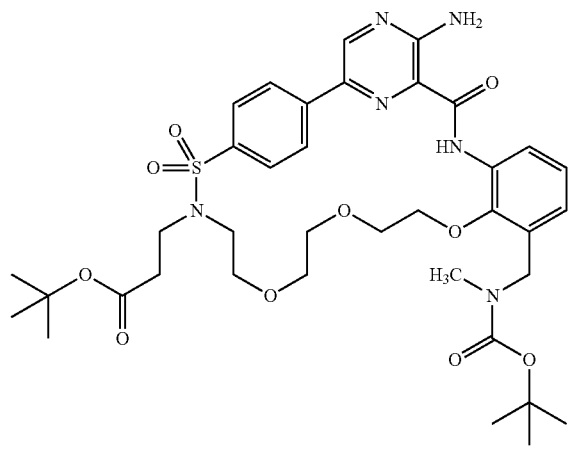

(Compound 41A)

C$_{37}$H$_{50}$N$_6$O$_{10}$S
MW = 770.91
Exact Mass = 770

(T.W. 224 mg)

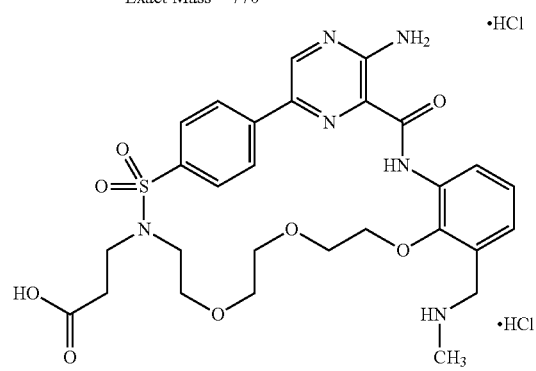

(Compound 42A)

C$_{28}$H$_{34}$N$_6$O$_8$S/2 HCl
MW = 614.68/687.60
Exact Mass = 614

(T.W. 96 mg)

(A): Compound 41A; MW=770.91; 110 mg=0.14 mmol
(B): TFA; Acros; 3 mL
(C): 3N HCl In a small vial, (A) was dissolved in 0° C. (B) to give a yellow solution (9:45 AM). The reaction was then removed from cooling bath and warmed to room temperature. About 1 hour later, the reaction mixture was blown to dryness, some 3N HCl was added, and lyophilized. The LC/MS was consistent with desired product). Several hours later, a yellow solid lyophylate was obtained, re-dissolved in a CH$_3$CN/2N HCl solution, and lyophilized again overnight.

Left with 78 mg (81%) of a yellow lyophylate of Compound 42A (ATRN-151-A). Analysis of Compound 42A: LC/MS: clean at rt 3.44 minutes (M+H=615.2, consistent with desired product); $^1$H NMR (DMSO-d$_6$): Consistent with desired product.

Example 20

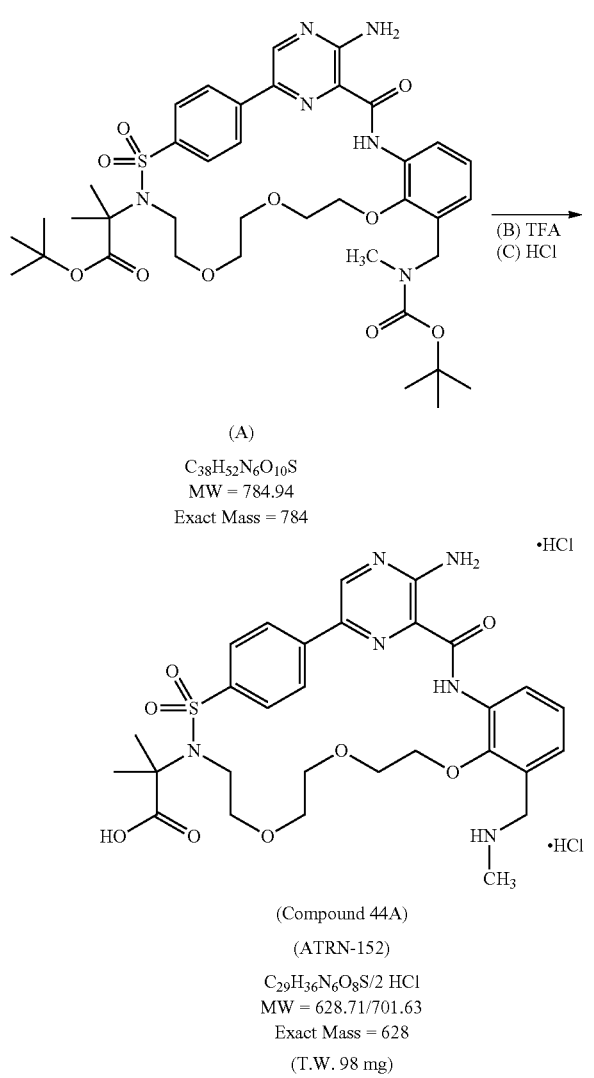

(A)
C$_{38}$H$_{52}$N$_6$O$_{10}$S
MW = 784.94
Exact Mass = 784

(Compound 44A)
(ATRN-152)
C$_{29}$H$_{36}$N$_6$O$_8$S/2 HCl
MW = 628.71/701.63
Exact Mass = 628
(T.W. 98 mg)

(A): Compound 32A; MW=784.94; 110 mg=0.14 mmol
(B): TFA; Acros; 3 mL
(C): 3N HCl In a small vial, (A) was dissolved in (B) at room temperature to give a yellow solution. A little more than 1 hour later, the reaction mixture was blown to dryness under a stream of nitrogen and some 3N HCl (4 mL) added to give a heterogeneous mixture. This mixture was diluted with portions of CH$_3$CN and water to give a more homogenous mixture. With slight warming a homogeneous mixture was attained, then after freezing lyophilized overnight to provide a yellow lyophylate. The yellow lyophylate was dissolved in ~15 mL of 1:1 CH$_3$CN/water (with very gentle heating), added 2 mL of 1 N HCl, froze and lyophilized overnight. Left with 86 mg (88%) of a yellow lyophylate of Compound 44A (ATRN-152-A). Analysis of 44A: LC/MS (dissolved in DMSO): rt 3.44 minutes (>95%) (M+H=629.4, consistent with desired product); $^1$H NMR (DMSO-d6): Consistent with desired product.

Example 21

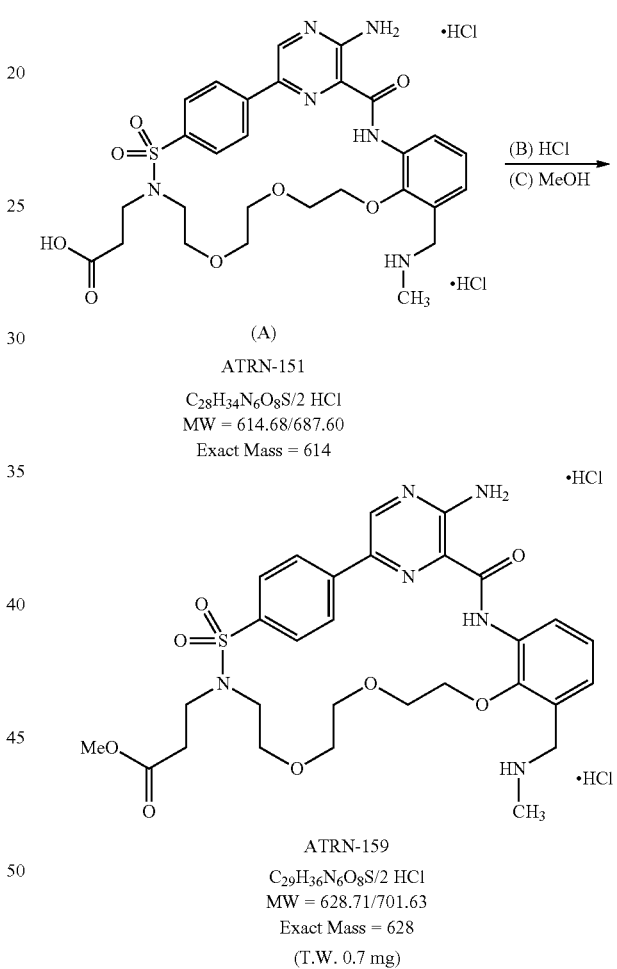

(A)
ATRN-151
C$_{28}$H$_{34}$N$_6$O$_8$S/2 HCl
MW = 614.68/687.60
Exact Mass = 614

ATRN-159
C$_{29}$H$_{36}$N$_6$O$_8$S/2 HCl
MW = 628.71/701.63
Exact Mass = 628
(T.W. 0.7 mg)

(A): Compound 42A (ATRN-151A); MW 687.60; 0.001 mmol=0.7 mg
(B): Aldrich; 4 N HCl in Dioxane 70 µL (0.28 mmol HCl~70 equivalents)
(C): MeOH; Aldrich; 0.25 mL (A) was combined with (C) and then (B) was added at room temperature to the almost homogenous mixture. The homogeneous solution was stirred overnight at room temperature.

An aliquot was then taken and blown to dryness, then added MeOH and ran an LC/MS using 10:1:0.5 EtOAc: MeOH:NH$_4$OH as eluent system, Rf=0.5 as a new spot.

LC/MS showed one major peak (>95%) at rt 3.22 minutes, with a M+H=629.3, consistent with desired product.

Example 22

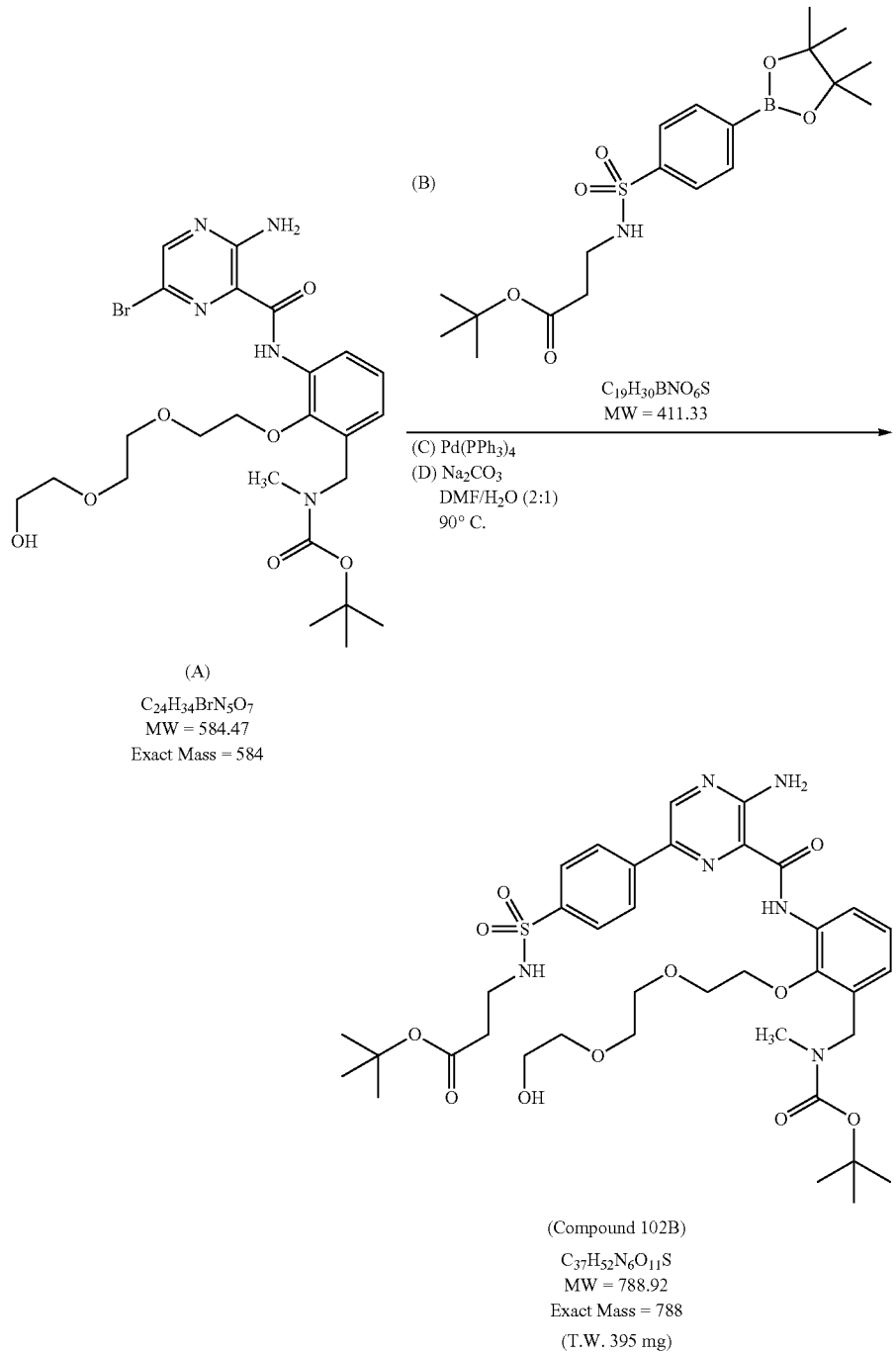

(A): Compound 173A; MW 584.47; 0.50 mmol=292 mg
(B): Compound 35B; MW=411.33; 1.5 equivalent=0.75 mmol=308 mg
(C): Pd(PPh$_3$)$_4$; Strem; MW=1155.57; 0.1 equivalents=0.050 mmol=58 mg
(D): 2M Na$_2$CO$_3$; 5 mL
DMF; Acros; 10 mL Some or all of this example was performed using the procedure of *J. Med. Chem.* 2011, 54, 2320-2330

In a small pressure reaction vessel, (A) and (B) were mixed with DMF, (D) was added, the solution was capped, warmed to 85° C., and heated overnight.

The sample was then removed from the heat. After cooling, an aliquot was partitioned between EtOAc and water and the organic phase was then evaluated by TLC, 100% EtOAc as eluent. No SM A remained at Rf=0.5 (confirmed by co-spot), and major spot now at Rf=0.4.

The heterogeneous reaction mixture was partitioned between EtOAc (75 mL) and water (60 mL). The aqueous phase was washed with a second portion of EtOAc (50 mL) and then the combined organic phases were washed sequentially with water (50 mL) and brine (50 mL). The organic phase was dried over $Na_2SO_4$, filtered and concentrated to give 520 mg (T.W. 395 mg) of a brown oil of Compound 102A. TLC: 100% EtOAc Rf=0.45 as major spot. The sample was dissolved into $CH_2Cl_2$ and loaded onto a 12 g column. A gradient system was run on Isco eluting with 30-100% EtOAc/Hexane system over 16 minutes, where 30% was held for 2 minute, then ramped to 100% by 11 minutes. Relevant fractions were concentrated under reduced pressure and then under high vacuum to yield 270 mg (68%) of a yellow oil of Compound 102B. As true for other related intermediates, unfortunately not a solid. TLC (dissolved in EtOAc): 100% EtOAc Rf=0.65, homogeneous.

LC/MS (dissolved in MeOH): rt 4.54 minutes (~95%) (M+H=789.4, consistent with desired product and a stronger M+23=811.4) and rt 3.55 minutes (~5%) ($Ph_3P=O$). Compound 102B was used for subsequent step without further manipulation.

(C): Triphenylphosphine; Alfa Aesar; MW=262.29; 4 equivalents=1.16 mmol=304 mg (D): THF; DriSolv; 5 mL In a reaction vessel, (A) and (C) were dissolved in (D), and at 0° C. the resulting solution was treated with (B) neat dropwise over 30 seconds. The reaction mixture was concentrated under reduced pressure. The residue was dissolved in MeOH (5 mL), the resulting, stirring solution was diluted with water (12 equivalents=3.48 mmol=62 µL), followed by AcOH (MW 60.05, d=1.049; 5 equivalents=1.45 mmol=87 mg=83 µL) at room temperature. The mixture was cooled for 2 hours, filtered, rinsed with ice cold MeOH, and air dried over the weekend to provide 131 mg (58%) of yellow solid of Compound 104A. Analysis of Compound 104A: TLC: 1:1 EtOAc:hexane Rf=0.35, homogeneous; 100% EtOAc Rf=0.85, homogenous. LC/MS (dissolved in $CH_3CN$): rt 5.32 minutes (>98%) (M+23=793.4, consistent with desired product). $^1H$ NMR ($CDCl_3$): Ran before on Compound 41A. Compound 104A was used for subsequent step without further manipulation.

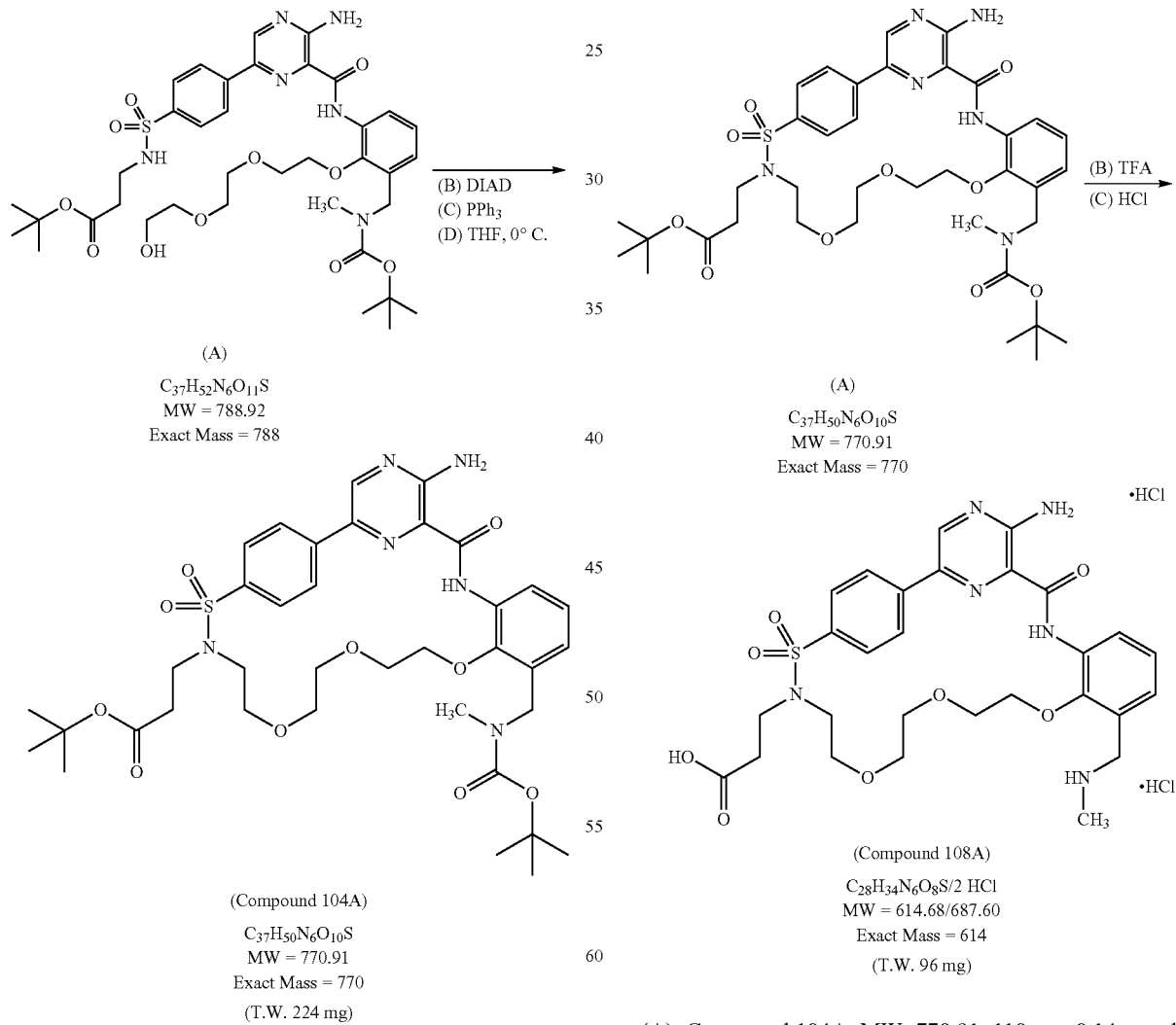

(A)
$C_{37}H_{52}N_6O_{11}S$
MW = 788.92
Exact Mass = 788

(A)
$C_{37}H_{50}N_6O_{10}S$
MW = 770.91
Exact Mass = 770

(Compound 104A)
$C_{37}H_{50}N_6O_{10}S$
MW = 770.91
Exact Mass = 770
(T.W. 224 mg)

(Compound 108A)
$C_{28}H_{34}N_6O_8S/2$ HCl
MW = 614.68/687.60
Exact Mass = 614
(T.W. 96 mg)

(A): Compound 102B; MW=788.92; 0.29 mmol=230 mg
(B): Diisopropyl azodicarboxylate; Acros; MW=202.21; d=1.027 g/mL 3 equivalent=0.87 mmol=176 mg=171 µL (A): Compound 104A; MW=770.91; 110 mg=0.14 mmol
(B): TFA; Acros; 3 mL
(C): 3N HCl In a small vial, (A) was dissolved in 0° C. (B) to give a yellow solution over about 5 minutes. The reaction was removed from the cooling bath and warmed to room temperature. After about 1 hour, the reaction mixture was blown to dryness and some 3N HCl, CH$_3$CN and water were added to provide a homogeneous solution. The solution was lyophilized overnight to provide a yellow lyophylate of Compound 108A which was used directly for subsequent reaction without further manipulation. A LC/MS on Compound 108A showed rt 2.70 minutes (M+H=615.2, consistent with desired product).

Example 23

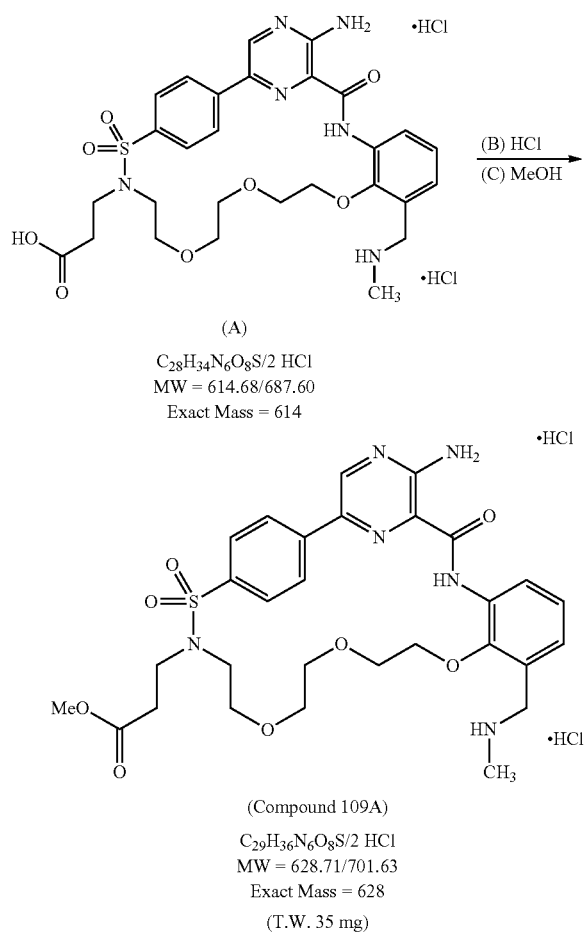

(A): Compound 108A (ATRN-151A); MW=687.60; 0.050 mmol=34 mg (B): Aldrich; 4 N HCl in Dioxane 2 mL (8 mmol HCl~160 equivalents)

(C): MeOH; Aldrich; 12 mL (A) was combined with (C), and then (B) was added at room temperature to the almost homogenous mixture which was stirred overnight at room temperature. The next afternoon, the reaction solution was concentrated under reduced pressure. The residue was treated with EtOAc to yield a yellow solid. This material was filtered and rinsed liberally with EtOAc. After air drying for 1 h left with 25 mg (71%) of yellow solid of Compound 109A. LC/MS showed one major peak (>95%) at rt 3.22 minutes (M+H=629.3, consistent with desired product. TLC versus SM A: 10:1:0.5 EtOAc:MeOH:NH$_4$OH as eluent system, Rf=0.6 as major spot, with trace spot at origin. $^1$H NMR (DMSO-d$_6$): consistent with desired product. Proceeded and tested this ester, labeling as ATRN-159-A.

Example 24: Preparation of Intermediate 1

Methyl (tert-butoxycarbonyl)-L-lysinate, (0.877 g, 3.37 mmol) was dissolved in 20 ml dichloromethane, followed by addition of ((benzyloxy)carbonyl)glycine (0.850 g, 4.00 mmol), hydroxybenzotriazole (HOBt) (0.320 g, 2.36 mmol), and 1-ethyl-3-(3-dimethylaminopropyl)carbodiimide (EDCI) (0.970 g, 5.05 mmol). The mixture was stirred overnight at room temperature. Water (10 mL) was added and the dichloromethane layer was separated and the aqueous layer was extracted again with dichloromethane (DCM) (10 mL). The combined dichloromethane layers were washed with aqueous NaHCO$_3$ (15 mL), water (15 mL), brine (15 mL), dried over Na$_2$SO$_4$ and concentrated to give intermediate 1, methyl N-6-(((benzyloxy)carbonyl)glycyl)-N2-(tert-butoxycarbonyl)-L-lysinate (1.400 g, 3.10 mmol, yield 92%). MS (ESI) m/z: 452 (M+H)$^+$.

Example 25: Preparation of Intermediate 2

Methyl N-6-(((benzyloxy)carbonyl)glycyl)-N2-(tert-butoxycarbonyl)-L-lysinate (1.400 g, 3.10 mmol) was dissolved in MeOH (20 mL), followed by addition of 10% wet Pd/C (0.2 g). The mixture was stirred under H$_2$ atmosphere (40 psi) overnight at room temperature. Pd/C was filtered off and the filtrate was concentrated to give intermediate 2, methyl N-2-(tert-butoxycarbonyl)-N-6-glycyl-L-lysinate (0.855 g, 2.79 mmol, yield 90%). MS (ESI) m/z: 318 (M+H)$^+$, $^1$H NMR (400 MHz, METHANOL-d$_4$) δ 4.10 (br dd, J=5.17, 8.69 Hz, 1H), 3.88-4.01 (m, 1H), 3.84 (br d, J=9.90 Hz, 1H), 3.73 (s, 3H), 3.13-3.31 (m, 2H), 1.73-1.89 (m, 1H), 1.61-1.72 (m, 1H), 1.50-1.60 (m, 2H), 1.48 (s, 2H), 1.46 (s, 9H).

Example 26: Preparation of Intermediate 4

Tert-butyl ((25-amino-16,16-dioxido-3-oxo-6,9,12-trioxa-16-thia-4,15-diaza-2(2,6)-pyrazina-1(1,4),5(1,2)-dibenzenacyclohexadecaphane-53-yl)methyl)(methyl)carbamate (See, e.g., WO2016/061097) (50 mg, 0.078 mmol) was dissolved in acetone (5 mL), followed by addition of K$_2$CO3 (21.5 mg, 0.156 mmol) and methyl 2-bromoacetate (35.7 mg, 0.234 mmol). The mixture was stirred at room temperature for 6 hours. Acetone was removed in vacuo. The residue was dissolved in dichloromethane (10 mL) and water (10 mL). The dichloromethane layer was separated and concentrated. The residue was dissolved in methanol (2 mL) and 1N NaOH (1 mL), which was stirred at room temperature overnight. 1 M HCl (~1 mL) was added and the layers were separated. The organic phase was concentrated and purified by reverse phase HPLC (Teledyne Isco, Lincoln Nebr.) (C$_{18}$ column) with acetonitrile/water as eluting solvent to yield intermediate 4, 2-(25-amino-53-(((tert-butoxycarbonyl)(methyl)amino)methyl)-16,16-dioxido-3-oxo-6,9,12-trioxa-16-thia-4,15-diaza-2(2,6)-pyrazina-1(1,4),5(1,2)-dibenzenacyclohexadecaphane-15-yl)acetic acid (29 mg, yield 53%). MS (ESI) m/z: 701 (M+H)⁺.

Example 27: Preparation of Intermediate 5

2-(25-amino-53-(((tert-butoxycarbonyl)(methyl)amino)methyl)-16,16-dioxido-3-oxo-6,9,12-trioxa-16-thia-4,15-diaza-2(2,6)-pyrazina-1(1,4),5(1,2)-dibenzenacyclohexadecaphane-15-yl)acetic acid (25 mg, 0.0357 mmol) was dissolved in 2 ml dicloromethane, followed by addition of methyl N2-(tert-butoxycarbonyl)-N6-glycyl-L-lysinate (22.6 mg, 0.0714 mmol), HOBt (9.7 mg, 0.0714 mmol), and EDCI (13.6 mg, 0.0714 mmol). The mixture was stirred overnight at room temperature. Water (5 mL) was added and the dichloromethane layer was separated, aqueous layer was extracted again with dichloromethane (5 mL). The combined dichloromethane layers were washed with aqueous NaHCO₃ (5 mL), water (5 mL), brine (5 mL), and dried over Na₂SO₄ and concentrated to give intermediate 5, methyl N6-((2-(25-amino-53-(((tert-butoxycarbonyl)(methyl)amino)methyl)-16,16-dioxido-3-oxo-6,9,12-trioxa-16-thia-4,15-diaza-2(2,6)-pyrazina-1(1,4),5(1,2)-dibenzenacyclohexadecaphane-15-yl)acetyl)glycyl)-N2-(tert-butoxycarbonyl)-D-lysinate (30 mg, yield 84%). MS (ESI) m/z: 1000 (M+H)⁺.

Example 28: Preparation of ATRN 6

Methyl N6-((2-(25-amino-53-(((tert-butoxycarbonyl)(methyl)amino)methyl)-16,16-dioxido-3-oxo-6,9,12-trioxa-16-thia-4,15-diaza-2(2,6)-pyrazina-1(1,4),5(1,2)-dibenzenacyclohexadecaphane-15-yl)acetyl)glycyl)-N2-(tert-butoxycarbonyl)-D-lysinate (25 mg, 0.025 mmol) was dissolved in 2 ml dichloromethan, followed by addition of trifluoroacetic acid (0.5 mL). The mixture was stirred overnight at room temperature. Solvents were removed. The residue was dissolved in dichloromethane (5 mL) and 1 N aq. NaHCO₃ (5 mL). The dichloromethane layer was separated and concentrated. The residue was purified by reverse phase HPLC (C₁₈ column) with acetonitrile/water as eluting solvent. To the clean fractions, 1 mL 1 N HCl was added. Upon concentration, yielded ATRN 6, methyl N6-((2-(25-amino-53-((methylamino)methyl)-16,16-dioxido-3-oxo-6,9,12-trioxa-16-thia-4,15-diaza-2(2,6)-pyrazina-1(1,4),5(1,2)-dibenzenacyclohexadecaphane-15-yl)acetyl)glycyl)-D-lysinate dihydrochloride (16 mg, yield 80%). MS (ESI) m/z: 800 (M+H)⁺, ¹H NMR (400 MHz, METHANOL-d₄) δ 10.62 (s, 1H), 8.89 (s, 1H), 8.67 (dd, J=1.43, 8.25 Hz, 1H), 8.16-8.29 (m, 2H), 8.10 (d, J=8.80 Hz, 2H), 7.30-7.38 (m, 1H), 7.19-7.28 (m, 1H), 4.35 (s, 2H), 4.17 (br d, J=4.62 Hz, 2H), 4.10 (s, 2H), 4.06 (t, J=6.38 Hz, 1H), 3.92-4.00 (m, 2H), 3.89 (s, 2H), 3.86 (s, 3H), 3.77 (s, 2H), 3.53-3.69 (m, 6H), 3.28 (br d, J=2.64 Hz, 2H), 2.79 (s, 3H), 1.81-2.14 (m, 2H), 1.34-1.73 (m, 4H).

Example 29: Preparation of Intermediate 9

Intermediate 9 was prepared according to Example 26, using tert-butyl ((25-amino-16,16-dioxido-3-oxo-6,9,12-trioxa-16-thia-4,15-diaza-2(2,6)-pyrazina-1(1,4),5(1,2)-dibenzenacyclohexadecaphane-53-yl)methyl)(methyl)carbamate (50 mg, 0.078 mmol) and methyl 4-bromobutanoate to yield intermediate 9, methyl 4-(25-amino-53-(((tert-butoxy carbonyl)(methyl)amino)methyl)-16,16-dioxido-3-oxo-6,9,12-trioxa-16-thia-4,15-diaza-2(2,6)-pyrazina-1(1,4),5(1,2)-dibenzenacyclohexadecaphane-15-yl)butanoate (27 mg, yield 47.5%). MS (ESI) m/z: 729 (M+H)⁺.

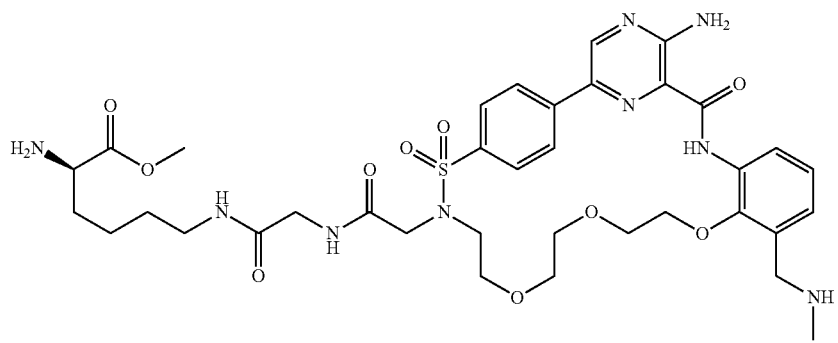

ATRN 6

Example 30: Preparation of Intermediate 10

Intermediate 10 was prepared according to Example 27 using intermediate 9 (25 mg, 0.034 mmol) to yield methyl N6-((4-(25-amino-53-(((tert-butoxy carbonyl)(methyl)amino)methyl)-16,16-dioxido-3-oxo-6,9,12-trioxa-16-thia-4,15-diaza-2(2,6)-pyrazina-1(1,4),5(1,2)-dibenzenacyclohexadecaphane-15-yl)butanoyl)glycyl)-N2-(tert-butoxycarbonyl)-D-lysinate (23 mg, yield 65.7%). MS (ESI) m/z: 1028 (M+H)$^+$.

Example 31: Preparation of ATRN 7

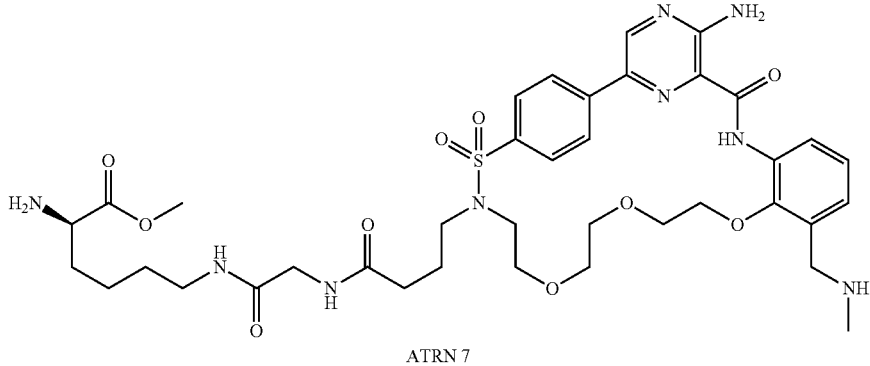 [SMILES: CNCc1cccc2c1OCCOCCOCCN(CCCC(=O)NCC(=O)NCCCC[C@@H](N)C(=O)OC)S(=O)(=O)c1ccc(cc1)-c1cnc(N)c(n1)C(=O)N2]

ATRN 7

ATRN 7 was prepared according to Example 28 using intermediate 10 (23 mg, 0.022 mmol) to produce methyl N6-((4-(25-amino-53-((methylamino)methyl)-16,16-dioxido-3-oxo-6,9,12-trioxa-16-thia-4,15-diaza-2(2,6)-pyrazina-1(1,4),5(1,2)-dibenzenacyclohexadecaphane-15-yl)butanoyl)glycyl)-D-lysinate dihydrochloride (17.6 mg, yield 89%). MS (ESI) m/z: 828 (M+H)$^+$, $^1$H NMR (400 MHz, METHANOL-$d_4$) δ 10.62 (s, 1H), 8.88 (s, 1H), 8.65 (dd, J=1.43, 8.25 Hz, 1H), 8.18 (d, J=8.58 Hz, 2H), 8.04 (d, J=8.58 Hz, 2H), 7.29-7.41 (m, 1H), 7.18-7.28 (m, 1H), 4.35 (s, 2H), 4.12-4.23 (m, 2H), 4.04 (t, J=6.38 Hz, 1H), 3.90-4.00 (m, 1H), 3.88-3.98 (m, 1H), 3.85 (s, 3H), 3.83 (s, 2H), 3.62-3.69 (m, 4H), 3.55-3.61 (m, 4H), 3.42 (t, J=6.82 Hz, 2H), 3.24 (t, J=6.71 Hz, 2H), 2.79 (s, 3H), 2.41 (s, 2H), 1.78-2.06 (m, 4H), 1.31-1.67 (m, 4H).

Example 32: 19S Proteasome Cleavage

200 μM isopeptide-containing compound will be incubated with 1 μg human 19S proteasome (Boston Biochem, E-366) in 200 μM Hepes pH 7.5, 200 μM NaCl, 10 μM dithiolthreitol and 0.2% glycerol in a 50 μl reaction volume at 37° C. for 5, 10, 20 and 40 minutes. Samples will be snap frozen in on dry ice. The samples will be thawed, and trifluoroacidic acid (TFA) will be added. The samples will be analyzed by LC-MS to establish cleavage of the isopeptide moiety to provide ATRN 6-A and/or ATRN 6-B or ATRN 7-A and/or ATRN 7-B.

Example 33: USP2 Cleavage

200 μM isopeptide-containing compound will be incubated with 500 nM USP2 (Recombinant Human USP2 Catalytic Domain, Bostong Biochem, E-504) in 500 μM HEPES pH 8.0, 2 mM NaCl, 5 μM ethylenediaminetetraacetic acid, and 10 μM dithiolthreitol in a 50 μl reaction volume at 37° C. for 5, 10, 20 and 40 minutes. Samples will be snap frozen on dry ice. The samples will be thawed, and trifluoroacidic acid (TFA) will be added. The samples will be analyzed by LC-MS to establish cleavage of the isopeptide moiety to provide ATRN 6-A and/or ATRN 6-B or ATRN 7-A and/or ATRN 7-B.

Example 34

A. Atrize Assessment of ATRN Compounds

Jurkat Bcl/xl cells were seeded at 1×10$^5$ cells/well in a 96-well plate. Compounds were then added at a final concentration of 5, 2.5, 1.25, 0.625, 0.313, 0.156, 0.078 and 0 μM, in both the presence and absence of 0.2 μM aphidicolin. Cells were incubated for 24 hours at 37° C., 5% CO$_2$ and then centrifuged at 300×g for 5 minutes at 4° C. Cells were then washed with PBS, centrifuged again and fixed with 500 μl of cold 70% ethanol at −20° C. for 2 hours. After fixation cells were centrifuged once more, ethanol discarded and cells resuspended in 70 μl PI staining buffer (0.1% TritonX-100, 5 mM EDTA, 40 μg/ml propidium idiodide, 0.05 mg/ml RNaseA in PBS) diluted in 130 μl 2% FBS in PBS. Cell cycle profiles were collected using the Guava EasyCyte Plus and analyzed using InCyte™.

B. Cellular Kinase Assay

Cellular kinase assays were performed in HCT116 Bcl/xl cells. Cells were seeded at 1×10$^6$ cells/well in 6-well plates and incubated overnight at 37° C. 5% CO$_2$. The following day cells were treated with compounds at 10, 3, 1, 0.3 μM for 30 minutes, aphidicolin was then added to a final concentration of 5 μM and cells were incubated for a further 4 hours. After 4 hours cells were washed with PBS, harvested in 1× laemmli buffer, and boiled for 5 minutes to lyse cells. Whole-cell lysates were separated by SDS polyacrylamide gel electrophoresis on 12% gels and transferred onto 0.45 μM polyvinylidene difluoride membranes. Blots were probed for GAPDH (US Biologicals #30981) and phospho-S345 Chk1 (Cell Signaling #2348) according to manufacturers' instructions.

C. ATR In Vitro Kinase Assays.

Kinase assays were conducted using the KinaseProfiler service of Eurofins Pharma Discovery Services UK Limited, according to the protocols detailed at http://www.eurofins.com/pharmadiscovery. Briefly, ATR/ATRIP (h) was incubated with test compound at 10, 3, 1, 0.3, 0.1, 0.03, 0.01, 0.003 and 0.001 μM in assay buffer containing 50 nM GST-cMyc-p53 and Mg/ATP (concentration as required). The reaction was initiated by the addition of the Mg/ATP mix. After incubation for 30 minutes at room temperature, the reaction was stopped by the addition of stop solution containing EDTA. Finally, detection buffer was added, which contains d2-labelled anti-GST monoclonal antibody, and a Europium-labeled anti-phospho Ser15 antibody against phosphorylated p53. The plate was then read in time-resolved fluorescence mode and the homogeneous time-resolved fluorescence (HTRF) signal was determined according to the formula HTRF=10000×(Em665 nm/Em620 nm).

Aspects of the Disclosure

Aspect 1. A compound of Formula (III) or Formula (IV):

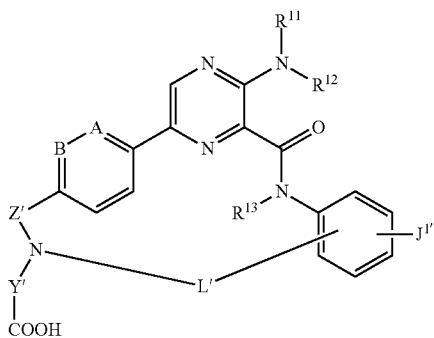
(III)

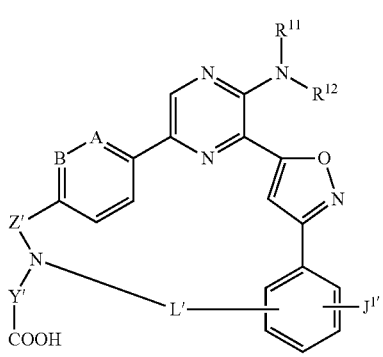
(IV)

wherein
A is CH or N;
B is CH or N;
$R^{11}$ is H or $C_{1-6}$alkyl;
$R^{12}$ is H or $C_{1-6}$alkyl;
$R^{13}$ is H or $C_{1-6}$alkyl;
Z' is —$SO_2$— or —C(O)—;
Y' is an alkylene;
J$^{1'}$ is H, optionally substituted —$C_{1-6}$alkyl,
—$C_{1-6}$alk-NH-(optionally substituted $C_{1-6}$alkyl), or
—$C_{1-6}$alk-NH—$C_{0-6}$alk-(optionally substituted $C_{3-6}$heterocycloalkyl); and
L' is a 7 to 17-membered linking group comprising an alkylene interrupted by 1, 2, 3, 4 or 5 heteroatom moieties selected from —O—, —NH—, —N($C_{1-6}$alkyl), —N(optionally substituted $C_{1-6}$alkyl), and —N($C_{1-6}$alkyl)-O(optionally substituted $C_{1-6}$alkyl);
or a pharmaceutically acceptable salt thereof.

Aspect 2. The compound of Aspect 1, wherein A is CH and B is CH.

Aspect 3. The compound of Aspect 1, wherein A is N and B is CH.

Aspect 4. The compound of Aspect 1, wherein A is CH and B is N.

Aspect 5. The compound of any one of the preceding Aspects, wherein $R^{11}$, $R^{12}$, and $R^{13}$ are each H.

Aspect 6. The compound of any one of the preceding Aspects, wherein Z' is —$SO_2$—.

Aspect 7. The compound of any one of Aspects 1 to 5, wherein Z' is —C(O)—.

Aspect 8. The compound of any one of the preceding Aspects, wherein Y' is a $C_{1-6}$alkylene.

Aspect 9. The compound of Aspect 8, wherein Y' is $C_1$alkylene.

Aspect 10. The compound of Aspect 8, wherein Y' is $C_3$alkylene.

Aspect 11. The compound of any one of the preceding Aspects, wherein J$^{1'}$ is H.

Aspect 12. The compound of any one of Aspects 1 to 10, wherein J$^{1'}$ is —$C_{1-6}$alkyl or substituted —$C_{1-6}$alkyl.

Aspect 13. The compound of any one of Aspects 1 to 10, wherein J$^{1'}$ is —$C_{1-6}$alk-NH—($C_{1-6}$alkyl) or —$C_{1-6}$alk-NH-(substituted $C_{1-6}$alkyl).

Aspect 14. The compound of any one of Aspects 1 to 10, wherein J$^{1'}$ is —$C_{1-6}$alk-NH—$C_{0-6}$alk-($C_{3-6}$heterocycloalkyl) or —$C_{1-6}$alk-NH—$C_{0-6}$alk-(substituted $C_{3-6}$heterocycloalkyl).

Aspect 15. The compound of any one of the preceding Aspects, wherein L' is a 7 or 9-membered linking group comprising an alkylene interrupted by three —O— heteroatom moieties.

Aspect 16. The compound of any one of Aspects 1 to 14, wherein L' is a 7 or 9-membered linking group comprising an alkylene interrupted by one —O— heteroatom moiety and one —NH—, —N($C_{1-6}$alkyl), —N(optionally substituted $C_{1-6}$alkyl), or —N($C_{1-6}$alkyl)-O(optionally substituted $C_{1-6}$alkyl) heteroatom moiety.

Aspect 17. The compound of any one of Aspects 1 to 14, wherein L' is a 7 or 9-membered linking group comprising an alkylene interrupted by two —O— heteroatom moieties and one —NH—, —N($C_{1-6}$alkyl), —N(optionally substituted $C_{1-6}$alkyl), or —N($C_{1-6}$alkyl)-O(optionally substituted $C_{1-6}$alkyl) heteroatom moiety.

Aspect 18. The compound of any one of the preceding Aspects, wherein L' is —($CH_2CH_2O)_3$—, —$CH_2$($CH_2CH_2O)_2$—, —CH($CH_3$)($CH_2CH_2O)_3$—, —($CH_2CH_2CH_2O)_2$—, —$CH_2CH_2NH(CH_2CH_2O)_2$—, or —O—($CH_2CH_2O)_2$—.

Aspect 19. The compound of Aspect 1 that is

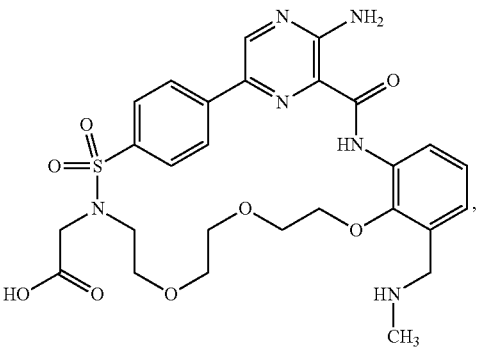

109 -continued
110 -continued
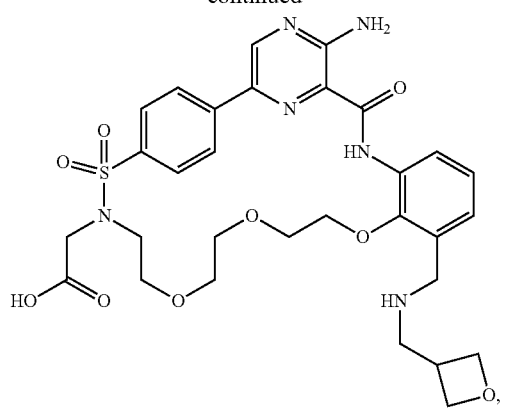
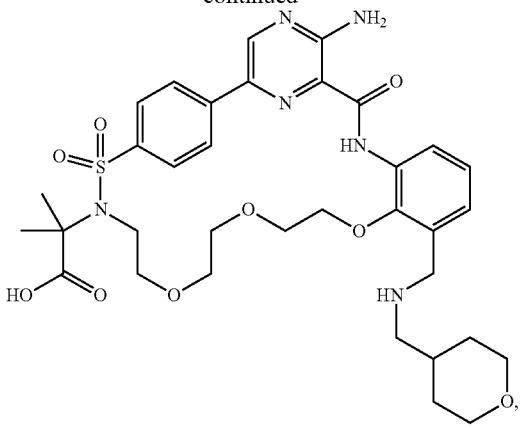

or a pharmaceutically acceptable salt thereof.

Aspect 20. A pharmaceutical composition comprising a compound according to any one of the preceding Aspects and a pharmaceutically acceptable carrier.

Aspect 21. A method of treating cancer in a patient comprising administering to the patient a compound according to any one of Aspects 1 to 19.

Aspect 22. The method of Aspects 21, wherein the compound is administered in combination with another therapeutic chemotherapy agent.

Aspect 23. The method of Aspect 2 or 22, wherein the cancer is breast cancer, prostate cancer, pancreatic cancer, lung cancer, colorectal cancer, ovarian cancer, liver cancer, melanoma, renal cancer, a central nervous system cancer, brain cancer, glioblastoma, a leukemia, or a lymphoma.

Aspect 24. The method of Aspect 21, wherein the cancer is ocular melanoma, desmoplastic round cell tumor, chondrosarcoma, leptomengial disease, diffuse large B-cell lymphoma, acute lymphoblastic leukemia, acute myeloid leukemia, adrenocortical carcinoma, an AIDS-related cancer, an AIDS-related lymphoma, anal or rectal cancer, appendix cancer, astrocytomas, atypical teratoid/rhabdoid tumor, basal cell carcinoma, bile duct cancer, bladder cancer, bone cancer, osteosarcoma or malignant fibrous histiocytoma, brain tumor, breast cancer, prostate cancer, bronchial tumor, Burkitt lymphoma, spinal cord tumor, carcinoid tumor, carcinoma of unknown primary, central nervous system atypical teratoid/rhabdoid tumor, leptomeningeal disease, central nervous system embryonal tumors, central nervous system lymphoma, cervical cancer, chordoma, chronic lymphocytic leukemia, chronic myelogenous leukemia, chronic myeloproliferative, disorders, colon cancer, colorectal cancer, craniopharyngioma, cutaneous T-Cell lymphoma, endometrial cancer, ependymoblastoma, ependymoma, esophageal cancer, a Ewing sarcoma family tumor, extracranial germ cell tumor, extragonadal germ cell tumor, extrahepatic bile duct cancer, eye cancer, gallbladder cancer, gastric (stomach) cancer, gastrointestinal carcinoid tumor, gastrointestinal stromal Tumor (GIST), germ cell tumor, gestational trophoblastic tumor, glioma, hairy cell leukemia, head or neck cancer, hepatocellular (liver) cancer, histiocytosis, Hodgkin's lymphoma, hypopharyngeal cancer, Kaposi sarcoma, kidney (renal cell) cancer, Langerhan's cell histiocytosis, laryngeal cancer, lip or oral cavity cancer, liver cancer, lung cancer, Non-Hodgkin's lymphoma, primary central nervous system lymphoma, Waldenström's macroglobulinemia (lymphoplasmacytic lymphoma), malignant fibrous histiocytoma of bone or osteosarcoma, medulloblastoma, medulloepithelioma, melanoma, merkel cell carcinoma, mesothelioma, metastatic squamous neck cancer with occult primary, multiple endocrine neoplasia syndrome, mouth cancer, multiple myeloma/plasma cell neoplasm, mycosis fungoides, myelodysplastic syndromes, myelodysplastic/myeloproliferative neoplasms, multiple myeloma, myeloproliferative disorder, nasal cavity or paranasal sinus cancer, nasopharyngeal cancer, neuroblastoma, oral cancer, oropharyngeal cancer, osteosarcoma or malignant fibrous histiocytoma of bone, ovarian cancer, ovarian germ cell tumor, ovarian epithelial cancer, ovarian low malignant potential tumor, pancreatic cancer, papillomatosis, paranasal sinus or nasal cavity cancer, parathyroid cancer, penile cancer, pharyngeal cancer, pineal parenchymal tumors of intermediate differentiation, pineoblastoma or supratentorial primitive neuroectodermal tumors, pituitary tumor, pleuropulmonary blastoma, pregnancy or breast cancer, prostate cancer, rectal cancer, renal pelvis or ureter cancer, respiratory tract carcinoma involving the NUT gene on chromosome 15, retinoblastoma, rhabdomyosarcoma, high grade prostate cancer, medium grade prostate cancer, low grade prostate cancer, castration-resistant prostate cancer, salivary gland cancer, sarcoma, Sézary syndrome, skin cancer, ocular cancer, skin carcinoma, small intestine cancer, soft tissue sarcoma, squamous cell carcinoma, squamous neck cancer with occult primary, supratentorial primitive neuroectodermal tumors, T-Cell lymphoma, testicular cancer, throat cancer, thymoma or thymic carcinoma, thyroid cancer, transitional cell cancer of the renal pelvis or ureter, gestational trophoblastic tumor, cancer of unknown primary site such as carcinoma of unknown primary site, unusual cancers of childhood, urethral cancer, uterine sarcoma, vaginal cancer, vulvar cancer, Wilm's tumor, or a women's cancer.

What is claimed:
1. A compound of Formula (I) or Formula (II):

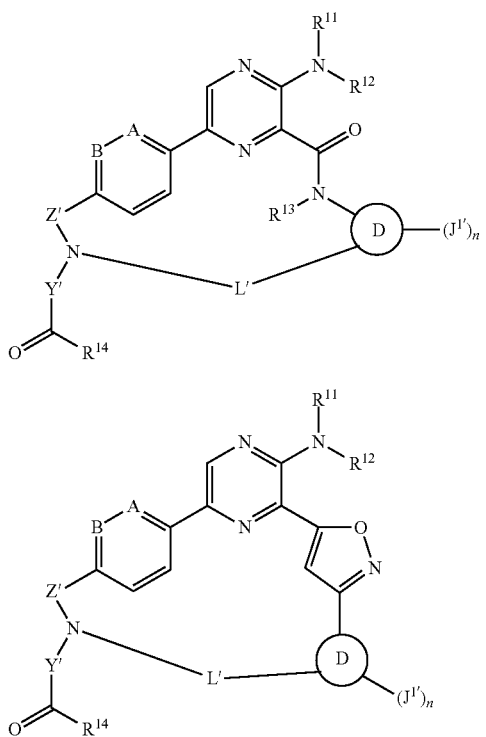

wherein:
A is CH, C—$C_{1-6}$alkyl, C—$C_{1-6}$haloalkyl, or N;
B is CH, C—$C_{1-6}$alkyl, C—$C_{1-6}$haloalkyl, or N;
ring D is phenylene or pyridylene;
$R^{11}$ is H or $C_{1-6}$alkyl;
$R^{12}$ is H or $C_{1-6}$alkyl;
$R^{13}$ is H or $C_{1-6}$alkyl;
$R^{14}$ is OH, —O$C_{1-30}$alkyl, —O-aryl, —O—$C_{1-30}$alk-C(O)$C_{1-30}$alkyl, —O—$C_{1-30}$alk-C(O)NR$^{15}$R$^{16}$, —O-monosaccharide, —S—$C_{1-30}$alkyl, a peptidyl moiety, an isopeptide moiety, or a peptidyl-isopeptide moiety;
$R^{15}$ and $R^{16}$ are, independently, optionally substituted $C_{1-30}$alkyl, $C_{1-20}$alkenyl, aryl, arylalkyl, or $C_{3-10}$cycloalkyl;
Z' is —SO$_2$— or —C(O)—;
Y' is an alkylene;
n is 1 or 2;
each J$^{1'}$ is, independently, H, halogen, optionally substituted —$C_{1-6}$alkyl, optionally substituted $C_{1-6}$haloalkyl, optionally substituted —$C_{1-6}$alkoxy, NH$_2$, NH-(optionally substituted $C_{1-6}$alkyl), N-(optionally substituted $C_{1-6}$alkyl)(optionally substituted $C_{1-6}$alkyl), —$C_{1-6}$alk-NH-(optionally substituted $C_{1-6}$alkyl), or —$C_{1-6}$alk-NH—$C_{0-6}$alk-(optionally substituted $C_{3-6}$heterocycloalkyl); and L' is a 7 to 17-membered linking group comprising an alkylene interrupted by 1, 2, 3, 4 or 5 heteroatom moieties selected from —O—, —NH—, —N($C_{1-6}$alkyl), —N(optionally substituted $C_{1-6}$alkyl), and —N($C_{1-6}$alkyl)-O(optionally substituted $C_{1-6}$alkyl);
or a pharmaceutically acceptable salt thereof.

2. The compound of claim 1, wherein $R^{14}$ is —OH, —S—$C_{1-30}$alkyl, —O$C_{1-30}$alkyl, —Oaryl, —O—$C_{1-30}$alk-C(O)$C_{1-30}$alkyl, —O—$C_{1-30}$alk-C(O)N($C_{1-30}$alkyl)($C_{1-30}$alkyl), or O-monosaccharide.

3. The compound of claim 1, wherein $R^{14}$ is a peptidyl moiety.

4. The compound of claim 3, wherein the peptidyl moiety contains 1 to 5 amino acid residues, wherein the amino acids are independently selected from naturally-occurring amino acids and non-naturally-occurring amino acids.

5. The compound of claim 1, wherein $R^{14}$ is an isopeptide moiety that is
—NH—$C_{1-10}$alk-CH(NH$_2$)($C_{1-10}$alkyl)OH,
—NH—$C_{1-10}$alk-CH(NH$C_{1-10}$alkyl)($C_{1-10}$alkyl)OH,
—NH—$C_{1-10}$alk-CH(N[$C_{1-10}$alkyl]$_2$)($C_{1-10}$alkyl)OH,
—NH—$C_{1-10}$alk-CH(NH$_2$)(CO—$C_{1-10}$alkyl),
—NH—$C_{1-10}$alk-CH(NH$C_{1-10}$alkyl)(CO—$C_{1-10}$alkyl),
—NH—$C_{1-10}$alk-CH(N[$C_{1-10}$alkyl]$_2$)(CO—$C_{1-10}$alkyl),
—NH—$C_{1-10}$alk-CH(NH$_2$)(COO—$C_{1-10}$alkyl),
—NH—$C_{1-10}$alk-CH(NH$C_{1-10}$alkyl)(COO—$C_{1-10}$alkyl), or
—NH—$C_{1-10}$alk-CH(N[$C_{1-10}$alkyl]$_2$)(COO—$C_{1-10}$ alkyl).

6. The compound of claim 1, wherein $R^{14}$ is a peptidyl-isopeptide moiety that is
-Q-NH—$C_{1-10}$alk-CH(NH$_2$)($C_{1-10}$alkyl)OH,
-Q-NH—$C_{1-10}$alk-CH(NH$C_{1-10}$alkyl)($C_{1-10}$alkyl)OH,
-Q-NH—$C_{1-10}$alk-CH(N[$C_{1-10}$alkyl]$_2$)($C_{1-10}$alkyl)OH,
-Q-NH—$C_{1-10}$alk-CH(NH$_2$)(CO—$C_{1-10}$alkyl),
-Q-NH—$C_{1-10}$alk-CH(N[$C_{1-10}$alkyl]$_2$)(CO—$C_{1-10}$alkyl),
-Q-NH—$C_{1-10}$alk-CH(NH$_2$)(COO—$C_{1-10}$alkyl),
-Q-NH—$C_{1-10}$alk-CH(NH$C_{1-10}$alkyl)(COO—$C_{1-10}$ alkyl), or
-Q-NH—$C_{1-10}$alk-CH(N[$C_{1-10}$alkyl]$_2$)(COO—$C_{1-10}$alkyl), wherein Q is a peptidyl moiety containing 1 to 5 amino acid residues, wherein the amino acid residues are independently selected from naturally-occurring amino acids and non-naturally-occurring amino acids.

7. The compound of claim 6, wherein the isopeptide moiety is

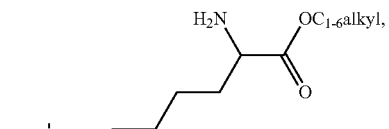

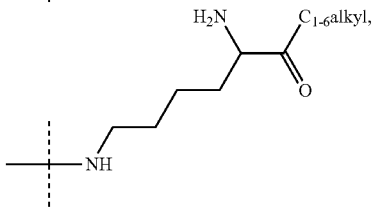

-continued

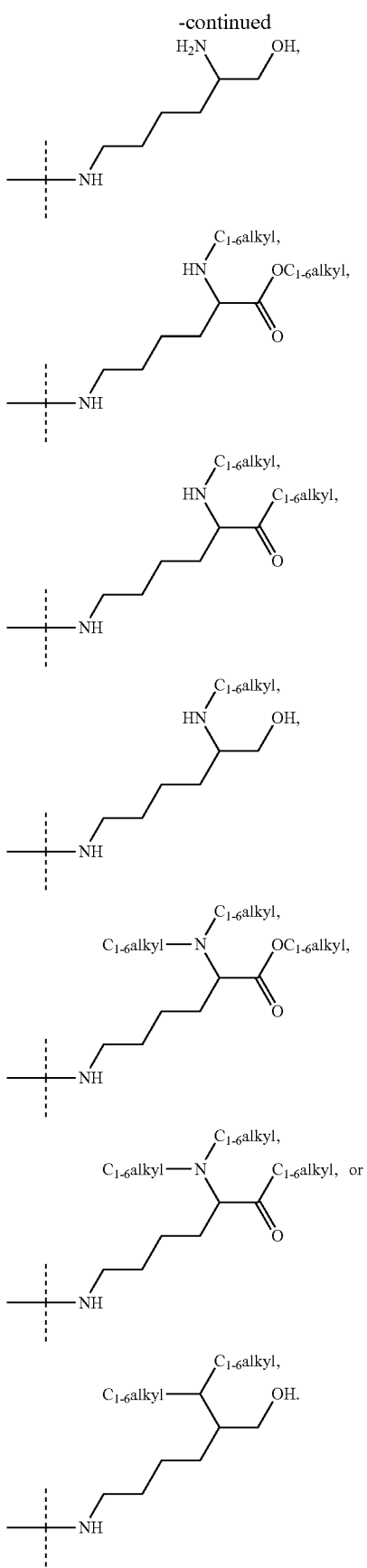

8. The compound of claim 1, wherein $R^{14}$ is —O-monosaccharide, —O-glucuronide, or —O—$C_{1-30}$alk-C(O)N($C_{1-30}$alkyl)($C_{1-30}$alkyl).

9. The compound of claim 1, wherein A is CH and B is CH.

10. The compound of claim 1, wherein A is N and B is CH.

11. The compound of claim 1, wherein A is CH and B is N.

12. The compound of claim 1, wherein one or both of A and B is C—$C_{1-6}$alkyl.

13. The compound of claim 1, wherein one or both of A and B is C—$C_{1-6}$fluoroalkyl.

14. The compound of claim 1, wherein $R^{11}$, $R^{12}$ and $R^{13}$ are each H.

15. The compound of claim 1, wherein Z' is —$SO_2$—.

16. The compound of claim 1, wherein Z' is —C(O)—.

17. The compound of claim 1, wherein Y' is a $C_{1-6}$alkylene.

18. The compound of claim 1, wherein ring D is phenylene.

19. The compound of claim 1, wherein ring D is pyridylene.

20. The compound of claim 1, wherein n is 1.

21. The compound of claim 1, wherein $J^{1'}$ is H or —$C_{1-6}$alkyl or substituted —$C_{1-6}$alkyl.

22. The compound of claim 1, wherein $J^{1'}$ is —$C_{1-6}$alk-NH—($C_{1-6}$alkyl) or —$C_{1-6}$alk-NH-(substituted $C_{1-6}$alkyl).

23. The compound of claim 1, wherein $J^{1'}$ is —$C_{1-6}$alk-NH—$C_{0-6}$alk-($C_{3-6}$heterocycloalkyl) or —$C_{1-6}$alk-NH—$C_{0-6}$alk-(substituted $C_{3-6}$heterocycloalkyl).

24. The compound of claim 1, wherein L' is a 7 or 9-membered linking group comprising an alkylene interrupted by three —O— heteroatom moieties.

25. The compound of claim 1, wherein L' is a 7 or 9-membered linking group comprising an alkylene interrupted by one —O— heteroatom moiety and one —NH—, —N($C_{1-6}$alkyl), —N(optionally substituted $C_{1-6}$alkyl), or —N($C_{1-6}$alkyl)-O(optionally substituted $C_{1-6}$alkyl) heteroatom moiety.

26. The compound of claim 1, wherein L' is a 7 or 9-membered linking group comprising an alkylene interrupted by two —O— heteroatom moieties and one —NH—, —N($C_{1-6}$alkyl), —N(optionally substituted $C_{1-6}$alkyl), or —N($C_{1-6}$alkyl)-O(optionally substituted $C_{1-6}$alkyl) heteroatom moiety.

27. The compound of claim 1, wherein L' is —($CH_2CH_2O)_3$—, —$CH_2(CH_2CH_2O)_2$—, —CH($CH_3$)($CH_2CH_2O)_3$—, —($CH_2CH_2O)_2$—, —$CH_2CH_2$NH($CH_2CH_2O)_2$, or —O-($CH_2CH_2O)_2$—.

28. The compound of claim 1 that is

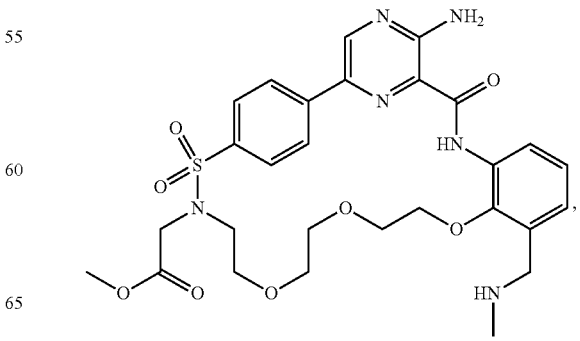

117
-continued
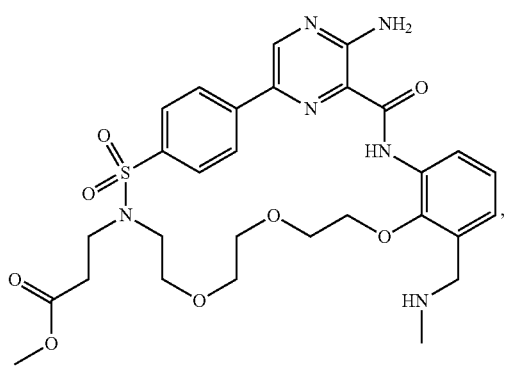
118
-continued
or a pharmaceutically acceptable salt thereof.
29. The compound of claim 1 that is
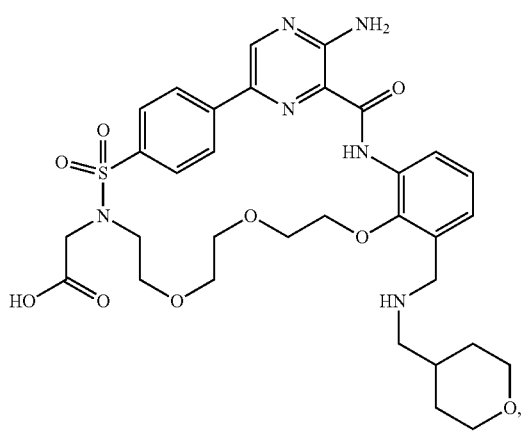

119
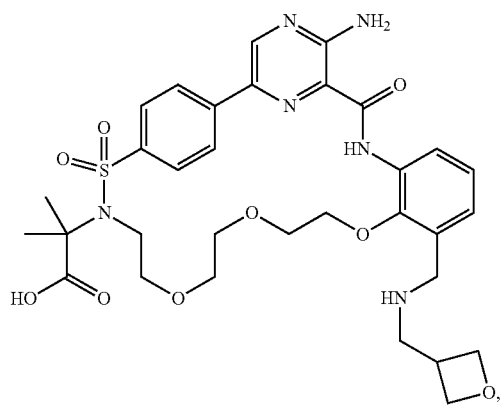
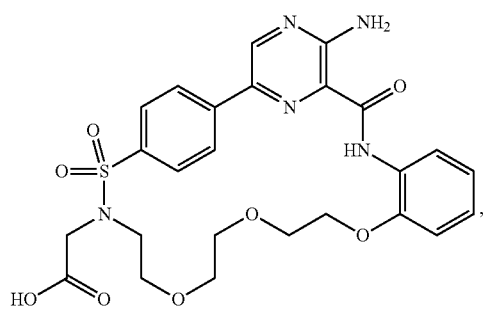
120
-continued
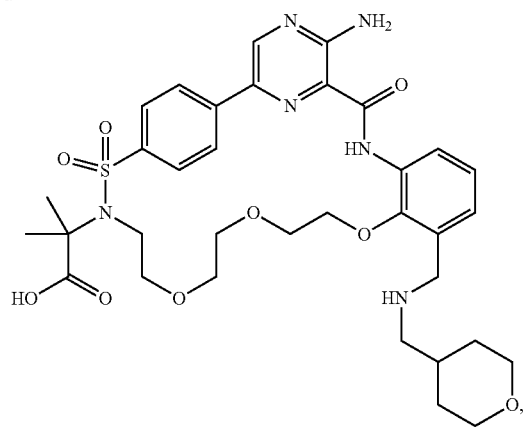
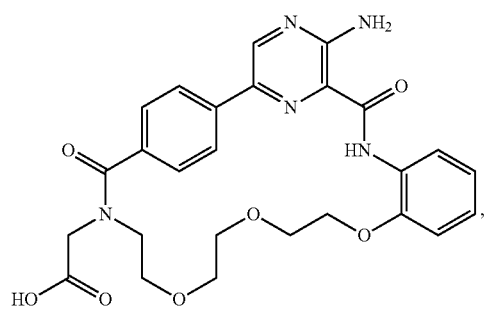
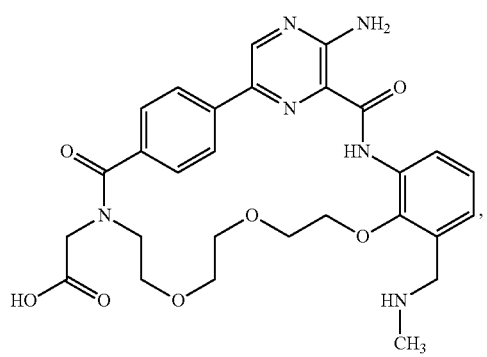
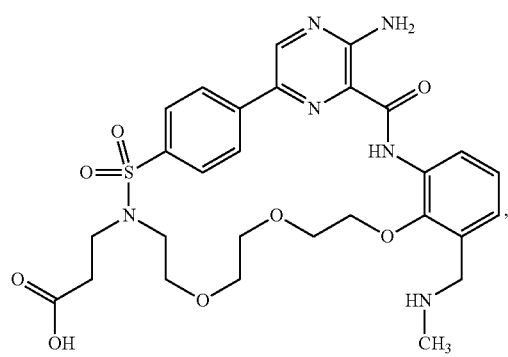
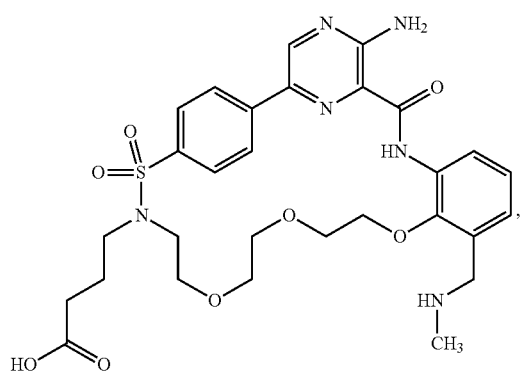
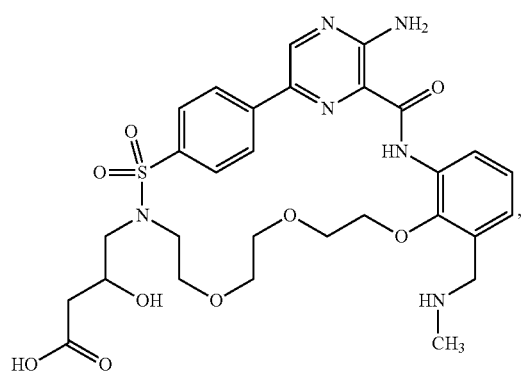

121
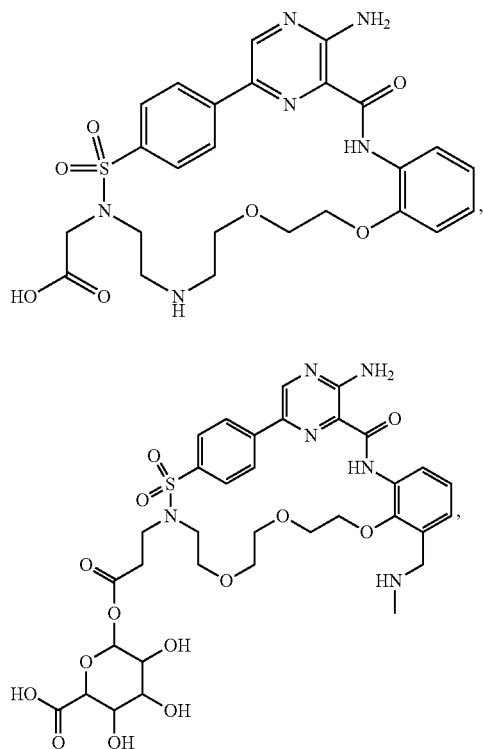
122
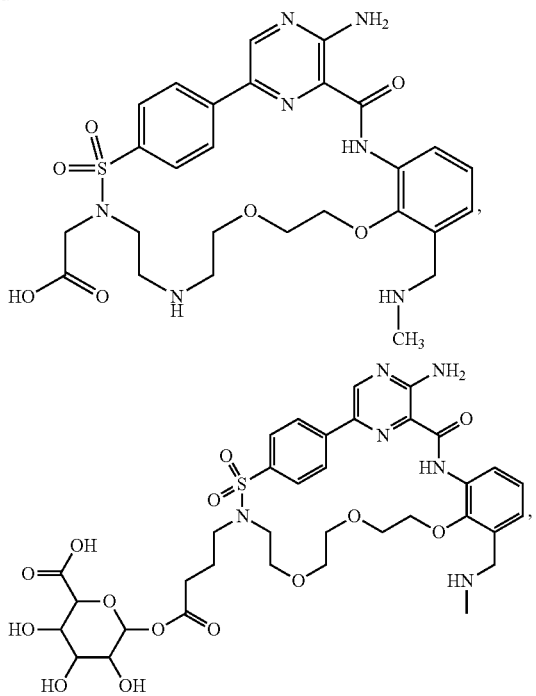
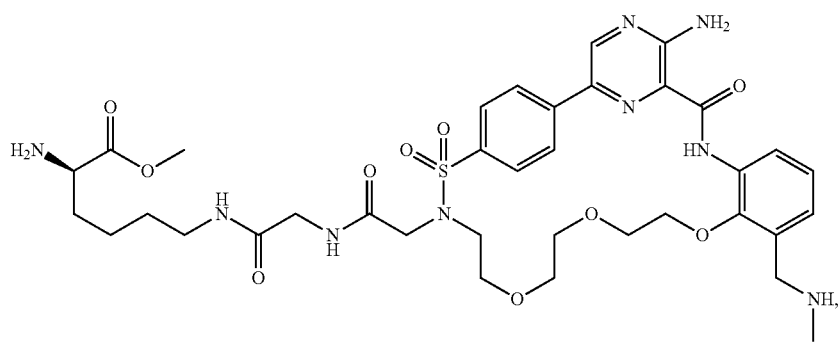
ATRN 6
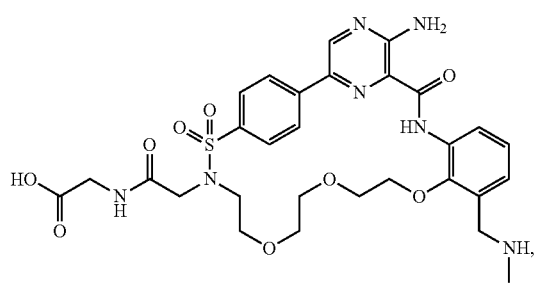
ATRN 6-A
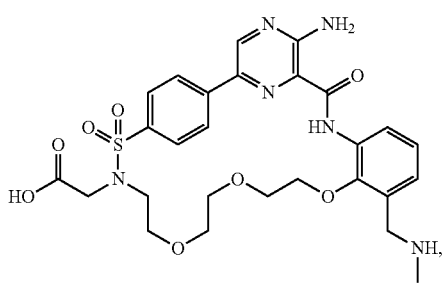
ATRN 6-B -continued

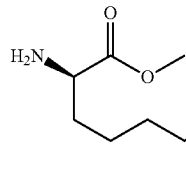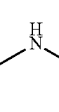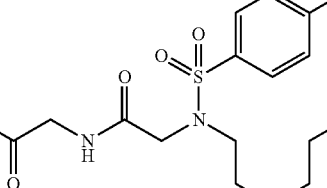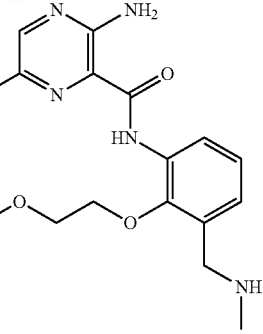

ATRN 7

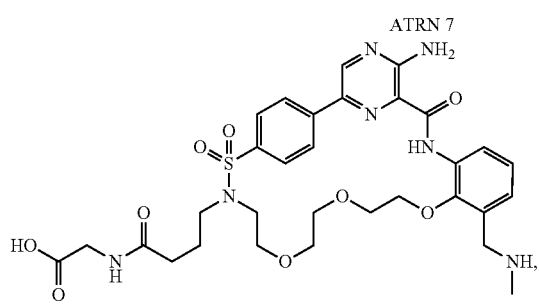

ATRN 7-A

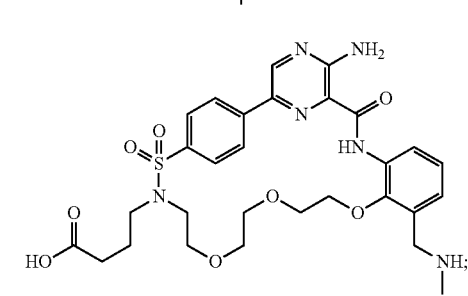

ATRN 7-B or a pharmaceutically acceptable salt thereof.

30. A pharmaceutical composition comprising a compound of claim 1, and a pharmaceutically acceptable carrier.

31. The pharmaceutical composition of claim 30, further comprising an enzyme inhibitor.

32. A method of modulating or ameliorating pancreatic cancer, lung cancer, or colorectal cancer in a patient comprising administering to the patient a compound of claim 1.

33. The method of claim 32, wherein the compound is administered in combination with another therapeutic chemotherapy agent.

34. The method of claim 32, wherein the compound is administered in combination with an enzyme inhibitor.

35. The method of claim 32, that is for ameliorating the pancreatic cancer, lung cancer, or colorectal cancer.

36. The method of claim 32, that is for modulating the pancreatic cancer, lung cancer, or colorectal cancer.

37. The method of claim 36, wherein the modulating comprises stabilizing a physical symptom of the pancreatic cancer, lung cancer, or colorectal cancer.

38. The method of claim 36, wherein the modulating comprises stabilizing a physical parameter of the pancreatic cancer, lung cancer, or colorectal cancer.

39. A method of modulating or ameliorating a cancer that is breast cancer, prostate cancer, gastric cancer, ovarian cancer, or glioblastoma in a patient comprising administering to the patient a compound of claim 1.

40. The method of claim 39, wherein the compound is administered in combination with another therapeutic chemotherapy agent.

41. The method of claim 39, wherein the compound is administered in combination with an enzyme inhibitor.

42. The method of claim 39, that is for ameliorating the cancer.

43. The method of claim 39, that is for modulating the cancer.

44. The method of claim 41, wherein the modulating comprises stabilizing a physical symptom of the cancer.

45. The method of claim 41, wherein the modulating comprises stabilizing a physical parameter of the cancer.

* * * * *